US008425898B2

(12) United States Patent
Sampson et al.

(10) Patent No.: US 8,425,898 B2
(45) Date of Patent: Apr. 23, 2013

(54) COMPOSITIONS, METHODS, AND KITS FOR ELICITING AN IMMUNE RESPONSE

(75) Inventors: John H. Sampson, Durham, NC (US); Duane A. Mitchell, Durham, NC (US)

(73) Assignee: Duke University, Durham, NC (US)

( * ) Notice: Subject to any disclaimer, the term of this patent is extended or adjusted under 35 U.S.C. 154(b) by 383 days.

(21) Appl. No.: 12/488,176

(22) Filed: Jun. 19, 2009

(65) Prior Publication Data

US 2012/0288473 A1 Nov. 15, 2012

Related U.S. Application Data

(60) Provisional application No. 61/074,582, filed on Jun. 20, 2008.

(51) Int. Cl.
*A61K 39/245* (2006.01)
(52) U.S. Cl.
USPC ............. 424/93.3; 424/230.1; 435/5; 435/7.1
(58) Field of Classification Search ........................ None
See application file for complete search history.

(56) References Cited

U.S. PATENT DOCUMENTS

| | | | |
|---|---|---|---|
| 4,906,564 A | 3/1990 | Lyon et al. | |
| 4,957,735 A | 9/1990 | Huang et al. | |
| 5,833,975 A | 11/1998 | Paoletti et al. | |
| 6,013,258 A | 1/2000 | Urban et al. | |
| 6,074,645 A * | 6/2000 | Diamond et al. | 424/186.1 |
| 6,156,317 A | 12/2000 | Diamond et al. | |
| 6,207,161 B1 | 3/2001 | Pande et al. | |
| 6,251,399 B1 * | 6/2001 | Diamond et al. | 424/186.1 |
| 6,291,446 B1 | 9/2001 | Ways et al. | |
| 6,306,388 B1 | 10/2001 | Nair et al. | |
| 6,350,451 B1 | 2/2002 | Horn et al. | |
| 6,503,503 B1 | 1/2003 | Bigner et al. | |
| 6,562,376 B2 | 5/2003 | Hooper et al. | |
| 6,572,856 B1 | 6/2003 | Taylor et al. | |
| 6,579,970 B2 | 6/2003 | Nicolette et al. | |
| 6,726,910 B2 * | 4/2004 | Diamond | 424/186.1 |
| 6,733,973 B2 * | 5/2004 | Diamond | 435/6.14 |
| 7,084,249 B1 | 8/2006 | Eisenbach et al. | |
| 7,163,685 B2 * | 1/2007 | Diamond et al. | 424/199.1 |
| 7,202,331 B2 | 4/2007 | Nicolette et al. | |
| 7,318,924 B2 | 1/2008 | McKenzie et al. | |
| 7,888,112 B2 | 2/2011 | Hermanson et al. | |
| 8,097,256 B2 | 1/2012 | Yu et al. | |
| 2002/0064874 A1 | 5/2002 | Vie et al. | |
| 2002/0164579 A1 | 11/2002 | Nelson et al. | |
| 2002/0176870 A1 | 11/2002 | Schall et al. | |
| 2003/0118602 A1 | 6/2003 | Diamond et al. | |
| 2003/0120060 A1 | 6/2003 | Gonczol et al. | |
| 2004/0082005 A1 | 4/2004 | Cobbs et al. | |
| 2004/0241140 A1 | 12/2004 | Pavlakis et al. | |
| 2004/0265325 A1 | 12/2004 | Diamond et al. | |
| 2005/0019344 A1 | 1/2005 | Khanna et al. | |
| 2005/0232933 A1 | 10/2005 | Zaia et al. | |
| 2006/0188520 A1 | 8/2006 | Steinman et al. | |
| 2006/0233770 A1 | 10/2006 | Ambinder et al. | |
| 2007/0141026 A1 | 6/2007 | Winqvist et al. | |
| 2008/0311141 A1 | 12/2008 | Yu et al. | |
| 2010/0111992 A1 * | 5/2010 | Albani et al. | 424/186.1 |
| 2011/0236345 A1 | 9/2011 | Sampson et al. | |

FOREIGN PATENT DOCUMENTS

| | | |
|---|---|---|
| WO | WO 92-05263 A1 | 4/1992 |
| WO | WO 94-21807 A1 | 9/1994 |
| WO | WO 2006-056027 A1 | 6/2006 |

OTHER PUBLICATIONS

Weihrauch et al. Clinical Cancer Research 2005, vol. 11, pp. 5993-6001.*
Carlsson, B., et al., Ex Vivo Stimulation of Cytomegalovirus (CMV)-Specific T Cells Using CMV pp65-Modified Dendritic Cells as Stimulators, *British J. Haematology*, 121(3): 428-438 (2003).
Mitchell, D., et al., "RNA Transfected Dendritic Cell Vaccines Targeting Human Cytomegalovirus Antigens in Patients with Glioblastoma," *Molecular Therapy*, 17(1): S93 (2009).
Van Den Bosch, G.A., et al., "Ex Vivo Induction of Viral Antigen-Specific CD8(+) T Cell Responses Using mRNA-Epectroporated CD40-Activated B Cells," *Clin. Experimental Immunology*, 139(3): 458-467 (2005).
Supplementary European Search Report; date of completion: Aug. 20, 2012.
2004N-0355 Scientific Considerations Related to Developing Biotechnology Products, FDA Comment No. EC8 online}, LeClair, J., Retreived on Apr. 21, 2008, Retrieved from the Internet: http://www.fda.gov/ohrms/dockets/dockets/04n0355/04N-0355-EC8.html.
A Clinician and Researcher's Hybrid Approach to Understanding Brain Tumors, Cobbs, C.S., Retrieved on Apr. 14, 2008}, Retrieved from the Internet: http://www.cpmc.org/professionals/research/currents/2005researchrptcobbs.html.
Adler, S.P., et al., "A Canarypox Vector Expressing Cytomegalovirus (CMV) Glycoprotein B Primes for Antibody Responses to a Live Attenuated CMV Vaccine (Towne)," *J. Infec. Dis.*, 180: 843-846 (1999).
Bolton, A.E.. and W.M. Hunter, "The Labelling of Proteins to High Specific Radioactivities by Conjugation to a $^{125}$I-Containing Acylating Agent," *Biochem J.*, 133: 529-539 (1973).
Chee, M.S., et al., "Analysis of the Protein-Coding Content of the Sequence of Human Cytomegalovirus Strain AD169," *Curr. Top. Microbiol. Immunol.*, 154 :125-169 (1990).
Cinatl, Jr., J., et al., "Oncomodulatory Signals by Regulatory Proteins Enclodedby Human Cytomegalovirus: A Novel Role for Viral Infection in Tumor Progression," *FEMS Microbiology Reviews 28*: 59-77 (2004).
Cobb, C.S., et al., "Modulation of Oncogenic Phenotype in Human Glioma Cells by Cytomegalovirus IE1-Mediated Mitogenicity," *Cancer Research 68*(3): 724-730 (2008).
Cobbs, C.S., "Human Cytomegalovirus Induces Cellular Tyrosine Kinase Signaling and Promotes Glioma Cell Invasiveness," *Journal of Neurooncology*, 85: 271-280 (2007).
Cobbs, C.S., et al., "Human Cytomegalovirus infection and Expression in Human Malignant Glioma,"*Cancer Research*, 62: 3347-3350 (2002).
Connor, J., et al., "Monoclonal Antibody and Liposomes," *Pharmacol. Ther.*, 28: 341-365 (1985).

(Continued)

*Primary Examiner* — Bao Li
(74) *Attorney, Agent, or Firm* — Womble Carlyle Sandridge & Rice, LLP

(57) ABSTRACT

The present invention relates to compositions, methods, and kits for eliciting an immune response to at least one CMV antigen expressed by a cancer cell, in particular for treating and preventing cancer. CMV determination methods, compositions, and kits also are provided.

8 Claims, 19 Drawing Sheets

OTHER PUBLICATIONS

Converse, P.J., et al., "Immune Responses to Fractionated Cytomegalovirus (CMV) Antigens After HIV Infection. Loss of Cellular and Humoral Reactivity to Antigens Recognized by HIV—CMV+Individuals," Clin. Exp. Immunol., 82: 559-566 (1990).
GenEMBL Database Accession No. BK000394, May 1, 2009.
GenEMBL Database Accession No. X17403, Nov . 12, 2006.
Harkins, L., et al., "Specific Localisation of Human Cytomegalovirus Nucleic Acids and Proteins in Human Colorectal Cancer," Lancet 360: 1557-1563 (2002).
Hung, C-F., et al., "DNA Vaccines for Cervical Cancer: From Bench to Bedside," Exper. Molecul. Medicine 39(6): 679-689 (2007).
International Search Report (PCT/US2009/047987; mailed Mar. 3, 2010).
Kaplitt, M.G., et al., "Expression of a Functional Foreign Gene in Adult Mammalian Brain following in Vivo Transfer via a Herpes Simplex Virus Type 1 Defective Viral Vector," Molec. Cell. Neurosci. 2: 320-330 (1991).
Kiecker, F., et al, "Analysis of Antigen-Specific T-Cell Responses with Synthetic Peptides—What Kind of Peptide for Which Purpose?" Hum. Immunol. 65: 523-536 (2004).
LaFemina R. and G.S. Hayward, "Constitutive and Retinoic Acid-Induced Expression of Cytomegalovisur Immediate-Early Genes im Human Teratocarcinoma Cells," J. Virol., 58(2): 434-440 (1986).
La Salle, G, et al., "An Adenovirus Vector for Gene Transfer Into Neurons and Glia in the Brain," Science 259: 988-990 (1993).
Lebkowski, J.S., et al., "Adeno-Associated Virus: A Vector System for Efficient Introduction and Integration of DNA into a Variety of Mammalian Cell Types," Mol. Cell. Biol. 8(10): 3988-3996 (1988).
Miller, A. D. and Guy J.Rosman, "Improved Retroviral Vectors for Gene Transfer and Expression," BioTechniques, 7(9) :980-990 (1992).
Mitchell, D.A., et al., "Selective Modification of Antigen-Specific T Cells by RNA Electroporation," Human Gene Therapy 19(5): 511-521 (2008).
Mitchell, D.A., et al., "Sensitive Detection of Human Cytomegalovirus in Tumors and Peripheral Blood of Patients Diagnosed with Glioblastoma," Neuro-Oncology 10: 10-18 (2008).
Morrison, M., "The Determination of the Exposed Proteins on Membranes by the Use of Lactoperoxidase," Methods in Enzymology, 32B: 103-109 (1974).
Nair S., et al., "Synergy Between Tumor Immunotherapy and Antiangiogenic Therapy," Blood, 102(3): 964-971 (2003).
Nesbitt, S.E., et al., "Cytomegalovirus Quantitation by Real-Time PCR Is Unaffected by Delayed Separation of Plasma from Whole Blood," J. Clin. Microbiology, 42(3): 1296-1297 (2004).
Pass, R.F., et al., "A Subunit Cytomegalovirus Vaccine Based on Recombinant Envelope Glycoprotein B and a New Adjuvant," J. Infect. Dis., 180: 970-975 (1999).
Peggs K., et al., "Induction of Cytomegalovirus (CMV)-Specific T-Cell Responses using Dendritic Cells Pulsed with CMV Antigen: A Novel Culture System Free of Live CMV Virions," Blood 97(4): 994-1000 (2001).
Poltermann, s., et al., "Lack of Association of Herpesvirus with Brain Tumors," J. Neurovirology, 12(2): 90-99 (2006).
Prins, R.M., et al., "Cytomegalovirus Immunity after Vaccination with Autologous Glioblastoma Lysate," New Engl. Journal Med., 359(5): 539-541, 2008.
Quinnan, G.V., et al, "Comparative Virulence and Immunogenicity of the Towne Strain and a Nonattended Strain of Cytomegalovirus," Ann. Intern. Med., 101: 478-483 (1984).
Researchers Develop Vaccine for Brain Cancer [online], Sass, R., [Retreived on Oct. 23, 2007], Retreived from the Internet: http://www.associatedcontent.com/article/423598/researchers_develop_vaccine_for_bain.html?cat=5.
Samanta, M., et al., "High Prevalence of Human Cytomegalovirus in Prostatic Intraepithelial Neoplasia and Prostatic Carcinoma," Journ. of Urology, 170: 998-1002 (2003).
Samulski, R.J., et al., "A Recombinant Plasmid from Which an Infectious Aden-Associated Virus Genome Can Be Excised in Vitro and Its Use to Study Viral Replication," J. Virol. 61(10): 3096-3101 (1987).

Samulski, R.J., et al., "Helper-Free Stocks of Recombinant Adena-Associated Viruses: Normal Integration Does Not Require Viral Gene Expression," J. Virol. 63(9): 3822-3828 (1989).
Scheurer et al., "Detection of Human Cytomegalovirus in Different Histological Types of Gliomas," Acta Neuropathologica, 116: 79-86 (2008).
Schlehofer, J.R., et al., "Response from Authors RE:" Lack of Association of Herpesvirus with Brain Tumors, J. Neurovirology, 13(1): 86-87 (2007).
Soderberg-Naucler, C., "HCMV Microinfections in Inflammatory Diseases and Cancer," J.Clin. Virol., 41(3): 218-223 (2008), Epub. Dec. 27, 2007.
Spaete, R.R., et al., "Human Cytomegalovirus Structural Proteins," J. Gen. Virology, 75: 3287-3308 (1994).
Stratford-Perricaudet, L.D., et al., "Widespread Long-Term Gene Transfer to Mouse Skeletal Muscles and Heart," J. Clin. Invest. 90: 626-630 (1992).
Stupp, R., et al., "Radiotherapy Plus Concomitant and Adjuvant Temozolomide for Glioblastoma," N. Engl. J. Med. 352(10): 987-996 (2005).
Swiss-Prot Accession No, P06725, Nov. 2009.
Swiss-Prot Accession No. P13202, Nov. 2009.
Syvanen, J.M., et al., "Preparation of $^{125}$I-Catalytic Subunit of Aspartate Transcarbamylase and Its Use in Studies of the Regulatory Subunit," J. Biol. Chem., 248(11): 3762-3768 (1973).
Szmania, S., et al., "Isolation and Expansion of Cytomegalovirus-Specific Cytotoxic T Lymphocytes to Clinical Scale from a Single Blood Draw Using Dendritic Cells and HLA-Tetramers," Blood 98: 505-512 (2001).
Trlvedi D., et al., "Generation of CMV-Specific T Lymphocytes Using Protein-Spanning Pools of PP65-Dervied Overlapping Pentadecapeptides for Adoptive Immunotherapy," Blood, 105(7); 2793-2801 (2005).
Vaccine Therapy in Treating Patients with Newly Diagnosed Glioblastoma Multiforme [online]. Duke University. Clinicaltrials.gov Identifier::NCT00643097 [retrieved on Apr. 21, 2008]. Retreived from the Internet: ,http://clinicaltrials.gov/ct2/show/record/NCT00639639>.
Wang, X.G., et al., "Treating Cancer as an Infectious Disease- Viral Antigens as Novel Targets for Treatment and Potential Prevention of Tumors of Viral Etiology," PLoS ONE 2(10): e1114. doi:10.1371/journal.pone.0001114, 2007.
Westphal, M., et al., "A Phase 3 Trial of Local Chemotherapy with Biodegradable Carmustine (BCNU) Wafers (Gliadel Wafers) in Patients with Primary Malignant Glioma," Neuro Oncol., 5:79-88 (2003).
Zhao, Y., et al., "Inhibition of Invariant Chain Expression in Dendritic Cells Presenting Endogenous Antigens Stimulates CD4 T-Cell Responses and Tumor Immunity," Blood, 102 (12): 4137-4142 (2003).
Axelsson, F., et al., "Humoral immunity targeting site I of antigenic domain 2 of glycoprotein B upon immunization with different cytomegalovirus candidate vaccines," Vaccine 26: 41-46 (2007).
Beckman Coulter, A-1983A, "Detection and Enumeration of CMV Antigen-Specific CD8-Positive T Lymphocytes in Whole Blood by Flow Cytometry," (2005).
Bui, H-H, et al., "Predicting population coverage of T-cell epitope-based diagnostics and vaccines," BMC Bioinformatics 7: 153 (2006).
Elkington, R., et al., "Ex Vivo Profiling of CD8 -T-Cell Responses to Human Cytomegalovirus Reveals Broad and Multispecific Reactivities in Healthy Virus Carriers," Journal of Virology, 77(9): 5226-5240 (2003).
Gratama, J.W., et al., "Diagnostic potential of tetramer-based monitoring of cytomegalovirusspecific CD8 T lymphocytes in allogeneic stem cell transplantation," Clinical Immunology, 106: 29-35 (2003).
Harcourt, G.C., et al., "Identification of key peptide-specific CD4+ T cell responses to human cytomegalovirus: implications for tracking antiviral populations," Clinical and Experimental Immunology, 146: 203-210 (2006).
Khan, N., "The immunological burden of human cytomegalovirus infection," Arch. Immunol. Ther. Exp., 55: 299-308 (2007).
Khanna, R., et al., "Human cytomegalovirus vaccine: time to look for alternative options," Trends in Molecular Medicine, 12(1): 26-33 (2006).

Lantto, J., et al., "Binding characteristics determine the neutralizing potential of antibody fragments specific for antigenic domain 2 on glycoprotein B of human cytomegalovirus," *Virology 305*: 201-209 (2003).

Longmate, J., et al., "Population Coverage by HLA Class-I Restricted Cytotoxic T-Lymphocyte Epitopes," *Immunogenics*, 52: 165-173 (2001).

Marshall, G.S., et al., "Antibodies to the Major Linear Neutralizing Domains of Cytomegalovirus Glycoprotein B Among Natural Seropositives and CMV Subunit Vaccine Recipients," *Viral Immun. 13*(3): 329-341 (2000).

Nastke, M.D., et al., "Major contribution of codominant CD8 and CD4 T cell epitopes to the human cytomegalovirus-specific T cell repertoire," *CMLS, Cell. Mol. Life Sci.*, 62: 77-86 (2005).

Plotkin, S.A., "Is there a formula for an effective CMV vaccine?" *Journal of Clinical Virology*, 25: S13 -S21 (2002).

Ponsaerts, P., et al., "Cancer immunotherapy using RNA-loaded dendritic cells," *Clin. Exp. Immunol.*, 134: 378-384 (2003).

Rist, M., et al., "Ex vivo expansion of human cytomegalovirus-specific cytotoxic T cells by recombinant polyepitope: implications for HCMV immunotherapy," *Eur. J. Immunol.*, 35: 996-1007 (2005).

Schrader, J.W., "Location, location, timing: Analysis of cytomegalovirus epitopes for neutralizing antibodies," *Immun. Letters*, 112: 58-60 (2007).

Sette, A., et al., "Epitope-based vaccines: an update on epitope identification, vaccine design and delivery," *Current Opinion in Immunology*, 15:461-470 (2003).

Slezak, S.L., et al., "CMV pp65 and IE-1 T cell epitopes recognized by healthy subjects," *Journal of Translational Medicine*, 5:17 (2007).

Southwick, P.C., "MHC Tetramers for Monitoring CMV Response," ASHI Quarterly, (26) (2002).

Weihrauch, M.R., et al., "Phase I/II Combined Chemoimmunotherapy with Carcinoembryonic Antigen—Derived HLA-A2—Restricted CAP-1 Peptide and Irinotecan, 5-Fluorouracil, and Leucovorin in Patients with Primary Metastatic Colorectal Cancer ," *Clinical Cancer Res. 11*:5993-6001 (2005).

Zhong, J., et al., "Induction of Pluripotent Protective Immunity Following Immunisation with a Chimeric Vaccine against Human Cytomegalovirus," PLoS ONE 3(9): e3256 (2008).

LeClair, J., "2004N-0355—Scientific Considerations Related to Developing Biotechnology Products," (2004); pp. 1-XX. {Retrieved on Jan. 11, 2012} Retrieved from the Internet: http://www.fda.gov/ohrms/dockets/dockets/04n0355/04N-0355-EC5.html.

Cobbs, Charles, S., "A Clinician and Researcher's Hybrid Approach to Understanding Brain Tumors," (2005); pp. 1-XX. {Retrieved on Jan. 11, 2012} Retrieved from the Internet: http://www.cpmc.org/professionals/research/currents/2005researchrptcobbs.html.

Davison, A. J., GenBank Accession No. BK000394; Submitted (May 1, 2002); pp. 1-101.

Chee, M., GenBank Accession No. X17403; Submitted (Dec. 6, 1989); pp. 1-122.

Ruger, B., et al., Swiss-Prot Accession No. P06725; Submitted (Jan. 1, 1988); pp. 1-3.

Akrigg, A., et al., Swiss-Prot Accession No. P13202; Submitted (Jan. 1, 1990); pp. 1-2.

* cited by examiner

SEQUENCE LISTING

```
<160> NUMBER OF SEQ ID NOS: 131

<210> SEQ ID NO 1
<211> LENGTH: 561
<212> TYPE: PRT
<213> ORGANISM: Human cytomegalovirus

<400> SEQUENCE: 1

Met Glu Ser Arg Gly Arg Arg Cys Pro Glu Met Ile Ser Val Leu Gly
 1               5                  10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300
```

```
Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365

Phe Thr Ser Gln Tyr Arg Ile Gln Gly Lys Leu Glu Tyr Arg His Thr
370                 375                 380

Trp Asp Arg His Asp Glu Gly Ala Ala Gln Gly Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Gly Ala Met Ala Gly Ala Ser Thr Ser
            420                 425                 430

Ala Gly Arg Lys Arg Lys Ser Ala Ser Ser Ala Thr Ala Cys Thr Ser
        435                 440                 445

Gly Val Met Thr Arg Gly Arg Leu Lys Ala Glu Ser Thr Val Ala Pro
450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
            500                 505                 510

Phe Phe Trp Asp Ala Asn Asp Ile Tyr Arg Ile Phe Ala Glu Leu Glu
        515                 520                 525

Gly Val Trp Gln Pro Ala Ala Gln Pro Lys Arg Arg Arg His Arg Gln
530                 535                 540

Asp Ala Leu Pro Gly Pro Cys Ile Ala Ser Thr Pro Lys Lys His Arg
545                 550                 555                 560

Gly

<210> SEQ ID NO 2
<211> LENGTH: 906
<212> TYPE: PRT
<213> ORGANISM: Human cytomegalovirus

<400> SEQUENCE: 2

Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Ser His Ala Thr
                20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110

Ser Met Lys Pro Ile Asn Glu Asp Leu Asp Glu Gly Ile Met Val Val
```

```
                115                 120                 125
Tyr Lys Arg Asn Ile Val Ala His Thr Phe Lys Val Arg Val Tyr Gln
130                 135                 140
Lys Val Leu Thr Phe Arg Arg Ser Tyr Ala Tyr Ile Tyr Thr Thr Tyr
145                 150                 155                 160
Leu Leu Gly Ser Asn Thr Glu Tyr Val Ala Pro Pro Met Trp Glu Ile
                165                 170                 175
His His Ile Asn Lys Phe Ala Gln Cys Tyr Ser Ser Tyr Ser Arg Val
                180                 185                 190
Ile Gly Gly Thr Val Phe Val Ala Tyr His Arg Asp Ser Tyr Glu Asn
                195                 200                 205
Lys Thr Met Gln Leu Ile Pro Asp Asp Tyr Ser Asn Thr His Ser Thr
210                 215                 220
Arg Tyr Val Thr Val Lys Asp Gln Trp His Ser Arg Gly Ser Thr Trp
225                 230                 235                 240
Leu Tyr Arg Glu Thr Cys Asn Leu Asn Cys Met Leu Thr Ile Thr Thr
                245                 250                 255
Ala Arg Ser Lys Tyr Pro Tyr His Phe Phe Ala Thr Ser Thr Gly Asp
                260                 265                 270
Val Val Tyr Ile Ser Pro Phe Tyr Asn Gly Thr Asn Arg Asn Ala Ser
                275                 280                 285
Tyr Phe Gly Glu Asn Ala Asp Lys Phe Phe Ile Phe Pro Asn Tyr Thr
                290                 295                 300
Ile Val Ser Asp Phe Gly Arg Pro Asn Ala Ala Pro Glu Thr His Arg
305                 310                 315                 320
Leu Val Ala Phe Leu Glu Arg Ala Asp Ser Val Ile Ser Trp Asp Ile
                325                 330                 335
Gln Asp Glu Lys Asn Val Thr Cys Gln Leu Thr Phe Trp Glu Ala Ser
                340                 345                 350
Glu Arg Thr Ile Arg Ser Glu Ala Glu Asp Ser Tyr His Phe Ser Ser
                355                 360                 365
Ala Lys Met Thr Ala Thr Phe Leu Ser Lys Lys Gln Glu Val Asn Met
370                 375                 380
Ser Asp Ser Ala Leu Asp Cys Val Arg Asp Glu Ala Ile Asn Lys Leu
385                 390                 395                 400
Gln Gln Ile Phe Asn Thr Ser Tyr Asn Gln Thr Tyr Glu Lys Tyr Gly
                405                 410                 415
Asn Val Ser Val Phe Glu Thr Ser Gly Gly Leu Val Val Phe Trp Gln
                420                 425                 430
Gly Ile Lys Gln Lys Ser Leu Val Glu Leu Glu Arg Leu Ala Asn Arg
                435                 440                 445
Ser Ser Leu Asn Ile Thr His Arg Thr Arg Arg Ser Thr Ser Asp Asn
                450                 455                 460
Asn Thr Thr His Leu Ser Ser Met Glu Ser Val His Asn Leu Val Tyr
465                 470                 475                 480
Ala Gln Leu Gln Phe Thr Tyr Asp Thr Leu Arg Gly Tyr Ile Asn Arg
                485                 490                 495
Ala Leu Ala Gln Ile Ala Glu Ala Trp Cys Val Asp Gln Arg Arg Thr
                500                 505                 510
Leu Glu Val Phe Lys Glu Leu Ser Lys Ile Asn Pro Ser Ala Ile Leu
                515                 520                 525
Ser Ala Ile Tyr Asn Lys Pro Ile Ala Ala Arg Phe Met Gly Asp Val
530                 535                 540
```

```
Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
            565                 570                 575

Pro Val Val Ile Phe Asn Phe Ala Asn Ser Ser Tyr Val Gln Tyr Gly
                580                 585                 590

Gln Leu Gly Glu Asp Asn Glu Ile Leu Leu Gly Asn His Arg Thr Glu
            595                 600                 605

Glu Cys Gln Leu Pro Ser Leu Lys Ile Phe Ile Ala Gly Asn Ser Ala
        610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Lys Val Val Asp Pro Leu
690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
        755                 760                 765

Leu Ile Tyr Thr Arg Gln Arg Arg Leu Cys Thr Gln Pro Leu Gln Asn
770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
        835                 840                 845

Leu Ala Leu Ala Arg Leu Asp Ala Glu Gln Arg Ala Gln Gln Asn Gly
850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Asn Val
            900                 905

<210> SEQ ID NO 3
<211> LENGTH: 491
<212> TYPE: PRT
<213> ORGANISM: Human cytomegalovirus

<400> SEQUENCE: 3

Met Glu Ser Ser Ala Lys Arg Lys Met Asp Pro Asp Asn Pro Asp Glu
1               5                   10                  15
```

```
Gly Pro Ser Ser Lys Val Pro Arg Pro Glu Thr Pro Val Thr Lys Ala
            20                  25                  30

Thr Thr Phe Leu Gln Thr Met Leu Arg Lys Glu Val Asn Ser Gln Leu
        35                  40                  45

Ser Leu Gly Asp Pro Leu Phe Pro Glu Leu Ala Glu Glu Ser Leu Lys
    50                  55                  60

Thr Phe Glu Gln Val Thr Glu Asp Cys Asn Glu Asn Pro Glu Lys Asp
65                  70                  75                  80

Val Leu Ala Glu Leu Val Lys Gln Ile Lys Val Arg Val Asp Met Val
                85                  90                  95

Arg His Arg Ile Lys Glu His Met Leu Lys Lys Tyr Thr Gln Thr Glu
            100                 105                 110

Glu Lys Phe Thr Gly Ala Phe Asn Met Met Gly Gly Cys Leu Gln Asn
        115                 120                 125

Ala Leu Asp Ile Leu Asp Lys Val His Glu Pro Phe Glu Glu Met Lys
    130                 135                 140

Cys Ile Gly Leu Thr Met Gln Ser Met Tyr Glu Asn Tyr Ile Val Pro
145                 150                 155                 160

Glu Asp Lys Arg Glu Met Trp Met Ala Cys Ile Lys Glu Leu His Asp
                165                 170                 175

Val Ser Lys Gly Ala Ala Asn Lys Leu Gly Gly Ala Leu Gln Ala Lys
            180                 185                 190

Ala Arg Ala Lys Lys Asp Glu Leu Arg Arg Lys Met Met Tyr Met Cys
        195                 200                 205

Tyr Arg Asn Ile Glu Phe Phe Thr Lys Asn Ser Ala Phe Pro Lys Thr
    210                 215                 220

Thr Asn Gly Cys Ser Gln Ala Met Ala Ala Leu Gln Asn Leu Pro Gln
225                 230                 235                 240

Cys Ser Pro Asp Glu Ile Met Ala Tyr Ala Gln Lys Ile Phe Lys Ile
                245                 250                 255

Leu Asp Glu Glu Arg Asp Lys Val Leu Thr His Ile Asp His Ile Phe
            260                 265                 270

Met Asp Ile Leu Thr Thr Cys Val Glu Thr Met Cys Asn Glu Tyr Lys
        275                 280                 285

Val Thr Ser Asp Ala Cys Met Met Thr Met Tyr Gly Gly Ile Ser Leu
    290                 295                 300

Leu Ser Glu Phe Cys Arg Val Leu Cys Cys Tyr Val Leu Glu Glu Thr
305                 310                 315                 320

Ser Val Met Leu Ala Lys Arg Pro Leu Ile Thr Lys Pro Glu Val Ile
                325                 330                 335

Ser Val Met Lys Arg Arg Ile Glu Glu Ile Cys Met Lys Val Phe Ala
            340                 345                 350

Gln Tyr Ile Leu Gly Ala Asp Pro Leu Arg Val Cys Ser Pro Ser Val
        355                 360                 365

Asp Asp Leu Arg Ala Ile Ala Glu Glu Ser Asp Glu Glu Ala Ile
    370                 375                 380

Val Ala Tyr Thr Leu Ala Thr Ala Gly Val Ser Ser Ser Asp Ser Leu
385                 390                 395                 400

Val Ser Pro Pro Glu Ser Pro Val Pro Ala Thr Ile Pro Leu Ser Ser
                405                 410                 415

Val Ile Val Ala Glu Asn Ser Asp Gln Glu Glu Ser Glu Gln Ser Asp
            420                 425                 430

Glu Glu Glu Glu Glu Gly Ala Gln Glu Glu Arg Glu Asp Thr Val Ser
        435                 440                 445
```

Val Lys Ser Glu Pro Val Ser Glu Ile Glu Glu Val Ala Pro Glu
        450                 455                 460

Glu Glu Asp Gly Ala Glu Glu Pro Thr Ala Ser Gly Gly Lys Ser Thr
465                 470                 475                 480

His Pro Met Val Thr Arg Ser Lys Ala Asp Gln
            485                 490

<210> SEQ ID NO 4
<211> LENGTH: 79
<212> TYPE: PRT
<213> ORGANISM: Human cytomegalovirus

<400> SEQUENCE: 4

Met Leu Ser Val Met Val Ser Ser Leu Val Leu Ile Val Phe Phe
1               5                   10                  15

Leu Gly Ala Ser Glu Glu Ala Lys Pro Ala Thr Thr Thr Ile Lys
            20                  25                  30

Asn Thr Lys Pro Gln Cys Arg Pro Glu Asp Tyr Ala Thr Arg Leu Gln
            35                  40                  45

Asp Leu Arg Val Thr Phe His Arg Val Lys Pro Thr Leu Val Gly His
50                  55                  60

Val Gly Thr Val Tyr Cys Asp Gly Leu Ser Phe Pro Arg Val Gly
65                  70                  75

<210> SEQ ID NO 5
<211> LENGTH: 354
<212> TYPE: PRT
<213> ORGANISM: Human cytomegalovirus

<400> SEQUENCE: 5

Met Thr Pro Thr Thr Thr Thr Ala Glu Leu Thr Thr Glu Phe Asp Tyr
1               5                   10                  15

Asp Glu Asp Ala Thr Pro Cys Val Phe Thr Asp Val Leu Asn Gln Ser
            20                  25                  30

Lys Pro Val Thr Leu Phe Leu Tyr Gly Val Val Phe Leu Phe Gly Ser
            35                  40                  45

Ile Gly Asn Phe Leu Val Ile Phe Thr Ile Thr Trp Arg Arg Arg Ile
50                  55                  60

Gln Cys Ser Gly Asp Val Tyr Phe Ile Asn Leu Ala Ala Ala Asp Leu
65                  70                  75                  80

Leu Phe Val Cys Thr Leu Pro Leu Trp Met Gln Tyr Leu Leu Asp His
            85                  90                  95

Asn Ser Leu Ala Ser Val Pro Cys Thr Leu Leu Thr Ala Cys Phe Tyr
            100                 105                 110

Val Ala Met Phe Ala Ser Leu Cys Phe Ile Thr Glu Ile Ala Leu Asp
        115                 120                 125

Arg Tyr Tyr Ala Ile Val Tyr Met Arg Tyr Arg Pro Val Lys Gln Ala
        130                 135                 140

Cys Leu Phe Ser Ile Phe Trp Trp Ile Phe Ala Val Ile Ile Ala Ile
145                 150                 155                 160

Pro His Phe Met Val Val Thr Lys Lys Asp Asn Gln Cys Met Thr Asp
            165                 170                 175

Tyr Asp Tyr Leu Glu Val Ser Tyr Pro Ile Ile Leu Asn Val Glu Leu
            180                 185                 190

Met Leu Gly Ala Phe Val Ile Pro Leu Ser Val Ile Ser Tyr Cys Tyr
        195                 200                 205

```
Tyr Arg Ile Ser Arg Ile Val Ala Val Ser Gln Ser Arg His Lys Gly
        210                 215                 220

Arg Ile Val Arg Val Leu Ile Ala Val Val Leu Val Phe Ile Ile Phe
225                 230                 235                 240

Trp Leu Pro Tyr His Leu Thr Leu Phe Val Asp Thr Leu Lys Leu Leu
                245                 250                 255

Lys Trp Ile Ser Ser Ser Cys Glu Phe Glu Arg Ser Leu Lys Arg Ala
                260                 265                 270

Leu Ile Leu Thr Glu Ser Leu Ala Phe Cys His Cys Leu Asn Pro
            275                 280                 285

Leu Leu Tyr Val Phe Val Gly Thr Lys Phe Arg Gln Glu Leu His Cys
        290                 295                 300

Leu Leu Ala Glu Phe Arg Gln Arg Leu Phe Ser Arg Asp Val Ser Trp
305                 310                 315                 320

Tyr His Ser Met Ser Phe Ser Arg Arg Ser Ser Pro Ser Arg Arg Glu
                325                 330                 335

Thr Ser Ser Asp Thr Leu Ser Asp Glu Val Cys Arg Val Ser Gln Ile
            340                 345                 350

Ile Pro

<210> SEQ ID NO 6
<211> LENGTH: 21
<212> TYPE: DNA
<213> ORGANISM: Artificial Sequence
<220> FEATURE:
<223> OTHER INFORMATION: Human CMV primer; gB-E1E2

<400> SEQUENCE: 6
tccaacaccc acagtacccg t                                        21

<210> SEQ ID NO 7
<211> LENGTH: 21
<212> TYPE: DNA
<213> ORGANISM: Artificial Sequence
<220> FEATURE:
<223> OTHER INFORMATION: Human CMV primer; gB-E1E2

<400> SEQUENCE: 7
cggaaacgat ggtgtagttc g                                        21

<210> SEQ ID NO 8
<211> LENGTH: 38
<212> TYPE: DNA
<213> ORGANISM: Artificial Sequence
<220> FEATURE:
<223> OTHER INFORMATION: Human CMV primer; gB-ili2

<400> SEQUENCE: 8
cgccgcccgc cccgcgcccg ccgcggcagc acctggct                      38

<210> SEQ ID NO 9
<211> LENGTH: 21
<212> TYPE: DNA
<213> ORGANISM: Artificial Sequence
<220> FEATURE:
<223> OTHER INFORMATION: Human CMV primer; gB-ili2

<400> SEQUENCE: 9
gtaaaccaca tcacccgtgg a                                        21

<210> SEQ ID NO 10
<211> LENGTH: 19
```

```
<212> TYPE: DNA
<213> ORGANISM: Artificial Sequence
<220> FEATURE:
<223> OTHER INFORMATION: Human CMV primer; gB-i3i4

<400> SEQUENCE: 10
gccgcggcag cacctggct                                                  19

<210> SEQ ID NO 11
<211> LENGTH: 18
<212> TYPE: DNA
<213> ORGANISM: Artificial Sequence
<220> FEATURE:
<223> OTHER INFORMATION: Human CMV primer; gB-i3i4

<400> SEQUENCE: 11
aaccacatca cccgtgga                                                   18

<210> SEQ ID NO 12
<211> LENGTH: 20
<212> TYPE: DNA
<213> ORGANISM: Artificial Sequence
<220> FEATURE:
<223> OTHER INFORMATION: Human CMV primer; gB-5/6

<400> SEQUENCE: 12 taccccctatc gcgtgtgttc                                                20

<210> SEQ ID NO 13
<211> LENGTH: 20
<212> TYPE: DNA
<213> ORGANISM: Artificial Sequence
<220> FEATURE:
<223> OTHER INFORMATION: Human CMV primer; gB-5/6

<400> SEQUENCE: 13
ataggaggcg ccacgtattc                                                 20

<210> SEQ ID NO 14
<211> LENGTH: 20
<212> TYPE: DNA
<213> ORGANISM: Artificial Sequence
<220> FEATURE:
<223> OTHER INFORMATION: Human CMV primer; gB-5/7

<400> SEQUENCE: 14 taccccctatc gcgtgtgttc                                                20

<210> SEQ ID NO 15
<211> LENGTH: 20
<212> TYPE: DNA
<213> ORGANISM: Artificial Sequence
<220> FEATURE:
<223> OTHER INFORMATION: Human CMV primer; gB-5/7

<400> SEQUENCE: 15
cctcctataa cgcggctgta                                                 20

<210> SEQ ID NO 16
<211> LENGTH: 20
<212> TYPE: DNA
<213> ORGANISM: Artificial Sequence
<220> FEATURE:
<223> OTHER INFORMATION: Human CMV primer; gB-7B/8

<400> SEQUENCE: 16
tccgaagccg aagactcgta                                                 20
```

<210> SEQ ID NO 17
<211> LENGTH: 20
<212> TYPE: DNA
<213> ORGANISM: Artificial Sequence
<220> FEATURE:
<223> OTHER INFORMATION: Human CMV primer; gB-7B/8

<400> SEQUENCE: 17
gatgtaaccg cgcaacgtgt                                        20

<210> SEQ ID NO 18
<211> LENGTH: 18
<212> TYPE: DNA
<213> ORGANISM: Artificial Sequence
<220> FEATURE:
<223> OTHER INFORMATION: Human CMV primer; gB-9/10

<400> SEQUENCE: 18
tttggagaaa acgccgac                                          18

<210> SEQ ID NO 19
<211> LENGTH: 23
<212> TYPE: DNA
<213> ORGANISM: Artificial Sequence
<220> FEATURE:
<223> OTHER INFORMATION: Human CMV primer; gB-9/10

<400> SEQUENCE: 19
cgcgcggcaa tcggtttgtt gta                                    23

<210> SEQ ID NO 20
<211> LENGTH: 20
<212> TYPE: DNA
<213> ORGANISM: Artificial Sequence
<220> FEATURE:
<223> OTHER INFORMATION: Human CMV primer; gp64/1/2

<400> SEQUENCE: 20
ccgcaacctg gtgcccatgg                                        20

<210> SEQ ID NO 21
<211> LENGTH: 20
<212> TYPE: DNA
<213> ORGANISM: Artificial Sequence
<220> FEATURE:
<223> OTHER INFORMATION: Human CMV primer; gp64/1/2

<400> SEQUENCE: 21
cgtttgggtt gcgcagcggg                                        20

<210> SEQ ID NO 22
<211> LENGTH: 22
<212> TYPE: DNA
<213> ORGANISM: Artificial Sequence
<220> FEATURE:
<223> OTHER INFORMATION: Human CMV primer; gpUL73-1/2

<400> SEQUENCE: 22
ttcggtcggt caacatcgta ag                                     22

<210> SEQ ID NO 23
<211> LENGTH: 22
<212> TYPE: DNA
<213> ORGANISM: Artificial Sequence
<220> FEATURE:
<223> OTHER INFORMATION: Human CMV primer; gpUL73-1/2

```
<400> SEQUENCE: 23
cacccacgta tgtaaacctt ac                                              22

<210> SEQ ID NO 24
<211> LENGTH: 22
<212> TYPE: DNA
<213> ORGANISM: Artificial Sequence
<220> FEATURE:
<223> OTHER INFORMATION: Human CMV primer; IE1-A443/A444

<400> SEQUENCE: 24
agaaagatgt cctggcagaa ct                                              22

<210> SEQ ID NO 25
<211> LENGTH: 22
<212> TYPE: DNA
<213> ORGANISM: Artificial Sequence
<220> FEATURE:
<223> OTHER INFORMATION: Human CMV primer; IE1-A443/A444

<400> SEQUENCE: 25
cctcaggtac aatgtagttc tc                                              22

<210> SEQ ID NO 26
<211> LENGTH: 22
<212> TYPE: DNA
<213> ORGANISM: Artificial Sequence
<220> FEATURE:
<223> OTHER INFORMATION: Human CMV primer; IE1-A445/A446

<400> SEQUENCE: 26
agaaagatgt cctggcagaa ct                                              22

<210> SEQ ID NO 27
<211> LENGTH: 22
<212> TYPE: DNA
<213> ORGANISM: Artificial Sequence
<220> FEATURE:
<223> OTHER INFORMATION: Human CMV primer; IE1-A445/A446

<400> SEQUENCE: 27
cctcaggtac aatgtagttc tc                                              22

<210> SEQ ID NO 28
<211> LENGTH: 20
<212> TYPE: DNA
<213> ORGANISM: Artificial Sequence
<220> FEATURE:
<223> OTHER INFORMATION: Human CMV primer; IE1/2

<400> SEQUENCE: 28
cgtccttgac acgatggagt                                                 20

<210> SEQ ID NO 29
<211> LENGTH: 20
<212> TYPE: DNA
<213> ORGANISM: Artificial Sequence
<220> FEATURE:
<223> OTHER INFORMATION: Human CMV primer; IE1/2

<400> SEQUENCE: 29
attcttcggc caactctgga                                                 20

<210> SEQ ID NO 30
<211> LENGTH: 20
```

```
<212> TYPE: DNA
<213> ORGANISM: Artificial Sequence
<220> FEATURE:
<223> OTHER INFORMATION: Human CMV primer; IE 3/4

<400> SEQUENCE: 30
ccctgataat cctgacgagg                                                   20

<210> SEQ ID NO 31
<211> LENGTH: 21
<212> TYPE: DNA
<213> ORGANISM: Artificial Sequence
<220> FEATURE:
<223> OTHER INFORMATION: Human CMV primer; IE3/4

<400> SEQUENCE: 31
catagtctgc aggaacgtcg t                                                 21

<210> SEQ ID NO 32
<211> LENGTH: 23
<212> TYPE: DNA
<213> ORGANISM: Artificial Sequence
<220> FEATURE:
<223> OTHER INFORMATION: Human CMV primer; IEA1-P1/P2

<400> SEQUENCE: 32
caagcggcct ctgataacca agc                                               23

<210> SEQ ID NO 33
<211> LENGTH: 24
<212> TYPE: DNA
<213> ORGANISM: Artificial Sequence
<220> FEATURE:
<223> OTHER INFORMATION: Human CMV primer; IEA1-P1/P2

<400> SEQUENCE: 33
ctcttcctct ggggcaactt cctc                                              24

<210> SEQ ID NO 34
<211> LENGTH: 23
<212> TYPE: DNA
<213> ORGANISM: Artificial Sequence
<220> FEATURE:
<223> OTHER INFORMATION: Human CMV primer; MIE-P1/P2

<400> SEQUENCE: 34
gggtgctgtc ctgctatgtc tta                                               23

<210> SEQ ID NO 35
<211> LENGTH: 23
<212> TYPE: DNA
<213> ORGANISM: Artificial Sequence
<220> FEATURE:
<223> OTHER INFORMATION: Human CMV primer; MIE-P1/P2

<400> SEQUENCE: 35
catcactctg ctcactttct tcc                                               23

<210> SEQ ID NO 36
<211> LENGTH: 25
<212> TYPE: DNA
<213> ORGANISM: Artificial Sequence
<220> FEATURE:
<223> OTHER INFORMATION: Human CMV primer; pp65-1/2

<400> SEQUENCE: 36
cacctgtcac cgctgctata tttgc                                             25
```

<210> SEQ ID NO 37
<211> LENGTH: 25
<212> TYPE: DNA
<213> ORGANISM: Artificial Sequence
<220> FEATURE:
<223> OTHER INFORMATION: Human CMV primer; pp65-1/2

<400> SEQUENCE: 37
caccacgcag cggcccttga tcttt                                25

<210> SEQ ID NO 38
<211> LENGTH: 18
<212> TYPE: DNA
<213> ORGANISM: Artificial Sequence
<220> FEATURE:
<223> OTHER INFORMATION: Human CMV primer; pp65-3/4

<400> SEQUENCE: 38
gacacaacac cgtaaagc                                        18

<210> SEQ ID NO 39
<211> LENGTH: 16
<212> TYPE: DNA
<213> ORGANISM: Artificial Sequence
<220> FEATURE:
<223> OTHER INFORMATION: Human CMV primer; pp65-3/4

<400> SEQUENCE: 39
cagcgttcgt gtttcc                                          16

<210> SEQ ID NO 40
<211> LENGTH: 20
<212> TYPE: DNA
<213> ORGANISM: Artificial Sequence
<220> FEATURE:
<223> OTHER INFORMATION: Human CMV primer; pp65-11/12

<400> SEQUENCE: 40
agcgcgtaca catagatcga                                      20

<210> SEQ ID NO 41
<211> LENGTH: 22
<212> TYPE: DNA
<213> ORGANISM: Artificial Sequence
<220> FEATURE:
<223> OTHER INFORMATION: Human CMV primer; pp65-11/12

<400> SEQUENCE: 41
gctgatcttg gtatcgcagt ac                                   22

<210> SEQ ID NO 42
<211> LENGTH: 20
<212> TYPE: DNA
<213> ORGANISM: Artificial Sequence
<220> FEATURE:
<223> OTHER INFORMATION: Human CMV primer; pp65-13/14

<400> SEQUENCE: 42
agtggtgcac gttgatgctg                                      20

<210> SEQ ID NO 43
<211> LENGTH: 20
<212> TYPE: DNA
<213> ORGANISM: Artificial Sequence
<220> FEATURE:
<223> OTHER INFORMATION: Human CMV primer; pp65-13/14

```
<400> SEQUENCE: 43
tcgctgatct tggtatcgca                                              20

<210> SEQ ID NO 44
<211> LENGTH: 20
<212> TYPE: DNA
<213> ORGANISM: Artificial Sequence
<220> FEATURE:
<223> OTHER INFORMATION: Human CMV primer; UL54-S1/AS1

<400> SEQUENCE: 44
ctacacggta gcgacgagac                                              20

<210> SEQ ID NO 45
<211> LENGTH: 23
<212> TYPE: DNA
<213> ORGANISM: Artificial Sequence
<220> FEATURE:
<223> OTHER INFORMATION: Human CMV primer; UL54-S1/AS1

<400> SEQUENCE: 45
atgtttctag gctactctga ctg                                          23

<210> SEQ ID NO 46
<211> LENGTH: 20
<212> TYPE: DNA
<213> ORGANISM: Artificial Sequence
<220> FEATURE:
<223> OTHER INFORMATION: Human CMV primer; UL89/93 (EcoRI Fragment
      D-P1/P2)

<400> SEQUENCE: 46
gatccgaccc attgtctaag                                              20

<210> SEQ ID NO 47
<211> LENGTH: 20
<212> TYPE: DNA
<213> ORGANISM: Artificial Sequence
<220> FEATURE:
<223> OTHER INFORMATION: Human CMV primer; UL89/93 (EcoRI Fragment
      D-P1/P2)

<400> SEQUENCE: 47
ggcagctatc gtgactggga                                              20

<210> SEQ ID NO 48
<211> LENGTH: 22
<212> TYPE: DNA
<213> ORGANISM: Artificial Sequence
<220> FEATURE:
<223> OTHER INFORMATION: Human CMV primer; UL144-1/2

<400> SEQUENCE: 48
gcctctgata atgctcatct gc                                           22

<210> SEQ ID NO 49
<211> LENGTH: 22
<212> TYPE: DNA
<213> ORGANISM: Artificial Sequence
<220> FEATURE:
<223> OTHER INFORMATION: Human CMV primer; UL144-1/2

<400> SEQUENCE: 49
ggctagagta tgacgaccgc tt                                           22
```

```
<210> SEQ ID NO 50
<211> LENGTH: 24
<212> TYPE: DNA
<213> ORGANISM: Artificial Sequence
<220> FEATURE:
<223> OTHER INFORMATION: Human CMV primer; UL144-5/6

<400> SEQUENCE: 50
tcgttgtttg tgatgttgga cgcc                                          24

<210> SEQ ID NO 51
<211> LENGTH: 24
<212> TYPE: DNA
<213> ORGANISM: Artificial Sequence
<220> FEATURE:
<223> OTHER INFORMATION: Human CMV primer; UL144-5/6

<400> SEQUENCE: 51
tgaagtgcaa ctgggcaatg agtg                                          24

<210> SEQ ID NO 52
<211> LENGTH: 24
<212> TYPE: DNA
<213> ORGANISM: Artificial Sequence
<220> FEATURE:
<223> OTHER INFORMATION: Human CMV primer; UL144-7/8

<400> SEQUENCE: 52
cgttgtttgt gatgttggac gcct                                          24

<210> SEQ ID NO 53
<211> LENGTH: 24
<212> TYPE: DNA
<213> ORGANISM: Artificial Sequence
<220> FEATURE:
<223> OTHER INFORMATION: Human CMV primer; UL144-7/8

<400> SEQUENCE: 53
tgaagtgcaa ctgggcaatg agtg                                          24

<210> SEQ ID NO 54
<211> LENGTH: 24
<212> TYPE: DNA
<213> ORGANISM: Artificial Sequence
<220> FEATURE:
<223> OTHER INFORMATION: Human CMV primer; UL144-9/10

<400> SEQUENCE: 54
ttgtttgtga tgttggacgc ctgg                                          24

<210> SEQ ID NO 55
<211> LENGTH: 24
<212> TYPE: DNA
<213> ORGANISM: Artificial Sequence
<220> FEATURE:
<223> OTHER INFORMATION: Human CMV primer; UL144-9/10

<400> SEQUENCE: 55
tgaagtgcaa ctgggcaatg agtg                                          24

<210> SEQ ID NO 56
<211> LENGTH: 24
<212> TYPE: DNA
<213> ORGANISM: Artificial Sequence
<220> FEATURE:
<223> OTHER INFORMATION: Human CMV primer; UL144-11/12

<400> SEQUENCE: 56
```

```
atggttctta ggtgcgcata cggt                                          24
```

<210> SEQ ID NO 57
<211> LENGTH: 24
<212> TYPE: DNA
<213> ORGANISM: Artificial Sequence
<220> FEATURE:
<223> OTHER INFORMATION: Human CMV primer; UL144-11/12

<400> SEQUENCE: 57

```
tgaagtgcaa ctgggcaatg agtg                                          24
```

<210> SEQ ID NO 58
<211> LENGTH: 24
<212> TYPE: DNA
<213> ORGANISM: Artificial Sequence
<220> FEATURE:
<223> OTHER INFORMATION: Human CMV primer; UL144-13/14

<400> SEQUENCE: 58

```
aggctagagt atgacgaccg cttt                                          24
```

<210> SEQ ID NO 59
<211> LENGTH: 24
<212> TYPE: DNA
<213> ORGANISM: Artificial Sequence
<220> FEATURE:
<223> OTHER INFORMATION: Human CMV primer; UL144-13/14

<400> SEQUENCE: 59

```
acggcacgta tgtatcggga cttt                                          24
```

<210> SEQ ID NO 60
<211> LENGTH: 25
<212> TYPE: DNA
<213> ORGANISM: Artificial Sequence
<220> FEATURE:
<223> OTHER INFORMATION: Human CMV primer; US7/8 (HindIII-X Fragment-
      P1/P2)

<400> SEQUENCE: 60

```
ggatccgcat ggcattcacg tatgt                                         25
```

<210> SEQ ID NO 61
<211> LENGTH: 25
<212> TYPE: DNA
<213> ORGANISM: Artificial Sequence
<220> FEATURE:
<223> OTHER INFORMATION: Human CMV primer; US7/8 (HindIII-X Fragment-
      P1/P2)

<400> SEQUENCE: 61

```
gaattcagtg gataacctgc ggcga                                         25
```

<210> SEQ ID NO 62
<211> LENGTH: 19
<212> TYPE: DNA
<213> ORGANISM: Artificial Sequence
<220> FEATURE:
<223> OTHER INFORMATION: Human CMV primer; US28-10/11

<400> SEQUENCE: 62

```
agcgtgccgt gtacgttac                                                19
```

<210> SEQ ID NO 63
<211> LENGTH: 18

```
<212> TYPE: DNA
<213> ORGANISM: Artificial Sequence
<220> FEATURE:
<223> OTHER INFORMATION: Human CMV primer; US28-10/11

<400> SEQUENCE: 63
ataaagacaa gcacgacc                                                    18

<210> SEQ ID NO 64
<211> LENGTH: 20
<212> TYPE: DNA
<213> ORGANISM: Artificial Sequence
<220> FEATURE:
<223> OTHER INFORMATION: Human CMV primer; gB-18/19/20

<400> SEQUENCE: 64
aaagagctgc gttccagcaa                                                  20

<210> SEQ ID NO 65
<211> LENGTH: 20
<212> TYPE: DNA
<213> ORGANISM: Artificial Sequence
<220> FEATURE:
<223> OTHER INFORMATION: Human CMV primer; gB-18/19/20

<400> SEQUENCE: 65
gaggtcgtcc agaccttga                                                   20

<210> SEQ ID NO 66
<211> LENGTH: 26
<212> TYPE: DNA
<213> ORGANISM: Artificial Sequence
<220> FEATURE:
<223> OTHER INFORMATION: Human CMV primer; gB-18/19/20

<400> SEQUENCE: 66
catgcgcgaa ttcaactcgt acaagc                                           26

<210> SEQ ID NO 67
<211> LENGTH: 27
<212> TYPE: DNA
<213> ORGANISM: Artificial Sequence
<220> FEATURE:
<223> OTHER INFORMATION: Human CMV primer; gB-21/22/23

<400> SEQUENCE: 67
atcgtgagac ctgtaatctg aactgta                                          27

<210> SEQ ID NO 68
<211> LENGTH: 25
<212> TYPE: DNA
<213> ORGANISM: Artificial Sequence
<220> FEATURE:
<223> OTHER INFORMATION: Human CMV primer; gB-21/22/23

<400> SEQUENCE: 68
ggaagttgca aaaaatgat aagga                                             25

<210> SEQ ID NO 69
<211> LENGTH: 24
<212> TYPE: DNA
<213> ORGANISM: Artificial Sequence
<220> FEATURE:
<223> OTHER INFORMATION: Human CMV primer; gB-21/22/23

<400> SEQUENCE: 69
tgaccatcac tactgcgcgc tcca                                             24
```

```
<210> SEQ ID NO 70
<211> LENGTH: 20
<212> TYPE: DNA
<213> ORGANISM: Artificial Sequence
<220> FEATURE:
<223> OTHER INFORMATION: Human CMV primer; Pp65- 1wx/2wx/3wx

<400> SEQUENCE: 70
ggctacggtt cagggtcaga                                                   20

<210> SEQ ID NO 71
<211> LENGTH: 16
<212> TYPE: DNA
<213> ORGANISM: Artificial Sequence
<220> FEATURE:
<223> OTHER INFORMATION: Human CMV primer; Pp65- 1wx/2wx/3wx

<400> SEQUENCE: 71
ccgggcaagg cgtctt                                                       16

<210> SEQ ID NO 72
<211> LENGTH: 23
<212> TYPE: DNA
<213> ORGANISM: Artificial Sequence
<220> FEATURE:
<223> OTHER INFORMATION: Human CMV primer; Pp65- 1wx/2wx/3wx

<400> SEQUENCE: 72
tgggacgcca acgacatcta ccg                                               23

<210> SEQ ID NO 73
<211> LENGTH: 17
<212> TYPE: DNA
<213> ORGANISM: Artificial Sequence
<220> FEATURE:
<223> OTHER INFORMATION: Human CMV primer; Pp65- 4wx/5wx/6wx

<400> SEQUENCE: 73
gcgcacgagc tggtttg                                                      17

<210> SEQ ID NO 74
<211> LENGTH: 25
<212> TYPE: DNA
<213> ORGANISM: Artificial Sequence
<220> FEATURE:
<223> OTHER INFORMATION: Human CMV primer; Pp65- 4wx/5wx/6wx

<400> SEQUENCE: 74
acaccttgac gtactggtca cctat                                             25

<210> SEQ ID NO 75
<211> LENGTH: 21
<212> TYPE: DNA
<213> ORGANISM: Artificial Sequence
<220> FEATURE:
<223> OTHER INFORMATION: Human CMV primer; Pp65- 4wx/5wx/6wx

<400> SEQUENCE: 75
acgcgcgcaa ccaagatgca g                                                 21

<210> SEQ ID NO 76
<211> LENGTH: 24
<212> TYPE: DNA
<213> ORGANISM: Artificial Sequence
<220> FEATURE:
<223> OTHER INFORMATION: Human CMV primer; Pp65- 7/8/9
```

```
<400> SEQUENCE: 76
acacatagat cgacatgggc tcct                                           24

<210> SEQ ID NO 77
<211> LENGTH: 24
<212> TYPE: DNA
<213> ORGANISM: Artificial Sequence
<220> FEATURE:
<223> OTHER INFORMATION: Human CMV primer; Pp65- 7/8/9

<400> SEQUENCE: 77
tgcaggtgca gcacacgtac ttta                                           24

<210> SEQ ID NO 78
<211> LENGTH: 25
<212> TYPE: DNA
<213> ORGANISM: Artificial Sequence
<220> FEATURE:
<223> OTHER INFORMATION: Human CMV primer; Pp65- 7/8/9

<400> SEQUENCE: 78
ttgtgcacgt tgaccgacac gttct                                          25

<210> SEQ ID NO 79
<211> LENGTH: 15
<212> TYPE: DNA
<213> ORGANISM: Artificial Sequence
<220> FEATURE:
<223> OTHER INFORMATION: Human CMV primer; Pp65-21/22/23

<400> SEQUENCE: 79
tcgcgcccga agagg                                                     15

<210> SEQ ID NO 80
<211> LENGTH: 17
<212> TYPE: DNA
<213> ORGANISM: Artificial Sequence
<220> FEATURE:
<223> OTHER INFORMATION: Human CMV primer; Pp65-21/22/23

<400> SEQUENCE: 80
cggccggatt gtggatt                                                   17

<210> SEQ ID NO 81
<211> LENGTH: 23
<212> TYPE: DNA
<213> ORGANISM: Artificial Sequence
<220> FEATURE:
<223> OTHER INFORMATION: Human CMV primer; Pp65-21/22/23

<400> SEQUENCE: 81
caccgacgag gattccgaca acg                                            23

<210> SEQ ID NO 82
<211> LENGTH: 19
<212> TYPE: DNA
<213> ORGANISM: Artificial Sequence
<220> FEATURE:
<223> OTHER INFORMATION: Human CMV primer; Pp65-24/25/26

<400> SEQUENCE: 82
gcagccacgg gatcgtact                                                 19

<210> SEQ ID NO 83
<211> LENGTH: 23
```

```
<212> TYPE: DNA
<213> ORGANISM: Artificial Sequence
<220> FEATURE:
<223> OTHER INFORMATION: Human CMV primer; Pp65-24/25/26

<400> SEQUENCE: 83
ggcttttacc tcacacgagc att                                              23

<210> SEQ ID NO 84
<211> LENGTH: 20
<212> TYPE: DNA
<213> ORGANISM: Artificial Sequence
<220> FEATURE:
<223> OTHER INFORMATION: Human CMV primer; Pp65-24/25/26

<400> SEQUENCE: 84
cgcgagaccg tggaactgcg                                                  20

<210> SEQ ID NO 85
<211> LENGTH: 20
<212> TYPE: DNA
<213> ORGANISM: Artificial Sequence
<220> FEATURE:
<223> OTHER INFORMATION: Human CMV primer; Pp65-27/28/29

<400> SEQUENCE: 85
gtcagcgttc gtgtttccca                                                  20

<210> SEQ ID NO 86
<211> LENGTH: 20
<212> TYPE: DNA
<213> ORGANISM: Artificial Sequence
<220> FEATURE:
<223> OTHER INFORMATION: Human CMV primer; Pp65-27/28/29

<400> SEQUENCE: 86
gggacacaac accgtaaagc                                                  20

<210> SEQ ID NO 87
<211> LENGTH: 23
<212> TYPE: DNA
<213> ORGANISM: Artificial Sequence
<220> FEATURE:
<223> OTHER INFORMATION: Human CMV primer; Pp65-27/28/29

<400> SEQUENCE: 87
cccgcaaccc gcaacccttc atg                                              23

<210> SEQ ID NO 88
<211> LENGTH: 20
<212> TYPE: DNA
<213> ORGANISM: Artificial Sequence
<220> FEATURE:
<223> OTHER INFORMATION: Human CMV primer; Pp65-30/31/32

<400> SEQUENCE: 88
gcggtaagac gggcaaatac                                                  20

<210> SEQ ID NO 89
<211> LENGTH: 21
<212> TYPE: DNA
<213> ORGANISM: Artificial Sequence
<220> FEATURE:
<223> OTHER INFORMATION: Human CMV primer; Pp65-30/31/32

<400> SEQUENCE: 89
ggcgtcgaga tgttcgtaga g                                                21
```

<210> SEQ ID NO 90
<211> LENGTH: 25
<212> TYPE: DNA
<213> ORGANISM: Artificial Sequence
<220> FEATURE:
<223> OTHER INFORMATION: Human CMV primer; Pp65-30/31/32

<400> SEQUENCE: 90
caccatcgac accacaccct catga                                       25

<210> SEQ ID NO 91
<211> LENGTH: 21
<212> TYPE: DNA
<213> ORGANISM: Artificial Sequence
<220> FEATURE:
<223> OTHER INFORMATION: Human CMV primer; US28-1/2/3

<400> SEQUENCE: 91
cagcgtgccg tgtacgttac t                                           21

<210> SEQ ID NO 92
<211> LENGTH: 24
<212> TYPE: DNA
<213> ORGANISM: Artificial Sequence
<220> FEATURE:
<223> OTHER INFORMATION: Human CMV primer; US28-1/2/3

<400> SEQUENCE: 92
gtgcaatctc cgtgataaaa caca                                        24

<210> SEQ ID NO 93
<211> LENGTH: 30
<212> TYPE: DNA
<213> ORGANISM: Artificial Sequence
<220> FEATURE:
<223> OTHER INFORMATION: Human CMV primer; US28-1/2/3

<400> SEQUENCE: 93
actgcctgtt tctacgtggc tatgtttgcc                                  30

<210> SEQ ID NO 94
<211> LENGTH: 22
<212> TYPE: DNA
<213> ORGANISM: Artificial Sequence
<220> FEATURE:
<223> OTHER INFORMATION: Human CMV primer; US28-4/5/6

<400> SEQUENCE: 94
tggctatgtt tgccagtttg tg                                          22

<210> SEQ ID NO 95
<211> LENGTH: 25
<212> TYPE: DNA
<213> ORGANISM: Artificial Sequence
<220> FEATURE:
<223> OTHER INFORMATION: Human CMV primer; US28-4/5/6

<400> SEQUENCE: 95
caggccgata tctcatgtaa acaat                                       25

<210> SEQ ID NO 96
<211> LENGTH: 28
<212> TYPE: DNA
<213> ORGANISM: Artificial Sequence
<220> FEATURE:
<223> OTHER INFORMATION: Human CMV primer; US28-4/5/6

<400> SEQUENCE: 96
tttatcacgg agattgcact cgatcgct                                    28

<210> SEQ ID NO 97
<211> LENGTH: 27
<212> TYPE: DNA
<213> ORGANISM: Artificial Sequence
<220> FEATURE:
<223> OTHER INFORMATION: Human CMV primer; US28-7/8/9

<400> SEQUENCE: 97
gatgcaatac ctcctagatc acaactc                                     27

<210> SEQ ID NO 98
<211> LENGTH: 23
<212> TYPE: DNA
<213> ORGANISM: Artificial Sequence
<220> FEATURE:
<223> OTHER INFORMATION: Human CMV primer; US28-7/8/9

<400> SEQUENCE: 98
gcaaacatag ccacgtagaa aca                                         23

<210> SEQ ID NO 99
<211> LENGTH: 27
<212> TYPE: DNA
<213> ORGANISM: Artificial Sequence
<220> FEATURE:
<223> OTHER INFORMATION: Human CMV primer; US28-7/8/9

<400> SEQUENCE: 99
ccagcgtgcc gtgtacgtta ctcactg                                     27

<210> SEQ ID NO 100
<211> LENGTH: 21
<212> TYPE: DNA
<213> ORGANISM: Artificial Sequence
<220> FEATURE:
<223> OTHER INFORMATION: Human CMV primer; HXFL4-1/2/3

<400> SEQUENCE: 100
aagcgctgga tacacggtac a                                           21

<210> SEQ ID NO 101
<211> LENGTH: 26
<212> TYPE: DNA
<213> ORGANISM: Artificial Sequence
<220> FEATURE:
<223> OTHER INFORMATION: Human CMV primer; HXFL4-1/2/3

<400> SEQUENCE: 101
gaatacagac acttagagct cggggt                                      26

<210> SEQ ID NO 102
<211> LENGTH: 25
<212> TYPE: DNA
<213> ORGANISM: Artificial Sequence
<220> FEATURE:
<223> OTHER INFORMATION: Human CMV primer; HXFL4-1/2/3

<400> SEQUENCE: 102
ctggccagca cgtatcccaa cagca                                       25

<210> SEQ ID NO 103
<211> LENGTH: 24

```
<212> TYPE: DNA
<213> ORGANISM: Artificial Sequence
<220> FEATURE:
<223> OTHER INFORMATION: Human CMV primer; IE-5/6/7

<400> SEQUENCE: 103
caagaactca gccttcccta agac                                          24

<210> SEQ ID NO 104
<211> LENGTH: 20
<212> TYPE: DNA
<213> ORGANISM: Artificial Sequence
<220> FEATURE:
<223> OTHER INFORMATION: Human CMV primer; IE-5/6/7

<400> SEQUENCE: 104
tgaggcaagt tctgcaatgc                                               20

<210> SEQ ID NO 105
<211> LENGTH: 23
<212> TYPE: DNA
<213> ORGANISM: Artificial Sequence
<220> FEATURE:
<223> OTHER INFORMATION: Human CMV primer; IE-5/6/7

<400> SEQUENCE: 105
ccaatggctg cagtcaggcc atg                                           23

<210> SEQ ID NO 106
<211> LENGTH: 24
<212> TYPE: DNA
<213> ORGANISM: Artificial Sequence
<220> FEATURE:
<223> OTHER INFORMATION: Human CMV primer; IE-8/9/10

<400> SEQUENCE: 106
cagattaagg ttcgagtgga catg                                          24

<210> SEQ ID NO 107
<211> LENGTH: 21
<212> TYPE: DNA
<213> ORGANISM: Artificial Sequence
<220> FEATURE:
<223> OTHER INFORMATION: Human CMV primer; IE-8/9/10

<400> SEQUENCE: 107
aggcgccagt gaatttctct t                                             21

<210> SEQ ID NO 108
<211> LENGTH: 26
<212> TYPE: DNA
<213> ORGANISM: Artificial Sequence
<220> FEATURE:
<223> OTHER INFORMATION: Human CMV primer; IE-8/9/10

<400> SEQUENCE: 108
tgcggcatag aatcaaggag cacatg                                        26

<210> SEQ ID NO 109
<211> LENGTH: 9
<212> TYPE: PRT
<213> ORGANISM: Artificial Sequence
<220> FEATURE:
<223> OTHER INFORMATION: Human CMV pp65 peptide
<220> FEATURE:
<221> NAME/KEY: PEPTIDE
<222> LOCATION: (1)..(9)
```

-continued

<400> SEQUENCE: 109

Asn Leu Val Pro Met Val Ala Thr Val
1               5

<210> SEQ ID NO 110
<211> LENGTH: 88
<212> TYPE: DNA
<213> ORGANISM: Human cytomegalovirus

<400> SEQUENCE: 110
tgataaggaa ttttggagcg cgcagtagtg atggtcacca tacaattcag attacaggtc     60
tcacgataga gccaggtgct gccgcggc                                        88

<210> SEQ ID NO 111
<211> LENGTH: 91
<212> TYPE: DNA
<213> ORGANISM: Human cytomegalovirus

<400> SEQUENCE: 111
gaattttgga gcgcgcagtt agttgatggt tcaccataca atttcaggat ttacaggttc     60
ttcacgatag agccaggttg cttgccgcgg c                                    91

<210> SEQ ID NO 112
<211> LENGTH: 94
<212> TYPE: DNA
<213> ORGANISM: Human cytomegalovirus

<400> SEQUENCE: 112
gtaagggata ctttgggagc gcgccgtagt ggatgggttc accatacagt ttacagatta     60
caggtctcac gatagagcca ggtgctgccg cggc                                 94

<210> SEQ ID NO 113
<211> LENGTH: 98
<212> TYPE: DNA
<213> ORGANISM: Human cytomegalovirus

<400> SEQUENCE: 113
gatgcaatga tagggtactt tgggagcgcg cagtagtgat ggtcagcata cagtttcagt     60
attacaggtc tcacgataga gccaggtgct gccgcggc                             98

<210> SEQ ID NO 114
<211> LENGTH: 96
<212> TYPE: DNA
<213> ORGANISM: Human cytomegalovirus

<400> SEQUENCE: 114
atgcaaagat aagggtactt gggagcgcgc agtagtgatg gtcaccatac aattcagtat     60
tacaggtctc acgatagagc caggtgctgc cgcggc                               96

<210> SEQ ID NO 115
<211> LENGTH: 96
<212> TYPE: DNA
<213> ORGANISM: Human cytomegalovirus

<400> SEQUENCE: 115
tgcaatgata gggtactttg gcagcgcgca gtagtgatgg tcagcataca gtctcagtat     60
tacaggtctc acgatagagc caggtgctgc cgcggc                               96

<210> SEQ ID NO 116
<211> LENGTH: 95

```
<212> TYPE: DNA
<213> ORGANISM: Human cytomegalovirus

<400> SEQUENCE: 116
gcaaatgtaa ggtaacttgg gagcgcgcag tagtgatggg ttcaccatac aattcagatt      60
acaggtctca cgatagagcc aggtgctgcc gcggc                                 95

<210> SEQ ID NO 117
<211> LENGTH: 97
<212> TYPE: DNA
<213> ORGANISM: Human cytomegalovirus

<400> SEQUENCE: 117
atgcaaatga taaggatact ttggagccgc gcagtagtga tggtcaccat acaattcaga      60
ttacaggtct cacgatagag ccaggtgctg ccgcggc                               97

<210> SEQ ID NO 118
<211> LENGTH: 97
<212> TYPE: DNA
<213> ORGANISM: Human cytomegalovirus

<400> SEQUENCE: 118
tgcaatgtaa aggtaacttt ggagcgcgca gtagttgatg gtcagcatac agtttcagat      60
tacaggttct cacgatagag ccaggtgctg ccgcggc                               97

<210> SEQ ID NO 119
<211> LENGTH: 94
<212> TYPE: DNA
<213> ORGANISM: Human cytomegalovirus

<400> SEQUENCE: 119
gcagatgtaa ggtactttgg aagcgcgcag tagtgatggt caccatacaa tttcagatta      60
caggtctcac gatagagcca ggtgctgccg cggc                                  94

<210> SEQ ID NO 120
<211> LENGTH: 98
<212> TYPE: DNA
<213> ORGANISM: Human cytomegalovirus

<400> SEQUENCE: 120
atgcaaaaag ataaggaact tggagccgcg cagtagtgat gggtcaccat acaatctcag      60
attacaggtc tcacgataga gccaggtgct gccgcggc                              98

<210> SEQ ID NO 121
<211> LENGTH: 94
<212> TYPE: DNA
<213> ORGANISM: Human cytomegalovirus

<400> SEQUENCE: 121
gcaatgttaa ggattttggg gagcgcgcag tagtgatggt caccatacaa tttcagatta      60
caggtctcac gatagagcca ggtgctgccg cggc                                  94

<210> SEQ ID NO 122
<211> LENGTH: 89
<212> TYPE: DNA
<213> ORGANISM: Human cytomegalovirus

<400> SEQUENCE: 122
agttagatat ttggagcgcg ccgttattgt tggttcacca tacaatttca gattacaggt      60
ctcacgatag agccaggtgc tgccgcggc                                        89
```

<210> SEQ ID NO 123
<211> LENGTH: 92
<212> TYPE: DNA
<213> ORGANISM: Human cytomegalovirus

<400> SEQUENCE: 123
aaatgataag gaattttgga gcgcgcagta gtgatggtca ccatacaatt tcagattaca    60
ggtctcacga tagagccagg tgctgccgcg gc                                  92

<210> SEQ ID NO 124
<211> LENGTH: 91
<212> TYPE: DNA
<213> ORGANISM: Human cytomegalovirus

<400> SEQUENCE: 124
gcaaatgtaa ggaatttgga gcgcgcagta gtgatggtca ccatacaatt cagattacag    60
gtctcacgat agagccaggt gctgccgcgg c                                   91

<210> SEQ ID NO 125
<211> LENGTH: 91
<212> TYPE: DNA
<213> ORGANISM: Human cytomegalovirus

<400> SEQUENCE: 125
gcaagatagg gtacttggag cgcgcagtag tgatggtcag catacagttc agtattacag    60
gtctcacgat agagccaggt gctgccgcgg c                                   91

<210> SEQ ID NO 126
<211> LENGTH: 85
<212> TYPE: DNA
<213> ORGANISM: Human cytomegalovirus

<400> SEQUENCE: 126
gataggaact tggagcgcgc agtagtgatg gtcaccatac aattcagatt acaggtctca    60
cgatagagcc aggtgctgcc gcggc                                          85

<210> SEQ ID NO 127
<211> LENGTH: 95
<212> TYPE: DNA
<213> ORGANISM: Human cytomegalovirus

<400> SEQUENCE: 127
tgcaatgtaa gggtactttg ggagcgcgca gtagtgatgg tcagcataca gttcagtatt    60
acaggtctca cgatagagcc aggtgctgcc gcggc                               95

<210> SEQ ID NO 128
<211> LENGTH: 92
<212> TYPE: DNA
<213> ORGANISM: Human cytomegalovirus

<400> SEQUENCE: 128
gcaaagatag ggtactttgg agcgcgcagt agtgatggtc accatacagt tcagattaca    60
ggtctcacga tagagccagg tgctgccgcg gc                                  92

<210> SEQ ID NO 129
<211> LENGTH: 99
<212> TYPE: DNA
<213> ORGANISM: Human cytomegalovirus

<400> SEQUENCE: 129

```
gaagcaaagg ataaggaact tggggacgcg cagtagtgat ggtcagccat acagattcag    60
attacaggtc tcacgatagc agccaggtgc tgccgcggc                           99

<210> SEQ ID NO 130
<211> LENGTH: 99
<212> TYPE: DNA
<213> ORGANISM: Human cytomegalovirus

<400> SEQUENCE: 130
gagcgaatag ctaggtactt gggaccgcgc cactagtgaa tggtcaccat acaatttcag    60
attacaggtt ctcacgatag agccaggtgc tgccgcggc                           99

<210> SEQ ID NO 131
<211> LENGTH: 94
<212> TYPE: DNA
<213> ORGANISM: Human cytomegalovirus

<400> SEQUENCE: 131
gagcgaaaat aaggtatttg ggaccgcgca cgagtgatgg tcaccataca attcagatta    60
caggtctcac tatagagcca ggtgctgccg cggc                                94
```

COMPOSITIONS, METHODS, AND KITS FOR ELICITING AN IMMUNE RESPONSE

CROSS-REFERENCE TO RELATED APPLICATIONS

This application claims priority under 35 USC §119 to U.S. Provisional Application No. 61/074,582, filed Jun. 20, 2008, which is herein incorporated by reference in its entirety.

GOVERNMENT INTERESTS

The United States Government has certain interests in this application via grants from the National Institutes of Health, National Cancer Institute, and National Institute of Neurological Disorders and Stroke (NINDS SPORE in Brain Cancer P50-CA1-0876; NCI Dendritic Cell Immunotherapy of Malignant Glioma R01 CA 97222).

FIELD OF THE INVENTION

The present invention relates to compositions, methods, and kits for eliciting an immune response to a cell that expresses a cytomegalovirus (CMV) antigen. The present invention also relates to methods, compositions, and kits for determining CMV.

BACKGROUND OF THE INVENTION

Methods for treating cancers include the use of chemotherapeutics, radiation therapy, and surgery. The identification of a number of tumor antigens has led to attempts at developing cell-based therapies. Some methods have relied on first identifying a tumor antigen, i.e., a polypeptide that is expressed preferentially in tumor cells, relative to non-tumor cells. For example, several human tumor antigens have been isolated from melanoma patients, and identified and characterized.

CMV is a β-herpesvirus. Human cytomegalovirus (HCMV) is endemic in the human population and it has been reported that the virus does not usually cause clinical disease except in immunocompromised hosts. Some human herpesviruses have been implicated in a number of human malignancies including lymphoma, nasopharyngeal cancer, cervical cancer, and Kaposi's sarcoma. Recently, HCMV antigen expression and detection of intact virus has been reported to occur in some tumors.

Despite aggressive multi-modality therapy including surgery, radiation, and chemotherapy, the prognosis for patients with cancer remains relatively poor. Moreover, the non-specific nature of conventional therapy for cancer often results in incapacitating damage to surrounding normal and systemic tissues. Thus, there is a need for the development of effective diagnostic as well as therapeutic and prophylactic strategies that target cancer cells.

SUMMARY OF THE INVENTION

In one aspect, the present invention provides a method of eliciting in a subject an immune response to a cell that expresses a cytomegalovirus (CMV) antigen. The method comprises: administering to the subject a pharmaceutically acceptable composition comprising at least one CMV antigen, or nucleic acids encoding the at least one CMV antigen, wherein the pharmaceutically acceptable composition, when administered to the subject, elicits an immune response to the cell.

In another aspect, the present invention provides a pharmaceutically acceptable composition comprising at least one CMV antigen, or nucleic acids encoding the at least one CMV antigen, wherein the pharmaceutically acceptable composition, when administered to the subject, elicits an immune response to a cell that expresses a CMV antigen.

In some aspects, a prophylactically or therapeutically effective amount of a pharmaceutically acceptable composition is provided by the present invention, wherein the pharmaceutically acceptable composition comprises at least one CMV antigen, or nucleic acids encoding the at least one CMV antigen, wherein the pharmaceutically acceptable composition, when administered to the subject, elicits an immune response to a cell that expresses a CMV antigen.

In other aspects, the present invention provides a method of eliciting in a subject an immune response to a cell that expresses a CMV antigen, the method comprising:
administering to the subject a composition comprising an effective amount of antigen presenting cells, T-lymphocytes, or both, wherein the antigen presenting cells and T lymphocytes have been sensitized in vitro with a sensitizing-effective amount of at least one CMV antigen, wherein the effective amount of antigen presenting cells, T lymphocytes, or both is sufficient to elicit the immune response to the cell that expresses the CMV antigen.

In one aspect, the present invention provides a method for making an antigen-presenting cells, the method comprising: contacting antigen-presenting cells with at least one CMV antigen, or nucleic acids encoding the at least one CMV antigen, in vitro under a condition sufficient for the at least one CMV antigen to be presented by the antigen-presenting cells, wherein the antigen-presenting cell presents the at least one CMV antigen.

In still a further aspect, the present invention provides a composition comprising antigen-presenting cells contacted with at least one CMV antigen, or nucleic acids encoding the at least one CMV antigen, in vitro under a condition sufficient for the at least one CMV antigen to be presented by the antigen-presenting cells.

In some aspects, the present invention provides a method for making lymphocytes, the method comprising:
a) contacting antigen-presenting cells with at least one CMV antigen, or nucleic acids encoding the at least one CMV antigen, in vitro under a condition sufficient for the at least one CMV antigen to be presented by the antigen-presenting cells; and
b) contacting lymphocytes with the antigen-presenting cells of step a) under conditions sufficient to produce the lymphocytes, wherein the lymphocytes are capable of eliciting an immune response against a cell that expresses a CMV antigen.

In other aspects, the present invention provides a composition comprising T lymphocytes contacted with antigen-presenting cells under conditions sufficient to produce T lymphocytes capable of eliciting an immune response against a cell that expresses a CMV antigen, wherein the antigen-presenting cells have been contacted with at least one CMV antigen, or nucleic acids encoding the at least one CMV antigen, in vitro under a condition sufficient for the at least one CMV antigen to be presented by the antigen-presenting cells.

In one aspect, a method for treating or reducing the severity of cancer in a subject is provided by the present invention. The method comprises: administering to the subject a therapeutically or prophylactically effective amount of a composition comprising T lymphocytes contacted with antigen-presenting cells under conditions sufficient to produce T lymphocytes capable of eliciting an immune response against a cell that expresses a CMV antigen, wherein the antigen-presenting cells have been contacted with at least one CMV antigen, or nucleic acids encoding the at least one CMV antigen, in vitro under a condition sufficient for the at least one CMV antigen to be presented by the antigen-presenting cells.

In another aspect, the present invention provides a method for eliciting in a subject an immune response to a cell that expresses a CMV antigen. The method comprises:

administering to the subject a pharmaceutically acceptable composition comprising dendritic cells loaded ex vivo with at least one CMV antigen, or nucleic acids encoding the at least one CMV antigen, wherein the pharmaceutically acceptable composition, when administered to the subject, elicits an immune response to the cell that expresses a CMV antigen.

In some aspects, the present invention provides a method of treating a cell that expresses a CMV antigen, the method comprising administering to a subject a therapeutically or prophylactically effective amount of a pharmaceutically acceptable composition to reduce or inhibit growth or spread of the cell in the subject, wherein the composition comprises:

a) at least one CMV antigen or a polynucleotide encoding the at least one CMV antigen;
b) an anti-CMV antibody;
c) an antigen-presenting cell presenting the at least one CMV antigen, a lymphocyte primed against the CMV antigen, or both; or
d) a combination thereof.

In other aspects, the present invention provides a method of eliciting in a subject an immune response to a cell that expresses a CMV antigen, the method comprising:

administering to the subject a composition comprising an effective amount of antigen-presenting cells, lymphocytes, or both, wherein the antigen-presenting cells and lymphocytes have been sensitized in vitro with a sensitizing-effective amount of at least one CMV antigen, wherein the effective amount of antigen-presenting cells, lymphocytes, or both is sufficient to elicit the immune response to the cell that expresses the CMV antigen.

In one aspect, the present invention provides a method of treating a cell that expresses a CMV antigen, the method comprising administering to a subject a composition comprising an effective amount of antigen-presenting cells, lymphocytes, or both, wherein the antigen-presenting cells have been in vitro contacted with at least one CMV antigen, or nucleic acids encoding the at least one CMV antigen, under a condition sufficient for the at least one CMV antigen to be presented by the antigen-presenting cells, wherein the lymphocytes have been contacted with antigen-presenting cells presenting the at least one CMV antigen.

In another aspect, the present invention provides a method of eliciting in a subject an immune response to a cell that expresses a CMV antigen, the method comprising:

administering to the subject a pharmaceutically acceptable composition comprising an anti-CMV antibody.

In various other aspects, the present invention provides compositions and methods for determining CMV nucleic acid in a subject, preferably CMV DNA in blood or other biological fluid, for example determining subclinical viremia in a sample of blood obtained from the subject. Accordingly, the compositions and methods provide diagnostic, monitoring, and prognostic tests/assays that complement various diagnostic and/or therapeutic procedures and treatments including methods described herein such as, for example, prophylactic and/or therapeutic treating of a disease or condition associated with a precancerous cell, a cancer cell, or a cell-type predisposed to developing cancer associated with CMV.

In other aspects, the present invention provides a kit comprising a pharmaceutically acceptable composition comprising at least one CMV antigen, or nucleic acids encoding the at least one CMV antigen, wherein the pharmaceutically acceptable composition, when administered to a subject, elicits an immune response against a cell that expresses a CMV antigen.

DETAILED DESCRIPTION OF THE INVENTION

Figure 1A:
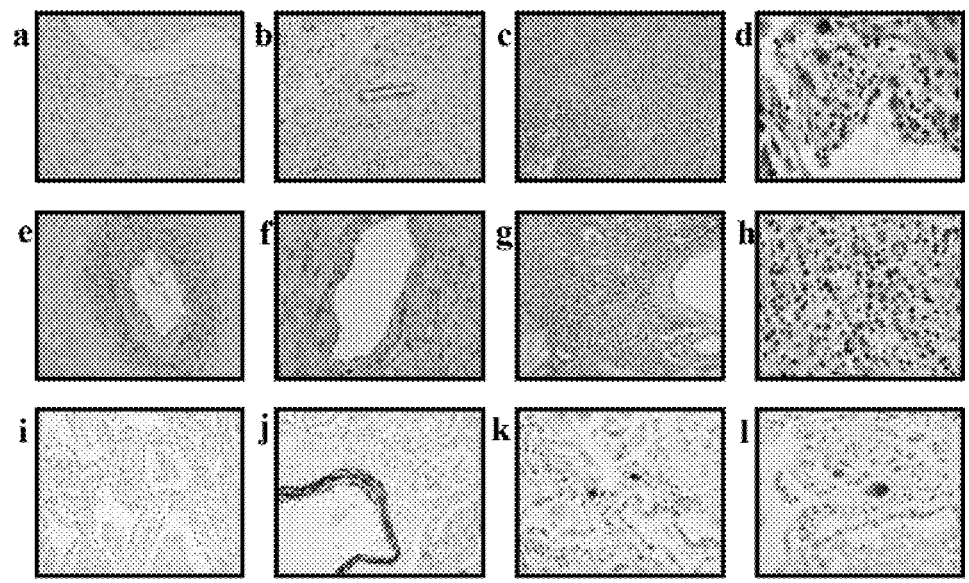
FIG. 1 shows: (A) Immunohistochemical detection of human cytomegalovirus (HCMV) proteins: (a) negative control (no primary antibody; objective lens ×10); (b) antismooth-muscle actin (mouse IgG2a mAb; ×10); (c) glioblastoma multiforme (GBM) specimen 1 stained with anti-HCMV IE1 (mouse IgG2a mAb, ×10); (d) higher magnification of anti-IE1 staining shows positive tumor cells and endothelial cells but negative lymphocytes and vascular intima (×20); (e) GBM specimen 2 stained with anti-HCMV IE1 showing staining of perivascular tumor cells but lack of detection in necrotic areas (×10); (0 perivascular tumor cells stained with anti-IE1 mAb (×20); (g and h) GBM specimen 3 stained with anti-HCMV pp65 mAb showing nuclear and perinuclear staining of tumor cells scattered throughout the GBM specimen (×10 and ×20, respectively); (i and j) CMV-infected lung stained with antismooth-muscle actin mAb (×10); (k) CMV-infected lung stained with anti-HCMV IE1 (×20); (l) CMV-infected lung stained with anti-HCMV pp65 mAb (×20); and (B) HCMV detection in matched GBM and normal brain. Representative histochemical sections from two GBM specimens containing areas of normal brain and tumor were stained for detection using isotype control antibodies (patient 1, left column), or anti-HCMV pp65 (patient 1 tumor, middle column; patient 2, right column). Focal areas of reactivity against the HCMV pp65 antibody was observed throughout the tumor-involved areas, but normal brain was devoid of immunoreactivity to the HCMV-specific antibodies (IE1 staining showed identical findings with more ubiquitous detection of IE1 in the tumor, not shown). All photographs taken at ×40 objective magnification.

Applicants have discovered that cells that express a CMV antigen can be targeted using CMV-specific immunological techniques including immunotherapy involving, for example, vaccines. The invention is applicable, but not limited, to the development of compositions, methods, and kits for diagnostics and therapies for cells that express a CMV antigen.

I. Definitions

The term "immune response" refers herein to any response to an antigen or antigenic determinant by the immune system. Exemplary immune responses include humoral immune responses (e.g. production of antigen-specific antibodies (neutralizing or otherwise)) and cell-mediated immune responses (e.g. lymphocyte proliferation).

II. Methods and Compositions

In one aspect, the present invention provides a method of eliciting in a subject an immune response to a cell that expresses a CMV antigen. The method comprises: administering to the subject a pharmaceutically acceptable composition comprising at least one CMV antigen, or nucleic acids encoding the at least one CMV antigen, wherein the pharmaceutically acceptable composition, when administered to the subject, elicits an immune response to the cell.

The cell that expresses a CMV antigen can be any type of cell. The cell can be characterized as a cancer cell, a precancerous cell, or a cell-type predisposed to developing cancer associated with CMV. The cancer includes but is not limited to brain cancers (e.g., gliomas), lung cancers, liver cancers, cervical cancers, soft tissue sarcomas, endocrine tumors, hematopoietic cancers, melanomas, bladder cancers, breast cancers, pancreatic cancers, prostate cancers, colon cancers, and ovarian cancers. The cancer also can be characterized as benign or malignant. In one embodiment, the cancer is a high grade glioma. In another embodiment, the high grade glioma is a glioblastoma multiforme, an anaplastic astrocytoma, or an oligodendroglioma.

Generally, the immune response can include the humoral immune response, the cell-mediated immune response, or both. For example, antigen presentation through an immunological pathway involving MHC II proteins or direct B-cell stimulation can produce a humoral response; and, antigens presented through a pathway involving MHC I proteins can elicit the cellular arm of the immune system.

A humoral response can be determined by a standard immunoassay for antibody levels in a serum sample from the subject receiving the pharmaceutically acceptable composition. A cellular immune response is a response that involves T cells and can be determined in vitro or in vivo. For example, a general cellular immune response can be determined as the T cell proliferative activity in cells (e.g., peripheral blood leukocytes (PBLs)) sampled from the subject at a suitable time following the administering of a pharmaceutically acceptable composition. Following incubation of e.g., PBMCs with a stimulator for an appropriate period, [$^3$H] thymidine incorporation can be determined. The subset of T cells that is proliferating can be determined using flow cytometry. T cell cytotoxicity (CTh) can also be determined.

In one embodiment, the immune response that is elicited is sufficient for prophylactic or therapeutic treatment of a neoplastic disease, or a symptom associated therewith, particularly cancer associated with CMV. Accordingly, a beneficial effect of the pharmaceutically acceptable composition will generally at least in part be immune-mediated, although an immune response need not be positively demonstrated in order for the compositions and methods described herein to fall within the scope of the present invention.

Administering to both human and non-human vertebrates is contemplated within the scope of the present invention. Veterinary applications also are contemplated. Generally, the subject is any living organism in which an immune response can be elicited. Examples of subjects include, without limitation, humans, livestock, dogs, cats, mice, rats, and transgenic species thereof.

The subject can either have a neoplastic disease (e.g., a tumor), or be at risk of developing the neoplastic disease. Subjects can be characterized by clinical criteria, for example, those with advanced neoplastic disease or high tumor burden exhibiting a clinically measurable tumor. A clinically measurable tumor is one that can be detected on the basis of tumor mass (e.g., by palpation, MRI, CAT scan, X-ray). Thus, for example, the pharmaceutically acceptable composition in accordance with the present invention can be administered to subjects with advanced disease with the objective of mitigating their condition. Preferably, a reduction in tumor mass occurs as a result of administering the pharmaceutically acceptable composition of the present invention, but any clinical improvement constitutes a benefit. Clinical improvement includes decreased risk or rate of progression or reduction in pathological consequences of a tumor, for example.

By way of another example, the subject can be one that has a history of cancer and has been responsive to another mode of therapy. The other therapy may have included e.g., surgical resection, radiotherapy, chemotherapy, and other modes of immunotherapy whereby as a result of the other therapy, the subject presents no clinically measurable tumor. However, the subject can be one determined to be at risk for recurrence or progression of the cancer, either near the original tumor site, or by metastases. Such subjects can be further categorized as high-risk and low-risk subjects. The subdivision can be made on the basis of features observed before or after the initial treatment. These features are known in the clinical arts, and are suitably defined for each different cancer. Features typical of high risk subgroups are those in which the tumor has invaded neighboring tissues, or which show involvement of lymph nodes. Thus, for example, a pharmaceutically acceptable composition of the present invention can be administered to the subject to elicit an anti-cancer response primarily as a prophylactic measure against recurrence. Preferably, administering the composition delays recurrence of the cancer, or more preferably, reduces the risk of recurrence (i.e., improves the cure rate). Such parameters can be determined in comparison with other patient populations and other modes of therapy.

The pharmaceutically acceptable composition can be administered at any time that is appropriate. For example, the administering can be conducted before or during traditional therapy of a subject having a tumor burden, and continued after the tumor becomes clinically undetectable. The administering also can be continued in a subject showing signs of recurrence.

The pharmaceutically acceptable composition can be administered in a therapeutically or a prophylactically effective amount, wherein the pharmaceutically acceptable composition comprises the at least one CMV antigen, or nucleic acids encoding the at least one CMV antigen, either alone or in combination with one or more other antigens. Administering the pharmaceutically acceptable composition of the present invention to the subject can be carried out using known procedures, and at dosages and for periods of time sufficient to achieve a desired effect. For example, a therapeutically or prophylactically effective amount of the pharmaceutically acceptable composition, can vary according to factors such as the age, sex, and weight of the subject. Dosage regima can be adjusted by one of ordinary skill in the art to elicit the desired immune response including immune responses that provide therapeutic or prophylactic effects.

The pharmaceutically acceptable composition can be administered to the subject at any suitable site, for example a site that is distal to or proximal to a primary tumor. The route of administering can be parenteral, intramuscular, subcutaneous, intradermal, intraperitoneal, intranasal, intravenous (including via an indwelling catheter), via an afferent lymph vessel, or by any other route suitable in view of the neoplastic disease being treated and the subject's condition. Preferably, the dose will be administered in an amount and for a period of time effective in bringing about a desired response, be it eliciting the immune response or the prophylactic or therapeutic treatment of the neoplastic disease and/or symptoms associated therewith.

The pharmaceutically acceptable composition can be given subsequent to, preceding, or contemporaneously with other therapies including therapies that also elicit an immune response in the subject. For example, the subject may previously or concurrently be treated by chemotherapy (e.g., by an alkylating agent such as temozolomide), radiation therapy, and other forms of immunotherapy, such other therapies preferably provided in such a way so as not to interfere with the immunogenicity of the compositions of the present invention.

Administering can be properly timed by the care giver (e.g., physician, veterinarian), and can depend on the clinical condition of the subject, the objectives of administering, and/or other therapies also being contemplated or administered. In some embodiments, an initial dose can be administered, and the subject monitored for either an immunological or clinical response, preferably both. Suitable means of immunological monitoring include using patient's peripheral blood lymphocyte (PBL) as responders and neoplastic cells as stimulators. An immunological reaction also can be determined by a delayed inflammatory response at the site of administering.

One or more doses subsequent to the initial dose can be given as appropriate, typically on a monthly, semimonthly, or preferably a weekly basis, until the desired effect is achieved. Thereafter, additional booster or maintenance doses can be given as required, particularly when the immunological or clinical benefit appears to subside.

A. CMV Antigens

In one embodiment, the at least one CMV antigen is a polypeptide, or an immunogenic fragment thereof, encoded by a CMV gene. As indicated above, the term "CMV," as used herein, includes any strain of the virus that infects an animal, for example mammals such as humans and monkeys. Strains of CMV that infect humans are typically designated as human CMV (HCMV). ORFs and/or their corresponding polypeptides from HCMV can be referred to using nomenclature as described by, for example, Chee et al., Curr. Top. Microbiol. Immunol., 154:125 (1990) and Spaete et al., J. General Virology, 74:3287 (1994), each of which is incorporated herein by reference for their teaching of such polypeptides and their nomenclature. Reference to such reading frames and polypeptides from CMV also can refer to corresponding sequence and positional homologs found in different strains, including sequences in any naturally occurring CMV strain, and mutations to such strains as well as splice variants.

Gene sequences as well as ORFs and encoded polypeptides of different strains of CMV are known in the art including, without limitation, HCMV AD169 (American Type Culture Collection (ATCC) #VR 538), HCMV Towne (ATCC #VR 977), HCMV Davis (ATCC #VR 807), HCMV Toledo (Quinnan et al, Ann. Intern. Med., 101: 478-83 (1984)), monkey CMV Rh68.1 (ATCC #VR 677), monkey CMV CSG (ATCC #VR 706), rat CMV Priscott (ATCC #VR 991), and mouse CMV Smith (ATCC #VR 1399). By way of a another example, gene and polypeptide sequence information of HCMV AD169 strain also is described by GENBANK Accession Nos. BK000394.2 and X17403.1, each of which is incorporated herein by reference in its entirety. Also, known sequence information corresponding to one CMV strain (e.g., HCMV AD169 strain) can be used to determine sequence information of genes and polypeptides of another CMV strain. For example, homologs can be determined that includes genes sharing a common evolutionary origin, structure/function, and the products of which encode polypeptides having amino acid sequence identity of at least about 20%, illustratively, about 20 to about 100%, about 30 to about 90%, about 40 to about 80%, about 50 to about 70% sequence identity. A homolog can be identified by methods known in the art such as comparison of the nucleic acid or amino acid sequences to each other using computer programs, such as BLAST, or by hybridization under stringencies which are designed to detect a predetermined amount of mismatch between the sequences. Also, sequence information based on homology can be employed to isolate and characterize sequences of a particular isolate, for example using primers and polymerase chain reaction (PCR).

In some embodiments, the at least one CMV antigen is a polypeptide, or an immunogenic fragment thereof, encoded by an open reading frame (ORF) of a HCMV gene or a homolog thereof. In one embodiment, the polypeptide, or the immunogenic fragment thereof, is encoded by a gene corresponding to the CMV strain shown by GENBANK Accession No. BK000394.2 or X17403.1.

In other embodiments, the at least one CMV antigen corresponds to a polypeptide, or an immunogenic fragment thereof, selected from the group consisting of: phosphoprotein unique long 83 (ppUL83; a/k/a pp65), glycoprotein UL55 (gpUL55; a/k/a gB), UL123 immediate early 1 (IE1) protein, UL122 IE2 protein, UL111A (a/k/a mtrII), US28, ppUL32, ppUL65, ppUL80a, ppUL82, ppUL98a, ppUL99, gpUL4 (a/k/a gp48), gpUL16, gpUL18 (a/k/a MHC), gpUL75 (a/k/a gH), gpUL100, gpUL110 (a/k/a gM), gpUL115 (a/k/a gL), pUL46, pUL48, pUL56, pUL86 (a/k/a MCP), glycoprotein unique short 10 (gpUS10), gpUS11, glycoprotein complex II (gcII), gp65, and gp93.

In one embodiment, the at least one CMV antigen comprises an amino acid sequence corresponding to one or more epitopes from the same antigen or distinct antigens of CMV. In some embodiments, the one or more epitopes can be characterized as restricted to or not restricted to a single MHC Class I haplotype. In other embodiments, the one or more epitopes is specific for a sufficient number of MHC Class 1 molecules to provide coverage for at least about 5% of the general population, illustratively, for at least about 5, 10, 20, 30, 40, 50, 60, 70, 80, 90, and 100% of the general population, irrespective of racial origin or ethnicity. Those skilled in the art will readily be in a position to determine the number of individual HCMV cytotoxic T lymphocytes (CTL) epitopes required to provide coverage of any given population using HLA specificity experimentation. Optionally, the one or more epitopes further display HLA supertype specificity and/or comprise one or more CD4+ determinants sufficient to facilitate a T-helper function in a subject.

Examples of CMV epitopes include, without limitation, the peptides comprising the amino acid sequences as described by Trivedi et al., Blood, 105:2793 (2005) and U.S. Patent Application Publication No. 2005/0019344, each of which is incorporated herein by reference for their teaching of CMV epitopes. In one embodiment, the at least one CMV antigen is a polypeptide, or an antigenic fragment thereof, comprising an amino acid sequence of SEQ ID NO:1, 2, or 3.

In another embodiment, the at least one antigen comprises one or more CMV CTL epitopes restricted through dominant HLA alleles. For example, a vaccination strategy can involve the generation of CD8+ T-cell repertoire with formulations of synthetic peptides that mimic immunodominant epitopes known to be recognized by a CMV-induced CTL response, for example by mixing multiple peptides or, alternatively, by using minimal CTL epitopes that can be fused to construct a recombinant or synthetic polyepitope polypeptide. Also, a vaccine design based on CTL epitopes from latent antigens can be directed against CMV-transformed latently infected cells as well as also be used in CMV-seronegative transplant recipients because of their increased susceptibility to CMV virus-induced conditions.

In other embodiments, the at least one antigen corresponds to a pool of peptides. In one embodiment, the pool of peptides comprises at least about 8-mer amino acid sequences, illustratively, about 8-mers to about 30-mers, about 9-mers to about 25-mers, about 10-mers to about 20-mers, about 11-mers to about 18-mers, about 12-mers to about 16-mers, and about 13-mers to about 15-mers, wherein the sequences of the peptides have at least about 6 amino acids overlap, illustratively, about 6 to about 20, about 7 to about 19, about 8 to about 18, about 9 to about 17, about 10 to about 16, and about 11 to about 14 amino acids overlap, wherein the pool of peptides covers at least about 10% of an HCMV protein, illustratively, about 10 to about 100%, about 20 to about 90%, about 30 to about 80%, about 40 to about 70%, and about 50 to about 60% of the HCMV protein.

In one embodiment, the HCMV protein is an IE-1 protein (e.g., IE-1 protein of HCMV strain AD169; see, e.g., Swiss-Prot Acc. No. P13202, which is herein incorporated by reference in its entirety). In another embodiment, the HCMV protein is a pp65 protein (e.g., pp65 protein of HCMV strain AD169; see, e.g., Swiss-Prot Acc. No. P06725, which is herein incorporated by reference in its entirety).

In other embodiments, the pool of peptides comprises 15-mer amino acid sequences of 11 amino acids overlap, covering the complete or substantially complete sequence of one or more HCMV proteins. In some embodiment, the one or more HCMV proteins is an IE-1 protein or a pp65 protein. For example, in some embodiments, the pool of peptides comprises PepTivator™ CMV pp65 (Miltenyi Biotec, Gladbach, Germany) or PepTivator™ CMV IE-1 (Miltenyi Biotec, Gladbach, Germany).

In some embodiments, the use of peptide epitopes can make it easier to prepare products at current Good Manufacturing Practice (cGMP) grade. Thus, in some embodiments, the present invention provides an immunogenic composition comprising the pool of peptides.

Accordingly, in some aspects, the present invention provides one or more immunologically active peptides, and functional variants thereof, capable of eliciting a cellular immune response to a cell that expresses a CMV antigen. For example, the cell can be the cell can be characterized as a cancer cell, a precancerous cell, or a cell-type predisposed to developing cancer associated with CMV. In some embodiments, the peptides are capable of directing human CTL to recognize and lyse the cells. Such immunologically active peptides, in association with an MHC Class I molecule, can be recognized by CTL of individuals having a latent or active HCMV infection.

Such a peptide(s) (e.g., the pool of peptides) may be administered in the form of a peptide(s) or lipopeptide(s) vaccine, optionally with an adjuvant. In some embodiments, the peptide(s) may be administered in the form of a cellular vaccine via the administration of autologous or allogeneic antigen presenting cells or dendritic cells that have been treated in vitro so as to present a peptide of the pool on their surface. In another embodiment, T cells can be removed from an individual and treated in vitro with the peptide(s), wherein the resulting CTL are reinfused autologously or allogeneically to the subject. In various other embodiments, the peptide(s) of the present invention also may be administered to the subject, or in vitro to T cells, in the form of a polynucleotide vaccine, wherein one or more suitable gene transfer vectors, such as a plasmid or an engineered viral vector that contains DNA encoding the peptide fragment(s) under the control of appropriate expression regulatory sequences, is administered to the subject or to T cells in vitro.

Pools of peptides are disclosed by, e.g., Kiecker et al., Hum Immunol. 65:523-36 (2204), which is herein incorporated by reference for its teaching of pools of peptides and using pools of peptides for stimulating T cells.

The at least one CMV antigen also can be determined by routine experimentation using techniques known in the art. For example, antigenic determinants of a particular CMV strain recognized by the immune system can be cloned and characterized using libraries and expression vectors. By way of example, random fragments of DNA can be generated from a cosmid library of HCMV DNA. Fragments of various lengths, e.g., about 50 to 600 bp in length, can be selected and cloned into open reading frame (ORF) expression vectors to create ORF-libraries that represent either the entire viral genome or defined subregions. Clones be isolated and screened immunologically for the synthesis of fusion proteins consisting of an antigenic peptide encoded by the CMV sequence coupled to a reporter, e.g., an E. coli beta-galactosidase molecule. Anti-CMV sera raised in animals as well as human hyperimmune globulin can be used for colony screening. Distinct sets of antigenic fusion proteins can be recognized by different antisera. Clones giving strong reactions with immune sera can be mapped on the CMV genome and the sequences of the CMV inserts determined. Antibodies against fusion proteins can be raised in mice or rabbits to identify the corresponding CMV proteins.

In other embodiments, the at least one CMV antigen further comprises one or more signal sequences, for example, but not limited to, a gp96 endoplasmic reticulum targeting peptide signal sequence, a LAMP-1 lysosomal targeting peptide signal sequence, and the like. Signal sequences can enhance MHC class I and class II antigen processing and presentation as well as provide other targeting properties. In other embodiments, the at least one CMV antigen can be conjugated to a carrier protein (e.g., Keyhole Limpet Hemocyanin (KLH), or synthesized as fusion proteins through recombination of nucleic acid coding sequences.

As further illustrated below, the pharmaceutically acceptable composition can comprise the at least one CMV antigen or nucleic acids encoding the at least one CMV antigen.

A. Nucleic Acids

Generally, the subject can be inoculated with the pharmaceutically acceptable composition comprising nucleic acids through any parenteral route. For example, the subject can be inoculated by intravenous, intraperitoneal, intradermal, subcutaneous, inhalation, or intramuscular routes, or by particle bombardment using a gene gun. Preferably, muscle tissue can be a site for the delivery and expression of polynucleotides. A dose of polynucleotides can be administered into muscle by multiple and/or repetitive injections, for example, to extend administration over long periods of time. Thus, muscle cells can be injected with polynucleotides coding for the at least one CMV antigen, and the expressed antigens can be presented by muscle cells in the context of antigens of the major histocompatibility complex to elicit the immune response against the at least one CMV antigen.

The epidermis can be another useful site for the delivery and expression of polynucleotides, for example either by direct injection or particle bombardment. A dose of polynucleotides can be administered in the epidermis, for example by multiple injections or bombardments to extend administering over long periods of time. For example, skin cells can be injected with polynucleotides coding for the at least one CMV antigen, and the expressed antigens can be presented by skin cells in the context of antigens of the major histocompatibility complex to elicit the immune response against the at least one CMV antigen.

A subject also can be inoculated by a mucosal route. The polynucleotides can be administered to a mucosal surface by a variety of methods including polynucleotide-containing nose-drops, inhalants, suppositories, microsphere-encapsulated polynucleotides, or by bombardment with polynucleotide-coated gold particles. For example, the nucleic acids coding for the at least one CMV antigen can be administered to a respiratory mucosal surface.

Any appropriate physiologically compatible medium, such as saline for injection, or gold particles for particle bombardment, is suitable for introducing polynucleotides into a subject.

1. RNA

In some embodiments, the pharmaceutically acceptable composition comprises nucleic acids encoding the at least one CMV antigen, wherein the nucleic acids are RNA. The RNAs comprise translatable RNA templates to guide the intracellular synthesis of amino acid chains that provide the at least one CMV antigen. RNAs encoding the at least one CMV antigen also can be in vitro transcribed, e.g., reverse transcribed to produce cDNAs that can then be amplified by PCR, if desired, and subsequently transcribed in vitro, with or without cloning the cDNA. A number of methods are available to one of ordinary skill in the art to prepare RNAs encoding the at least one CMV antigen. Thus, for example, conventional in vitro transcription techniques and bacterial polymerases can be used to produce in vitro transcribed RNAs, or the in vitro transcribed RNAs can be synthesized from cloned DNA sequences encoding the at least one CMV antigen.

2. DNA

In another embodiment, the nucleic acids encoding the at least one CMV antigen comprise DNAs having open reading frames encoding the at least one CMV antigen. For example, a pharmaceutically acceptable composition comprising expression vectors having DNA open reading frames encoding the at least one CMV antigen can be administered to the subject.

Genomic DNA fragments and/or cDNAs comprising open reading frames encoding the at least one CMV antigen can be employed in the methods of the present invention. cDNAs can be prepared from the above-described RNAs coding for the at least one CMV antigen using techniques known to one of ordinary skill in the art. If desired, DNA can be fragmented, for example by physical fragmentation or, preferably, by enzymatic cleavage, i.e. use of restriction endonucleases. Fragmentation methods are well known to those skilled in the art and can be varied (e.g., by use of different restriction endonucleases or combinations and digestion times) to obtain fragments differing in size and composition. DNAs or fragments thereof having open reading frames encoding the at least one CMV antigen can be cloned into expression vectors by methods and reagents known in the art.

Standard cloning vectors can be employed that have a selectable marker (e.g., ampicillin) and, preferably an origin of replication (e.g., ori) and a suitable promoter. Bacteria (e.g., *E. coli*) or other suitable host can then transformed with the vectors, and transformants cultured by standard procedures and the plasmid DNA isolated by such methods as chromatographic or organic separation. For example, plasmids are available for cloning into a site which can direct the at least one CMV antigen expressed by the open reading frames to MHC I or II. Expression vectors used for eliciting an immune response and methods of using same are described in U.S. Patent Application Publication No. 20040241140, which is incorporated herein for its teaching of expression vectors used for eliciting an immune response and methods of using same.

When taken up by a cell (e.g., muscle cell, an antigen-presenting cell (APC) such as a dendritic cell, macrophage, etc.), a DNA molecule can be present in the cell as an extra-chromosomal molecule and/or can integrate into the chromosome. DNA can be introduced into cells in the form of a plasmid which can remain as separate genetic material. Alternatively, linear DNAs that can integrate into the chromosome can be introduced into the cell. Optionally, when introducing DNA into a cell, reagents which promote DNA integration into chromosomes can be added.

Thus, preferably DNAs include regulatory elements necessary for expression of an open reading frame. Such elements can include, for example, a promoter, an initiation codon, a stop codon, and a polyadenylation signal. In addition, enhancers can be included. As is known in the art, these elements are preferably operably linked to a sequence that encodes the at least one CMV antigen. Regulatory elements are preferably selected that are operable in the species of the subject to which they are to be administered. Initiation codons and stop codons in frame with a coding sequence are preferably included.

Examples of promoters include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metalothionein. Examples of suitable polyadenylation signals include but are not limited to SV40 polyadenylation signals and LTR polyadenylation signals.

In addition to the regulatory elements required for DNA expression, other elements may also be included in the DNA molecule. Such additional elements include enhancers. Enhancers include the promoters described hereinabove. Preferred enhancers/promoters include, for example, human actin, human myosin, human hemoglobin, human muscle creatine and viral enhancers such as those from CMV, RSV and EBV.

Optionally, the DNAs can be operably incorporated in a carrier or delivery vector. Useful delivery vectors include but are not limited to biodegradable microcapsules, immuno-stimulating complexes (ISCOMs) or liposomes, and genetically engineered attenuated live carriers such as viruses or bacteria.

In some embodiments, the vector is a viral vector, such as lentiviruses, retroviruses, herpes viruses, adenoviruses, adeno-associated viruses, vaccinia viruses, baculoviruses, Fowl pox, AV-pox, modified vaccinia Ankara (MVA) and other recombinant viruses. For example, a vaccinia virus vector can be used to infect dendritic cells.

Thus, a vector encoding the at least one CMV antigen or an immunogenic fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both.

Viral vectors commonly used for in vivo or ex vivo targeting and vaccination procedures are DNA-based vectors and retroviral vectors. Methods for constructing and using viral vectors are known in the art (see, e.g., Miller and Rosman, BioTechniques, 7:980-990, 1992). Preferably, the viral vectors are replication defective, i.e., they are unable to replicate autonomously in the target cell. Preferably, the replication defective virus is a minimal virus, i.e., it retains only the sequences of its genome which are necessary for encapsidating the genome to produce viral particles.

DNA viral vectors include an attenuated or defective DNA virus, such as but not limited to herpes simplex virus (HSV), papillomavirus, Epstein Barr virus (EBV), adenovirus, adeno-associated virus (AAV), vaccinia virus, and the like. Examples of particular vectors include, but are not limited to, a defective herpes virus 1 (HSV1) vector (Kaplitt, et al., Molec. Cell. Neurosci. 2:320-330, 1991; International Patent Publication No. WO 94/21807, published Sep. 29, 1994; International Patent Publication No. WO 92/05263, published Apr. 2, 1994); an attenuated adenovirus vector, such as the vector described by Stratford-Perricaudet, et al. (J. Clin. Invest. 90:626-630, 1992; see also La Salle, et al., Science 259:988-990, 1993); and a defective adeno-associated virus vector (Samulski, et al., J. Virol. 61:3096-3101, 1987; Samulski, et al., J. Virol. 63:3822-3828, 1989; Lebkowski, et al., Mol. Cell. Biol. 8:3988-3996, 1988). Viral vectors also are commercially available.

Optionally, the DNAs also can be provided with reagents that improve the uptake of the genetic material by cells. For example, the DNA can be formulated with or administered in conjunction with an uptake facilitator reagent selected from the group consisting of benzoic acid esters, anilides, amidines, and urethans.

B. Dendritic Cells

One of ordinary skill in the art will recognize that the capacity to generate dendritic cells (DCs) in vitro also can be used in accordance with the present invention for ex vivo loading of DCs with the at least one CMV antigen, or nucleic acids encoding the at least one CMV antigen, and administration of DC vaccines as a strategy for eliciting an immune response to a cell that expresses a CMV antigen. Preclinical studies have shown DCs to be potent activators of de novo and recall responses in B and T lymphocytes.

In some embodiments, the present invention provides a method for eliciting in a subject an immune response to a cell that expresses a CMV, the method comprising administering to the subject a pharmaceutically acceptable composition comprising dendritic cells loaded ex vivo with at least one CMV antigen, or nucleic acids encoding the at least one CMV antigen, wherein the pharmaceutically acceptable composition, when administered to the subject, elicits the immune response to the cell.

Accordingly, the CMV antigen-primed antigen-presenting cells of the present invention and the CMV antigen-specific T lymphocytes generated with these antigen-presenting cells can be used as active compounds in immunomodulating compositions for prophylactic or therapeutic applications. As described below, in some embodiments, the antigen-primed antigen-presenting cells of the invention can be used for generating cytotoxic T lymphocytes (CTL) (e.g., CD8+ or CD4+ CTL) for adoptive transfer to the subject.

C. Compositions

In other aspects, the present invention provides a pharmaceutically acceptable composition comprising at least one CMV antigen or nucleic acids encoding the at least one CMV antigen. The pharmaceutically acceptable composition, when administered to a subject, can elicit an immune response against a cell that expresses a CMV antigen. The pharmaceutically acceptable compositions of the present invention can be useful as vaccine compositions for prophylactic or therapeutic treatment of a neoplastic disease or symptoms thereof, particularly for preventing or treating CMV-associated cancer (e.g., a tumor) in the subject.

In some embodiments, the pharmaceutically acceptable composition further comprises a physiologically acceptable carrier, diluent, or excipient. Techniques for formulating and administering also can be found in Remington's Pharmaceutical Sciences, Mack Publishing Co., Easton, Pa., latest edition.

Pharmaceutically acceptable carriers known in the art include, but are not limited to, sterile water, saline, glucose, dextrose, or buffered solutions. Agents such as diluents, stabilizers (e.g., sugars and amino acids), preservatives, wetting agents, emulsifying agents, pH buffering agents, additives that enhance viscosity, and the like. Preferably, the medium or carrier will produce minimal or no adverse effects.

In other embodiments, the pharmaceutically acceptable composition further comprises a physiologically acceptable adjuvant. Preferably, the adjuvant employed provides for increased immunogenicity. The adjuvant can be one that provides for slow release of antigen (e.g., the adjuvant can be a liposome), or it can be an adjuvant that is immunogenic in its own right thereby functioning synergistically with antigens. For example, the adjuvant can be a known adjuvant or other substance that promotes nucleic acid uptake, recruits immune system cells to the site of administration, or facilitates the immune activation of responding lymphoid cells. Adjuvants include, but are not limited to, immunomodulatory molecules (e.g., cytokines), oil and water emulsions, aluminum hydroxide, glucan, dextran sulfate, iron oxide, sodium alginate, Bacto-Adjuvant, synthetic polymers such as poly amino acids and co-polymers of amino acids, saponin, paraffin oil, and muramyl dipeptide.

In one embodiment, the adjuvant is an immunomodulatory molecule. For example, the immunomodulatory molecule can be a recombinant protein cytokine, chemokine, or immunostimulatory agent or nucleic acid encoding cytokines, chemokines, or immunostimulatory agents designed to enhance the immunologic response.

Examples of immunomodulatory cytokines include interferons (e.g., IFNα, IFNβ and IFNγ), interleukins (e.g., IL-1, IL-2, IL-3, IL-4, IL-5, IL-6, IL-7, IL-8, IL-9, IL-10, IL-12 and IL-20), tumor necrosis factors (e.g., TNFα and TNFβ), erythropoietin (EPO), FLT-3 ligand, gIp10, TCA-3, MCP-1, MIF, MIP-1α, MIP-1β, Rantes, macrophage colony stimulating factor (M-CSF), granulocyte colony stimulating factor (G-CSF), and granulocyte-macrophage colony stimulating factor (GM-CSF), as well as functional fragments of any of the foregoing. Any immunomodulatory chemokine that binds to a chemokine receptor, i.e., a CXC, CC, C, or CX3C chemokine receptor, also can be used in the context of the present invention. Examples of chemokines include, but are not limited to, Mip1α, Mip-1β, Mip-3α (Larc), Mip-3β, Rantes, Hcc-1, Mpif-1, Mpif-2, Mcp-1, Mcp-2, Mcp-3, Mcp-4, Mcp-5, Eotaxin, Tarc, Elc, I309, IL-8, Gcp-2 Gro-α, Gro-β, Gro-γ, Nap-2, Ena-78, Gcp-2, Ip-10, Mig, I-Tac, Sdf-1, and Bca-1 (Blc), as well as functional fragments of any of the foregoing.

In another embodiment, the adjuvant is a cytokine selected from the group consisting of: GM-CSF, G-CSF, IL-2, IL-4, IL-7, IL-12, IL-15, IL-21, TNF-α, and M-CSF. In some embodiments, the adjuvant is comprised of incomplete Freund's adjuvant (Montanide ISA 51) or *Corynebacterium granulosum* P40.

One of ordinary skill in the art will appreciate that some of these adjuvants cannot be expressed from a vector, in which case the adjuvant, when used, can be administered simultaneously or sequentially, in any order.

One of ordinary skill in the art knows that methods and compositions of the present invention can be used as part of combination therapies, for example as methods and/or compositions comprising one or more other agents such as, but not limited to, chemotherapeutic, immunotherapeutic, immunomodulatory, anti-angiogenic, anti-viral agents, and hormonal agents.

Examples of anti-viral agents include, but are not limited, a ganciclovir (e.g., CYTOVENE®), a valganciclovir (e.g., Valcyte®), a foscarnet (e.g., FOSCAVIR®), a cidofovir (e.g., VISTIDE®, HPMPC), an adefovir (e.g., PMEA, PREVEON®, HEPSERA®), an acyclovir (e.g., ZOVIRAX®), a valacyclovir (e.g., VALTREX™, ZELITREX™), a polyanion, and a protein kinase C inhibitor (e.g., a bis-indolylmaleide). In one embodiment, the anti-viral agent employed in combination with the compositions and methods of the present invention is a ganciclover, a valganciclovir, a cidofovir, or a foscarnet.

In other embodiments, the one or more other agents effect CMV antigen expression, preferably by enhancing CMV antigen expression, preferably by enhancing CMV antigen expression in latently infected cells, preferably in glioma cells. In one embodiment, the one or more agents is selected from the group consisting of: a retinoic acid (RA), alemtuzumb (Campath 1H), and an immunosuppressive agent (e.g., cyclophosphamide, cyclosporine). In another embodiment, irradiation and/or immunodeletion is provided in combination with the compositions and methods of the present invention.

In various embodiments, the one or more other agents can be a chemotherapeutic agent, naturally occurring or synthetic, for example as described in "Cancer Chemotherapeutic Agents", American Chemical Society, 1995, W. O. Foye Ed.

In one embodiment, the chemotherapeutic agent is selected from the group consisting of a small molecule receptor antagonists such as vatalanib, SU 11248 or AZD-6474, EGFR or HER2 antagonists such as gefitinib, erlotinib, CI-1033 or Herceptin, antibodies such as bevacizumab, cetuximab, rituximab, DNA alkylating drugs such as cisplatin, oxaliplatin or carboplatin, anthracyclines such as doxorubicin or epirubicin, an antimetabolite such as 5-FU, pemetrexed, gemcitabine or capecitabine, a camptothecin such as irinotecan or topotecan, an anti-cancer drug such as paclitaxel or docetaxel, an epipodophyllotoxin such as etoposide or teniposide, a proteasome inhibitor such as bortezomib or anti-inflammatory drugs such as celecoxib or rofecoxib, optionally in form of the pharmaceutically acceptable salts, in form of the hydrates and/or solvates and optionally in the form of the individual optical isomers, mixtures of the individual enantiomers or racemates thereof.

In another embodiment, the chemotherapeutic agent is selected from the group consisting of a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, an antagonist of the mitogen-activated protein kinase such as BAY-43-9006 or BAY-57-9006, a quinazoline derivative such as 4-[(3-chloro-4-fluorophenyl)amino]-6-{[4-(N,N-dimethylamino)-1-oxo-2-bute-n-1-yl]amino}-7-((S)-tetrahydrofuran-3-yloxy) quinazoline or 4-[(3-chloro-4-fluoro-phenyl)amino]-6-{[4-(homomorpholin-4-yl)-1-oxo-2-bu-ten-1-yl]amino}-7-[(S)-(tetrahydrofuran-3-yl)oxy]-quinazoline, or a pharmaceutically acceptable salt thereof, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, a protein tyrosine kinase inhibitor which is a fusion protein such as VEGFtrap, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an ethyleneimine compound, an alkylsulphonate, daunorubicin, doxorubicin (adriamycin), liposomal doxorubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), pemetrexed, tegafur/uracil, uracil mustard, fludarabine, gemcitabine, capecitabine, mercaptopurine, cladribine, thioguanine, methotrexate, pentostatin, hydroxyurea, or folic acid, a phleomycin, a bleomycin or a derivative or salt thereof, CHPP, BZPP, MTPP, BAPP, liblomycin, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, an anti-cancer drug from plants such as paclitaxel (taxol), docetaxel or taxotere, a vinca alkaloid such as navelbine, vinblastin, vincristin, vindesine or vinorelbine, a tropolone alkaloid such as colchicine or a derivative thereof, a macrolide such as maytansine, an ansamitocin or rhizoxin, an antimitotic peptide such as phomopsin or dolastatin, an epipodophyllotoxin or a derivative of podophyllotoxin such as etoposide or teniposide, a steganacin, an antimitotic carbamate derivative such as combretastatin or amphetinile, procarbazine, a proteasome inhibitor such as bortezomib, an enzyme such as asparaginase, pegylated asparaginase (pegaspargase) or a thymidine-phosphorylase inhibitor, a gestagen or an estrogen such as estramustine (T-66) or megestrol, an anti-androgen such as flutamide, casodex, anandron or cyproterone acetate, an aromatase inhibitor such as aminogluthetimide, anastrozole, formestan or letrozole, a GNrH analogue such as leuprorelin, buserelin, goserelin or triptorelin, an anti-estrogen such as tamoxifen or its citrate salt, droloxifene, trioxifene, raloxifene or zindoxifene, a derivative of 17β-estradiol such as ICI 164,384 or ICI 182,780, aminoglutethimide, formestane, fadrozole, finasteride, ketoconazole, a LH-RH antagonist such as leuprolide, a steroid such as prednisone, prednisolone, methylprednisolone, dexamethasone, budenoside, fluocortolone or triamcinolone, an interferon such as interferon β, an interleukin such as IL-10 or IL-12, an anti-TNFα antibody such as etanercept, an immunomodulatory drug such as thalidomide, its R- and S-enantiomers and its derivatives, or revimid (CC-5013), a leukotrien antagonist, mitomycin C, an aziridoquinone such as BMY-42355, AZQ or EO-9, a 2-nitroimidazole such as misonidazole, NLP-1 or NLA-1, a nitroacridine, a nitroquinoline, a nitropyrazoloacridine, a "dual-function" nitro aromatic such as RSU-1069 or RB-6145, CB-1954, a N-oxide of nitrogen mustard such as nitromin, a metal complex of a nitrogen mustard, an anti-CD3 or anti-CD25 antibody, a tolerance induction agent, a biphosphonate or derivative thereof such as minodronic acid or its derivatives (YM-529, Ono-5920, YH-529), zoledronic acid monohydrate, ibandronate sodium hydrate or clodronate disodium, a nitroimidazole such as metronidazole, misonidazole, benznidazole or nimorazole, a nitroaryl compound such as RSU-1069, a nitroxyl or N-oxide such as SR-4233, an halogenated pyrimidine analogue such as bromodeoxyuridine, iododeoxyuridine, a thiophosphate such as WR-272 1, a photo-chemically activated drug such as porfimer, photofrin, a benzoporphyrin derivative, a pheophorbide derivative, merocyanin 540 (MC-540) or tin etioporpurin, an ant-template or an anti-sense RNA or DNA such as oblimersen, a non-steroidal inflammatory drug such as acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lomoxicam, nimesulide, meloxicam, celecoxib, rofecoxib, or a pharmaceutically acceptable salt of a non-steroidal inflammatory drug, a cytotoxic antibiotic, an antibody targeting the surface molecules of cancer cells such as apolizumab or 1D09C3, an inhibitor of metalloproteinases such as TIMP-1 or TIMP-2, Zinc, an inhibitor of oncogenes such as P53 and Rb, a complex of rare earth elements such as the heterocyclic complexes of lanthanides, a photo-chemotherapeutic agent such as PUVA, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, or a therapeutic agent selected from IM-842, tetrathiomolybdate, squalamine, combrestatin A4, TNP-470, marimastat, neovastat, bicalutamide, abarelix, oregovomab, mitumomab, TLK-286, alemtuzumab, ibritumomab, temozolomide, denileukin diftitox, aldesleukin, dacarbazine, floxuridine, plicamycin, mitotane, pipobroman, plicamycin, tamoxifen and testolactone. Preferred compounds include small molecule VEGF receptor antagonist such as vatalanib (PTK-787/ZK222584), SU-5416, SU-6668, SU-11248, SU-14813, AZD-6474, EGFR/HER2 antagonists such as CI-1033 or GW-2016, an EGFR antagonist such as iressa (gefitinib, ZD-1839), tarceva (erlotinib, OSI-774), PKI-166, EKB-569, HKI-272 or herceptin, an antagonist of the mitogen-activated protein kinase such as BAY-43-9006 or BAY-57-9006, atrasentan, rituximab, cetuximab, Avastin™ (bevacizumab), IMC-1C11, erbitux (C-225), DC-101, EMD-72000, vitaxin, imatinib, an alkylating agent or a platinum compound such as melphalan, cyclophosphamide, cisplatin, carboplatin, oxaliplatin, satraplatin, daunorubicin, doxorubicin (adriamycin), liposomal doxorubicin (doxil), epirubicin, idarubicin, a pyrimidine or purine analogue or antagonist or an inhibitor of the nucleoside diphosphate reductase such as cytarabine, 5-fluorouracile (5-FU), pemetrexed, tegafur/uracil, gemcitabine, capecitabine, mercaptopurine, methotrexate, an anti-cancer drug such as paclitaxel (taxol) or docetaxel, a vinca alkaloid such as navelbine, vinblastin, vincristin, vindesine or vinorelbine, an antimitotic peptide such as dolastatin, an epipodophyllotoxin or a derivative of podophyllotoxin such as etoposide or teniposide, a non-steroidal inflammatory drug such as meloxicam, celecoxib, rofecoxib, an antibody targeting the surface molecules of cancer cells such as apolizumab or ID09C3 or the heat shock protein HSP90 modulator geldanamycin and its derivative 17-allylaminogeldanamycin or 17-AAG.

In another embodiment, the chemotherapeutic agent is selected from the group consisting of compounds interacting with or binding tubulin, synthetic small molecule VEGF receptor antagonists, small molecule growth factor receptor antagonists, inhibitors of the EGF receptor and/or VEGF receptor and/or integrin receptors or any other protein tyrosine kinase receptors which are not classified under the synthetic small-molecules, inhibitors directed to EGF receptor and/or VEGF receptor and/or integrin receptors or any other protein tyrosine kinase receptors, which are fusion proteins, compounds which interact with nucleic acids and which are classified as alkylating agents or platinum compounds, compounds which interact with nucleic acids and which are classified as anthracyclines, as DNA intercalators or as DNA cross-linking agents, including DNA minor-groove binding compounds, anti-metabolites, naturally occurring, semi-synthetic or synthetic bleomycin type antibiotics, inhibitors of DNA transcribing enzymes, and especially the topoisomerase I or topoisomerase II inhibitors, chromatin modifying agents, mitosis inhibitors, anti-mitotic agents, cell-cycle inhibitors, proteasome inhibitors, enzymes, hormones, hormone antagonists, hormone inhibitors, inhibitors of steroid biosynthesis, steroids, cytokines, hypoxia-selective cytotoxins, inhibitors of cytokines, lymphokines, antibodies directed against cytokines, oral and parenteral tolerance induction agents, supportive agents, chemical radiation sensitizers and protectors, photo-chemically activated drugs, synthetic poly- or oligonucleotides, optionally modified or conjugated, non-steroidal anti-inflammatory drugs, cytotoxic antibiotics, antibodies targeting the surface molecules of cancer cells, antibodies targeting growth factors or their receptors, inhibitors of metalloproteinases, metals, inhibitors of oncogenes, inhibitors of gene transcription or of RNA translation or protein expression, complexes of rare earth elements, and photo-chemotherapeutic agents.

In other embodiments, the chemotherapeutic agent is selected from the group consisting of paclitaxel (taxol), docetaxel, a vinca alkaloid such as navelbine, vinblastin, vincristin, vindesine or vinorelbine, an alkylating agent or a platinum compound such as melphalan, cyclophosphamide, an oxazaphosphorine, cisplatin, carboplatin, oxaliplatin, satraplatin, tetraplatin, iproplatin, mitomycin, streptozocin, carmustine (BCNU), lomustine (CCNU), busulfan, ifosfamide, streptozocin, thiotepa, chlorambucil, a nitrogen mustard such as mechlorethamine, an immunomodulatory drug such as thalidomide, its R- and S-enantiomers and its derivatives, or revimid (CC-5013)), an ethyleneimine compound, an alkylsulphonate, daunorubicin, doxorubicin (adriamycin), liposomal doxfflubicin (doxil), epirubicin, idarubicin, mitoxantrone, amsacrine, dactinomycin, distamycin or a derivative thereof, netropsin, pibenzimol, mitomycin, CC-1065, a duocarmycin, mithramycin, chromomycin, olivomycin, a phtalanilide such as propamidine or stilbamidine, an anthramycin, an aziridine, a nitrosourea or a derivative thereof, a pyrimidine or purine analogue or antagonist or an inhibitor of the nucleoside diphosphate reductase such as cytarabine, 5-fluorouracile (5-FU), uracil mustard, fludarabine, gemcitabine, capecitabine, mercaptopurine, cladribine, thioguanine, methotrexate, pentostatin, hydroxyurea, or folic acid, an acridine or a derivative thereof, a rifamycin, an actinomycin, adramycin, a camptothecin such as irinotecan (camptosar) or topotecan, an amsacrine or analogue thereof, a tricyclic carboxamide, an histonedeacetylase inhibitor such as SAHA, MD-275, trichostatin A, CBHA, LAQ824, or valproic acid, a proteasome inhibitor such as bortezomib, a small molecule VEGF receptor antagonist such as vatalanib (PTK-787/ZK222584), SU-5416, SU-6668, SU-11248, SU-14813, AZD-6474, AZD-2171, CP-547632, CEP-7055, AG-013736, IM-842 or GW-786034, an antagonist of the mitogen-activated protein kinase such as BAY-43-9006 or BAY-57-9006, a dual EGFR/HER2 antagonist such as gefitinib, erlotinib, CI-1033 or GW-2016, an EGFR antagonist such as iressa (ZD-1839), tarceva (OSI-774), PKI-166, EKB-569, HKI-272 or herceptin, a quinazoline derivative such as 4-[(3-chloro-4-fluorophenyl)amino]-6-{[-4-(N,N-dimethylamino)-1-oxo-2-but-en-1-yl]amino}-7-((S)-tetrahydrofuran-3-yloxy)-quinazoline or 4-[(3-chloro-4-fluoro-phenyl)amino]-6-{[4-(homomorpholin-4-yl)-1-oxo-2-bu-ten-1-yl]amino-}-7-[(S)-(tetrahydrofuran-3-yl)oxy]-quinazoline, or a pharmaceutically acceptable salt thereof, an inhibitor of the transcription factor complex ESX/DRIP130/Sur-2, an inhibitor of HER-2 expression, such as the heat shock protein HSP90 modulator geldanamycin and its derivative 17-allylaminogeldanamycin or 17-AAG, a protein kinase receptor antagonist which is not classified under the synthetic small molecules such as atrasentan, rituximab, cetuximab, Avastin™ (bevacizumab), IMC-1C11, erbitux (C-225), DC-101, EMD-72000, vitaxin, imatinib, and an antibody targeting the surface molecules of cancer cells such as apolizumab or 1D09C3.

In some other embodiments, the chemotherapeutic agent is a compound which reduces the transport of hyaluronan mediated by one or more ABC transporters, or drug transport inhibitor, such as a P-glycoprotein (P-gp) inhibitor molecule or inhibitor peptide, an MRP1 inhibitor, an antibody directed against and capable of blocking the ABC transporter, an antisense oligomer, iRNA, siRNA or aptamer directed against one or more ABC transporters. Examples of P-glycoprotein (P-gp) inhibitor molecules in accordance with the present invention are zosuquidar (LY 335973), its salts (especially the trichloride salt) and its polymorphs, cyclosporin A (also known as cyclosporine), verapamil or its R-isomer, tamoxifen, quinidine, d-alpha tocopheryl polyethylene glycol 1000 succinate, VX-710, PSC833, phenothiazine, GF120918 (II), SDZ PSC 833, TMBY, MS-073, S-9788, SDZ 280-446, XR(9051) and functional derivatives, analogues and isomers of these.

D. Adoptive Immunotherapy

In other aspects, the at least one CMV antigen, or nucleic acids encoding the at least one CMV antigen, also can provide for compositions and methods for providing CMV antigen-primed, antigen-presenting cells, and/or CMV antigen-specific T lymphocytes generated with these antigen-presenting cells, e.g., for use as active compounds in immunomodulating compositions and methods for prophylactic or therapeutic applications directed at cells that express a CMV antigen.

Accordingly, in one aspect, the invention provides a method for making CMV antigen-primed, antigen-presenting cells by:

contacting antigen-presenting cells with at least one CMV antigen, or nucleic acids encoding the at least one CMV antigen, in vitro under a condition sufficient for the at least one CMV antigen to be presented by the antigen-presenting cells. The at least one CMV antigen, or nucleic acids encoding the at least one CMV antigen, are as described above.

The at least one CMV antigen, or nucleic acids encoding the at least one CMV antigen, can be contacted with a homogenous, substantially homogenous, or heterogeneous composition comprising antigen-presenting cells. For example, the composition can include but is not limited to whole blood, fresh blood, or fractions thereof such as, but not limited to, peripheral blood mononuclear cells, buffy coat fractions of whole blood, packed red cells, irradiated blood, dendritic cells, monocytes, macrophages, neutrophils, lymphocytes, natural killer cells, and natural killer T cells. If, optionally, precursors of antigen-presenting cells are used, the precursors can be cultured under suitable culture conditions sufficient to differentiate the precursors into antigen-presenting cells. Preferably, the antigen-presenting cells (or, optionally, precursors) are selected from monocytes, macrophages, cells of myeloid lineage, B cells, dendritic cells, or Langerhans cells.

The amount of the at least one CMV antigen, or nucleic acids encoding the at least one CMV antigen, to be placed in contact with antigen-presenting cells can be determined by one of ordinary skill in the art by routine experimentation. Generally, antigen-presenting cells are contacted with the at least one CMV antigen, or nucleic acids encoding the at least one CMV antigen, for a period of time sufficient for cells to present the processed forms of the antigens for the modulation of T cells. In one embodiment, antigen-presenting cells are incubated in the presence of the at least one CMV antigen, or nucleic acids encoding the at least one CMV antigen, for less than about a week, illustratively, for about 1 minute to about 48 hours, about 2 minutes to about 36 hours, about 3 minutes to about 24 hours, about 4 minutes to about 12 hours, about 6 minutes to about 8 hours, about 8 minutes to about 6 hours, about 10 minutes to about 5 hours, about 15 minutes to about 4 hours, about 20 minutes to about 3 hours, about 30 minutes to about 2 hours, and about 40 minutes to about 1 hour. The time and amount of antigens, or nucleic acids encoding the antigens, necessary for the antigen presenting cells to process and present the antigens can be determined, for example using pulse-chase methods wherein contact is followed by a washout period and exposure to a read-out system e.g., antigen reactive T cells.

Typically, the length of time necessary for an antigen-presenting cell to present an antigen on its surface can vary depending on a number of factors including the antigen or form (e.g., peptide versus encoding polynucleotide) of antigen employed, its dose, and the antigen-presenting cell employed, as well as the conditions under which antigen loading is undertaken. These parameters can be determined by the skilled artisan using routine procedures. Efficiency of priming of an antigen-presenting cell can be determined by assaying T cell cytotoxic activity in vitro or using antigen-presenting cells as targets of CTLs. Other methods that can detect the presence of antigen on the surface of antigen-presenting cells are also contemplated by the presented invention.

A number of methods for delivery of antigens to the endogenous processing pathway of antigen-presenting cells are known. Such methods include but are not limited to methods involving pH-sensitive liposomes, coupling of antigens to potent adjuvants, apoptotic cell delivery, pulsing cells onto dendritic cells, delivering recombinant chimeric virus-like particles (VLPs) comprising antigen to the MHC class I processing pathway of a dendritic cell line.

In one embodiment, solubilized CMV antigen is incubated with antigen-presenting cells. In other embodiments, the at least one CMV antigen can be coupled to a cytolysin to enhance the transfer of the antigens into the cytosol of an antigen-presenting cell for delivery to the MHC class I pathway. Exemplary cytolysins include saponin compounds such as saponin-containing Immune Stimulating Complexes (IS-COMs), pore-forming toxins (e.g., an alpha-toxin), and natural cytolysins of gram-positive bacteria such as listeriolysin O (LLO), streptolysin O (SLO), and perfringolysin O (PFO).

By way of another example, in other embodiments, antigen-presenting cells, preferably dendritic cells and macrophage, can be isolated according to methods known in the art and transfected with polynucleotides by methods known in the art for introducing nucleic acids encoding CMV antigens into the APCs. Transfection reagents and methods (e.g., SuperFect®) also are commercially available. For example, RNAs encoding CMV antigens can be provided in a suitable medium (e.g., Opti-MEM®) and combined with a lipid (e.g., a cationic lipid) prior to contact with APCs. Non-limiting examples of lipids include LIPOFECTIN™, LIPOFECTAMINE™, DODAC/DOPE, and CHOL/DOPE. The resulting polynucleotide-lipid complex can then be contacted with APCs. Alternatively, the polynucleotide can be introduced into APCs using techniques such as electroporation or calcium phosphate transfection. The polynucleotide-loaded APCs can then be used to stimulate cytotoxic T lymphocyte (CTL) proliferation in vivo or ex vivo. In one embodiment, the ex vivo expanded CTL is administered to the subject in a method of adoptive immunotherapy. The ability of the polynucleotide-loaded antigen-presenting cells to stimulate a CTL response can be determined by known methods, for example by assaying the ability of effector cells to lyse a target cell. Methods and compositions using antigen-presenting cells loaded with e.g., RNA are described in U.S. Pat. No. 6,306,388 to Nair et al., which is incorporated herein by reference for its teaching of methods of generation and use of APCs loaded with RNA.

In another aspect, the present invention provides a composition comprising antigen-presenting cells that have been contacted in vitro with at least one CMV antigen, or nucleic acids encoding the at least one CMV antigen, under a condition sufficient for the at least one CMV antigen to be presented by the antigen-presenting cells.

In another aspect, the present invention provides a method for preparing lymphocytes specific for the at least one CMV antigen. The method comprises contacting lymphocytes with the antigen-presenting cells described above under conditions sufficient to produce CMV antigen-specific lymphocyte capable of eliciting an immune response against a cell that expresses a CMV antigen. Thus, the antigen-presenting cells also can be used to provide lymphocytes, including T lymphocytes and B lymphocytes, for eliciting an immune response against cell that expresses a CMV antigen.

In one embodiment, a preparation of T lymphocytes is contacted with the antigen-presenting cells described above for a period of time, preferably for at least about 24 hours, for priming the T lymphocytes to the at least one CMV antigen presented by the antigen-presenting cells.

For example, in another embodiment, a population of antigen-presenting cells can be co-cultured with a heterogeneous population of peripheral blood T lymphocytes together with at least one CMV antigen, or nucleic acids comprising the at least one CMV antigen. The cells can be co-cultured for a period of time and under conditions sufficient for the CMV antigens or their processed forms to be presented by the antigen-presenting cells and the antigen-presenting cells to prime a population of T lymphocytes to respond to cells that express a CMV antigen. Accordingly, T lymphocytes and B lymphocytes that are primed to respond to cells that express a CMV antigen can be prepared.

As described herein, the ability to induce lymphocytes to exhibit an immune response can be determined by any method including, but not limited to, determining T lymphocyte cytolytic activity in vitro using for example CMV antigen-specific antigen-presenting cells as targets of CMV antigen-specific cytolytic T lymphocytes (CTL); assaying CMV antigen-specific T lymphocyte proliferation; and determining B cell response to cells expressing a CMV antigen using, for example, ELISA methods.

T lymphocytes can be obtained from any suitable source such as peripheral blood, spleen, and lymph nodes. The T lymphocytes can be used as crude preparations or as partially purified or substantially purified preparations, which can be obtained by standard techniques including, but not limited to, methods involving immunomagnetic or flow cytometry techniques using antibodies.

Also contemplated within the scope of the present invention are cells that have been modified genetically for specific recognition of a cell that expresses a CMV antigen. (e.g., T-cells genetically engineered to express cell-specific antibodies on their surface). In some embodiments, antigen-specific T cells are modified by gene transfer techniques known in the art to express one or more heterologous genes, for example a marker gene or a gene whose gene product can enhance or impart a particular phenotype or function to the antigen-specific T cell. Thus, for example, a marker gene can be expressed within activated T cells responding to antigen pulsed dendritic cells and allow for the selective enrichment and modification of antigen-specific T cells. By way of another example, antigen-specific T cells can be modified to express a receptor (e.g., a chemokine receptor) to migrate toward a ligand of the receptor in vitro and in vivo.

In other aspects, the present invention provides a composition comprising the antigen-presenting cells or the lymphocytes described above, and a pharmaceutically acceptable carrier and/or diluent. In some embodiments, the composition further comprises an adjuvant as described above.

In another aspect, the present invention provides a method for eliciting an immune response to the cell that expresses a CMV antigen, the method comprising administering to the subject the antigen-presenting cells or the lymphocytes described above in effective amounts sufficient to elicit the immune response. In some embodiments, the invention provides a method for treatment or prophylaxis of a neoplastic disease or symptoms associated with CMV, the method comprising administering to the subject an effective amount of the antigen-presenting cells or the lymphocytes described above. In one embodiment, the antigen-presenting cells or the lymphocytes are administered systemically, preferably by injection. Alternately, one can administer locally rather than systemically, for example, via injection directly into tissue, preferably in a depot or sustained release formulation. Furthermore, one can administer in a targeted drug delivery system, for example, in a liposome that is coated with tissue-specific antibody. The liposomes can be targeted to and taken up selectively by the tissue. In another embodiment, the invention provides use of the antigen-presenting cells or the lymphocytes in the preparation of a medicament for eliciting an immune response to a cell that expresses a CMV antigen, preferably for treating or preventing cancer.

Accordingly, the antigen-primed antigen-presenting cells of the present invention and the antigen-specific T lymphocytes generated with these antigen-presenting cells can be used as active compounds in immunomodulating compositions for prophylactic or therapeutic applications for cancer. In some embodiments, the CMV antigen-primed antigen-presenting cells of the invention can be used for generating CD8+ CTL, CD4+ CTL, and/or B lymphocytes for adoptive transfer to the subject. Thus, for example, CMV antigen-specific CTLs can be adoptively transferred for therapeutic purposes in subjects afflicted with a malignant tumor such as a glioma.

The antigen-presenting cells and/or lymphocytes described above can be administered to a subject, either by themselves or in combination, for eliciting an immune response, particularly for eliciting an immune response to cells that express a CMV antigen. Such cell-based compositions are useful, therefore, for treating or preventing cancer. The cells can be introduced into a subject by any mode that elicits the desired immune response to cells that express a CMV antigen. Furthermore, the antigen-presenting cells and/or lymphocytes can be derived from the subject (i.e., autologous cells) or from a different subject that is MHC matched or mismatched with the subject (e.g., allogeneic). The injection site can be selected from subcutaneous, intraperitoneal, intramuscular, intradermal, intravenous, or intralymphoid.

Single or multiple administrations of the antigen-presenting cells and lymphocytes can be carried out with cell numbers and treatment being selected by the care provider (e.g., physician). Preferably, the antigen-presenting cells and/or lymphocytes are administered in a pharmaceutically acceptable carrier. Suitable carriers can be the growth medium in which the cells were grown, or any suitable buffering medium such as phosphate buffered saline. The cells can be administered alone or as an adjunct therapy in conjunction with other therapeutics.

Accordingly, the invention contemplates methods for treatment and/or prophylaxis of a cell that expresses a CMV antigen, preferably a CMV-associated cancer cell, the method comprising administering to a subject in need of such treatment or prophylaxis a therapeutically/prophylactically effective amount of a composition as described herein.

Techniques for formulating and administering can be found in Remington's Pharmaceutical Sciences, Mack Publishing Co., Easton, Pa., latest edition. Suitable routes can, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the therapeutic/prophylactic compositions of the present invention can be formulated in aqueous solutions, preferably in physiologically compatible buffers such as Hanks' solution, Ringer's solution, or physiological saline buffer.

F. Antibodies

The compositions of the present invention also can be used to raise antibodies targeting a cell that expresses a CMV antigen. Accordingly, in other aspects, the composition and methods of the present invention provide one or more antibodies against the cell that expresses a CMV antigen, which antibodies themselves have many uses such as, for example, passive immunization or target-specific delivery for effectors as well as uses for diagnostic tests and kits based upon immunological binding. Thus, in some embodiments, the present invention provides CMV-associated, cancer cell-specific antibodies that can be used in therapeutic and/or diagnostic applications.

The antibodies of the present invention can be used in screening or diagnostic applications. The antibodies according to the present invention are valuable for in vitro and in vivo diagnostic purposes. For example, the antibodies can be used in western blots, immunoprecipitation, enzyme-linked immunosorbent assay (ELISA), fluorescence activated cell sorting (FACS), indirect immunofluoresence microscopy, immunohistochemistry (IHC), etc. In one embodiment, the present invention provides an immunological method for determining a cell that expresses a CMV antigen, the method comprising contacting the cell with at least one antibody as disclosed herein.

For example, the antibodies can be used as diagnostic agents for assaying for the detection of CMV antigen expressing cells. The antibodies of the present invention should be particularly suitable as diagnostic agents given their binding affinity to a cell that expresses a CMV antigen. Essentially, a sample comprising cells (e.g., cancer cells) will be incubated with the antibodies for a sufficient time to permit immunological interactions to occur. Those skilled in the art will recognize that there are many variations in these basic procedures. These variations include, for example, RIA, ELISA, precipitation, agglutination, complement fixation and immunofluorescence. Preferably, the subject antibodies will be labeled to permit the detection of antibody-cell immunocomplexes. Further, the antibodies of the present invention are also useful for detection and quantification of cells that express a CMV antigen in vitro, or to kill and eliminate such cells from a population of mixed cells as a step in the purification of other cells.

The labels that are used in making labeled versions of the antibodies include moieties that may be detected directly, such as radiolabels and fluorochromes, as well as moieties, such as enzymes, that must be reacted or derivatized to be detected. Radiolabels include, but are not limited to, $^{99}$Tc, $^{203}$Pb, $^{67}$Ga, $^{68}$Ga, $^{72}$As, $^{111}$In, $^{113m}$In, $^{97}$Ru, $^{62}$Cu, $^{641}$Cu, $^{52}$Fe, $^{52m}$Mn, $^{51}$Cr, $^{186}$Re, $^{188}$Re, $^{77}$As, $^{90}$Y, $^{67}$Cu, $^{169}$Er, $^{121}$Sn, $^{127}$Te, $^{142}$Pr, $^{143}$Pr, $^{198}$Au, $^{199}$Au, $^{161}$Tb, $^{109}$Pd, $^{165}$Dy, $^{149}$Pm, $^{151}$Pm, $^{153}$Sm, $^{157}$Gd, $^{159}$Gd, $^{166}$Ho, $^{172}$Tm, $^{169}$Yb, $^{175}$Yb, $^{177}$Lu, $^{105}$Rh, and $^{111}$Ag. The radiolabel can be detected by any of the currently available counting procedures.

An enzyme label can be detected by any of the currently utilized calorimetric, spectrophotometric, fluorospectrophotometric or gasometric techniques. The enzyme is combined with the antibody with bridging molecules such as carbodiimides, periodate, diisocyanates, glutaraldehyde and the like. Many enzymes which can be used in these procedures are known and can be utilized. Examples are peroxidase, alkaline phosphatase, β-glucuronidase, β-D-glucosidase, urease, glucose oxidase plus peroxidase, galactose oxidase plus peroxidase and acid phosphatase. Fluorescent materials which may be used include, for example, fluorescein and its derivatives, rhodamine and its derivatives, auramine, dansyl, umbelliferone, luciferia, 2,3-dihydrophthalazinediones, horseradish peroxidase, alkaline phosphatase, lysozyme, and glucose-6-phosphate dehydrogenase. The antibodies may be tagged with such labels by known methods. For instance, coupling agents such as aldehydes, carbodiimides, dimaleimide, imidates, succinimides, bis-diazotized benzadine and the like may be used to tag the antibodies with the above-described fluorescent, chemiluminescent, and enzyme labels. Various labeling techniques are described in Morrison, Methods in Enzymology, (1974), 32B, 103; Syvanen et al., J. Biol. Chem., (1973), 284, 3762; and Bolton and Hunter, Biochem J., (1973), 133, 529.

The antibodies and labeled antibodies may be used in a variety of immunoimaging or immunoassay procedures to detect the presence of cells that express a CMV antigen in a subject or monitor the status of such cells or cancer in the subject. When used to monitor the status of a cell that expresses a CMV antigen, a quantitative immunoassay procedure can be used. For example, if such monitoring assays are carried out periodically and the results compared, a determination can be made regarding whether a subject's tumor burden has increased or decreased, wherein the tumor is a CMV-associated tumor. Common assay techniques that may be used include direct and indirect assays.

For example, in the case of therapeutic applications, the antibodies can be used to inhibit a target involved in disease progression or to bring about the cytotoxic death of target cells. Also, such therapeutic antibodies can inhibit a signaling pathway or induce antibody-dependent cell-mediated cytotoxicty, complement-dependent cytotoxicty, etc.

The antibodies of this invention thus provide effective targeting moieties that can, but need not, be transiently or permanently coupled to an effector (thereby forming a hybrid molecule or chimeric moiety) and used to direct that effector to a particular target cell (e.g., a cancer cell).

The effector molecule refers to a molecule or group of molecules that is to be specifically transported to the target cell. The effector molecule typically has a characteristic activity that is to be delivered to the target cell. Effector molecules include, but are not limited to cytotoxins, labels, radionuclides (e.g., $^{211}$At), ligands, antibodies, drugs, liposomes, epitope tags, and the like. Preferred effectors include cytotoxins (e.g., *Pseudomonas* exotoxin, gelonin, ricin, abrin, *Diphtheria* toxin, and the like), immunomodulators as described herein, or cytotoxic drugs or prodrugs, in which case the hybrid molecule may act as a potent cell-killing agent specifically targeting the cytotoxin to cells expressing the CMV antigen.

Further examples of effectors include, but are not limited to, granzyme, luciferase, vascular endothelial growth factor, β-lactamase, Tr-apo-1, Ang II, TAT, alkylating agents, daunomycin, adriamycin, chlorambucil, anti-metabolites (e.g., methotrexate), modaccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Sapaonaria officinalis* inhibitor, mitogellin, restrictocoin, phenomycin and enomycin.

In still other embodiments, the effector can include a liposome encapsulating a drug (e.g., an anti-cancer drug such as doxirubicin, vinblastine, taxol, or other chemotherapeutic agents described herein), an antigen that stimulates recognition of the bound cell by components of the immune system, and antibody that specifically binds immune system components and directs them to the cells that express a CMV antigen, and the like.

Other suitable effector molecules include pharmacological agents or encapsulation systems containing various pharmacological agents. Thus, the targeting molecule of the hybrid molecule may be attached directly to a drug that is to be delivered directly to cells that express a CMV antigen. Such drugs are well known to those of skill in the art and include, but are not limited to, doxirubicin, vinblastine, genistein, an antisense molecule, the various other chemotherapeutic agents described herein, and the like.

Alternatively, the effector molecule may be an encapsulation system, such as a viral capsid, a liposome, or micelle that contains a therapeutic composition such as a drug, a nucleic acid (e.g., an antisense nucleic acid), or another therapeutic moiety that is preferably shielded from direct exposure to the circulatory system. Methods of preparing liposomes attached to antibodies are well known to those of skill in the art. See, for example, U.S. Pat. No. 4,957,735; Connor, J. et al. (1985) Pharmacol. Ther., 28: 341-365.

G. Determining CMV Nucleic Acid

In other aspects, the present invention provides compositions and methods for determining CMV nucleic acid in a subject, preferably CMV DNA in blood or other biological fluid, e.g., for determining subclinical viremia in a sample of blood obtained from the subject. Accordingly, in various embodiments, the compositions and methods provide effective diagnostic, monitoring, and prognostic tests/assays that complement various diagnostic and/or therapeutic procedures and treatments including methods described herein such as, for example, prophylactic and/or therapeutic treating of a disease or condition associated with a precancerous cell, a cancer cell, or a cell-type predisposed to developing cancer associated with CMV.

By way of example, an amplification method is provided that is reliable in determining CMV reactivation in human patients undergoing allogeneic bone marrow transplantation (aBMT), and in some cases preceded detection of viral reactivation by as much as six weeks compared to currently used clinically approved diagnostic CMV PCR assays. As also illustrated by examples provided herein, CMV DNA from surgically resected GBM specimens can be analyzed using PCR amplification, for example, across a variable region of the gB gene in HCMV genome (region 82801-84180, NCBI GenBank accession#NC_001347) and subsequent DNA sequencing.

In one embodiment, the invention provides a method of determining CMV nucleic acid in a subject, the method comprising: (a) amplifying a nucleic acid molecule from a biological sample to obtain an amplicon, wherein amplifying comprises contacting the nucleic acid molecule with at least one pair of primers comprising a first primer and a second primer, wherein the amplicon is about 1000 base pairs (bp) or less in length; and (b) determining presence of the amplicon, wherein presence of the amplicon is indicative of CMV nucleic acid in the subject.

In some embodiments, the amplicon is no greater than about 1000 bp in length, illustratively, no greater than about 900 bp, no greater than about 800 bp, no greater than about 700 bp, no greater than about 600 bp, no greater than about 500 bp, no greater than about 400 bp, no greater than about 300 bp, no greater than 200 bp, no greater than about 150 bp, no greater than about 100 bp, no greater than about 90 bp, no greater than about 80 bp, no greater than about 70 bp, no greater than about 60 bp, no greater than about 50 bp, and no greater than about 40 bp in length. In some embodiments, the amplicon is 200 base pairs (bp) or less in length.

Non-limiting examples of primer pairs and their corresponding target genes are shown in Tables 1 and 2.

TABLE 1

Human CMV primer pairs for determining CMV DNA

| Name (Genes-Primers) | Primer Pair Sequences (5' to 3')[1] | Amplicon Size (bp) | Detection Rate |
|---|---|---|---|
| gB-E1E2 | 5'-tcc aac acc cac agt acc cgt-3'(SEQ ID NO: 6)<br>5'-cgg aaa cga tgg tgt agt tcg-3'(SEQ ID NO: 7) | 268 | 51/223 (22.9%) |
| gB-i1i2 | 5'-cgc cgc ccg ccc cgc gcc cgc cgc ggc agc acc tgg ct-3'(SEQ ID NO: 8)<br>5'-gta aac cac atc acc cgt gga-3'(SEQ ID NO: 9) | 144 | 164/223 (73.5%) |
| gB-i3i4 | 5'-gcc gcg gca gca cct ggc t-3'(SEQ ID NO: 10)<br>5'-aac cac atc acc cgt gga-3'(SEQ ID NO: 11) | 122 | 152/223 (68.1%) |
| gB-5/6 | 5'-tac ccc tat cgc gtg tgt tc-3'(SEQ ID NO: 12)<br>5'-ata gga ggc gcc acg tat tc-3'(SEQ ID NO: 13) | 254 | 65/223 (29.1%) |
| gB-5/7 | 5'-tac ccc tat cgc gtg tgt tc-3'(SEQ ID NO: 14)<br>5'-cct cct ata acg cgg ctg ta-3'(SEQ ID NO: 15) | 320 | 11/50 (22%) |
| gB-7B/8 | 5'-tcc gaa gcc gaa gac tcg ta-3'(SEQ ID NO: 16)<br>5'-gat gta acc gcg caa cgt gt-3'(SEQ ID NO: 17) | 410 | 26/50 (52%) |

TABLE 1-continued

Human CMV primer pairs for determining CMV DNA

| Name (Genes-Primers) | Primer Pair Sequences (5' to 3')[1] | Amplicon Size (bp) | Detection Rate |
|---|---|---|---|
| gB-9/10 | 5'-ttt gga gaa aac gcc gac-3' (SEQ ID NO: 18)<br>5'-cgc gcg gca atc ggt ttg ttg tc-3' (SEQ ID NO: 19) | 748 | 10/50 (20%) |
| gp64-1/2 | 5'-ccg caa cct ggt gcc cat gg-3' (SEQ ID NO: 20)<br>5'-cgt ttg ggt tgc gca gcg gg-3' (SEQ ID NO: 21) | 138 | 7/50 (14%) |
| gpUL73-1/2 | 5'-ttc ggt cgg tca aca tcg taa g-3' (SEQ ID NO: 22)<br>5'-cac cca cgt atg taa acc tta c-3' (SEQ ID NO: 23) | 516 | 6/50 (12%) |
| IE1-A443/A444 | 5'-aga aag atg tcc tgg cag aac t-3' (SEQ ID NO: 24)<br>5'-cct cag gta caa tgt agt tct c-3' (SEQ ID NO: 25) | 605 | 37/223 (16.6%) |
| IE1-A445/A446 | 5'-aga aag atg tcc tgg cag aac t-3' (SEQ ID NO: 26)<br>5'-cct cag gta caa tgt agt tct c-3' (SEQ ID NO: 27) | 422 | 40/223 (17.9%) |
| IE-1/2 | 5'-cgt cct tga cac gat gga gt-3' (SEQ ID NO: 28)<br>5'-att ctt cgg cca act ctg ga-3' (SEQ ID NO: 29) | 311 | 10/50 (20%) |
| IE-3/4 | 5'-ccc tga taa tcc tga cga gg-3' (SEQ ID NO: 30)<br>5'-cat agt ctg cag gaa cgt cgt-3' (SEQ ID NO: 31) | 201 | 12/50 (24%) |
| IEA1-P1/P2 | 5'-caa gcg gcc tct gat aac caa gc-3' (SEQ ID NO: 32)<br>5'-ctc ttc ctc tgg ggc aac ttc ctc-3' (SEQ ID NO: 33) | 421 | 9/50 (18%) |
| MIE-P1/P2 | 5'-ggg tgc tgt cct gct atg tct ta-3' (SEQ ID NO: 34)<br>5'-cat cac tct gct cac ttt ctt cc-3' (SEQ ID NO: 35) | 370 | 29/50 (58%) |
| pp65-1/2 | 5'-cac ctg tca ccg ctg cta tat ttg c-3' (SEQ ID NO: 36)<br>5'-cac cac gca gcg cc ctt gat ctt t-3' (SEQ ID NO: 37) | 400 | 10/50 (20%) |
| pp65-3/4 | 5'-gac aca aca ccg taa agc-3' (SEQ ID NO: 38)<br>5'-cag cgt tcg tgt ttc c-3' (SEQ ID NO: 39) | 278 | 8/50 (16%) |
| pp65-11/12 | 5'-agc gcg tac aca tag atc ga-3' (SEQ ID NO: 40)<br>5'-gct gat ctt ggt atc gca gta c-3' (SEQ ID NO: 41) | 186 | 12/50 (24%) |
| pp65-13/14 | 5'-agt ggt gca cgt tga tgc tg-3' (SEQ ID NO: 42)<br>5'-tcg ctg atc ttg gta tcg ca-3' (SEQ ID NO: 43) | 232 | 15/50 (30%) |
| UL54-S1/AS1 | 5'-cta cac ggt agc gac gag ac-3' (SEQ ID NO: 44)<br>5'-atg ttt cta ggc tac tct gac tg-3' (SEQ ID NO: 45) | 501 | 8/50 (16%) |
| UL89/93 (EcoRI Fragment D-P1/P2) | 5'-gat ccg acc cat tgt cta ag-3' (SEQ ID NO: 46)<br>5'-ggc agc tat cgt gac tgg ga-3' (SEQ ID NO: 47) | 152 | 10/50 (20%) |
| UL144-1/2 | 5'-gcc tct gat aat gct cat ctg c-3' (SEQ ID NO: 48)<br>5'-ggc tag agt atg acg acc gct t-3' (SEQ ID NO: 49) | 400 | 12/50 (24%) |
| UL144-5/6 | 5'-tcg ttg ttt gtg atg ttg gac gcc-3' (SEQ ID NO: 50)<br>5'-tga agt gca act ggg caa tga gtg-3' (SEQ ID NO: 51) | 265 | 21/50 (42%) |
| UL144-7/8 | 5'-cgt tgt ttg tga tgt tgg acg cct-3' (SEQ ID NO: 52)<br>5'-tga agt gca actg ggc aat gag tg-3' (SEQ ID NO: 53) | 264 | 23/50 (46%) |

TABLE 1-continued

Human CMV primer pairs for determining CMV DNA

| Name (Genes-Primers) | Primer Pair Sequences (5' to 3')[1] | Amplicon Size (bp) | Detection Rate |
|---|---|---|---|
| UL144-9/10 | 5'-ttg ttt gtg atg ttg gac gcc tgg-3'(SEQ ID NO: 54)<br>5'-tga agt gca act ggg caa tga gtg-3'(SEQ ID NO: 55) | 262 | 18/50 (36%) |
| UL144-11/12 | 5'-atg gtt ctt agg tgc gca tac ggt-3'(SEQ ID NO: 56)<br>5'-tga agt gca act ggg caa tga gtg-3'(SEQ ID NO: 57) | 223 | 17/50 (34%) |
| UL144-13/14 | 5'-agg cta gag tat gac gac cgc ttt-3'(SEQ ID NO: 58)<br>5'-acg gca cgt atg tat cgg gac ttt-3'(SEQ ID NO: 59) | 225 | 19/50 (38%) |
| US7/8 (HindIII-X Fragment-P1/P2) | 5'-gga tcc gca tgg cat tca cgt atg t-3' (SEQ ID NO: 60)<br>5'-gaa ttc agt gga taa cct gcg gcg a-3' (SEQ ID NO: 61) | 406 | 2/50 (40%) |
| US28-10/11 | 5'-agc gtg ccg tgt acg t ta c-3'(SEQ ID NO: 62)<br>5'-ata aag aca agc acg acc-3'(SEQ ID NO: 63) | 412 | 14/50 (28%) |

[1]Primers were designed in lab with NTI Advance 10 software (Invitrogen, Carlsbad, CA)

TABLE 2

Quantitative PCR results on peripheral blood samples from patients undergoing allogeneic bone marrow transplantation.

| Genes-Primers | Sequences of Primers & Probes[1] 5'-3' | HCMV Detection Rate | Lowest Threshold of Detection (copy#/qPCR) | Ct Value to Detect 10 copies of HCMV |
|---|---|---|---|---|
| gB-18/19/20 | 5'-aaa gag ctg cgt tcc agc aa-3' (SEQ ID NO: 64)<br>5'-gag gtc gtc cag acc ctt ga-3' (SEQ ID NO: 65)<br>5'-[FAM]-cat gcg cga att caa ctc gta caa gc-[TAMRA]-3' (SEQ ID NO: 66) | 9/30 (30%) | 10 | 38.1 |
| gB21/22/23 | 5'-atc gtg aga cct gta atc tga act gta-3' (SEQ ID NO: 67)<br>5'-gga agt tgc aaaa aaa tga taag ga-3' (SEQ ID NO: 68)<br>5'-[FAM]-tga cca tca cta ctg cgc gct cca-[TAMRA]-3' (SEQ ID NO: 69) | 16/30 (53.3%) | 1 | 31.5 |
| Pp65-1wx/2wx/3wx | 5'-ggc tac ggt tca ggg tca ga-3' (SEQ ID NO: 70)<br>5'-ccg ggc aag gcg tctt-3' (SEQ ID NO: 71)<br>5'-[FAM]-tgg gac gcc aac gac atc tac cg-[TAMRA]-3' (SEQ ID NO: 72) | 9/30 (30%) | 10 | 37.4 |
| Pp65-4wx/5wx/6wx | 5'-gcg cac gag ctg gtt tg-3' (SEQ ID NO: 73)<br>5'-aca cct tga cgt act ggt cac cta t-3' (SEQ ID NO: 74)<br>5'-[FAM]-acg cgc gca acc aag atg cag-[TAMRA]-3' (SEQ ID NO: 75) | 9/30 (30%) | 10 | 34.5 |
| Pp65-7/8/9 | 5'-aca cat aga tcg aca tgg gct cct-3' (SEQ ID NO: 76)<br>5'-tgc agg tgc agc aca cgt act tta-3' (SEQ ID NO: 77)<br>5'-[FAM]-ttg tgc acg ttg acc gac acg ttc t-[TAMRA]-3' (SEQ ID NO: 78) | 9/30 (30%) | 10 | 35.1 |

TABLE 2-continued

Quantitative PCR results on peripheral blood samples from patients undergoing allogeneic bone marrow transplantation.

| Genes-Primers | Sequences of Primers & Probes¹ 5'-3' | HCMV Detection Rate | Lowest Threshold of Detection (copy#/qPCR) | Ct Value to Detect 10 copies of HCMV |
|---|---|---|---|---|
| Pp-65-21/22/23 | 5'-tcg cgc ccg aag agg-3' (SEQ ID NO: 79)<br>5'-cgg ccg gat tgt gga tt-3' (SEQ ID NO: 80)<br>5-[FAM]-cac cga cga gga ttc cga caa cg-[TAMRA]-3' (SEQ ID NO: 81) | 9/30 (30%) | 10 | 35.3 |
| Pp65-24/25/26 | 5'-gca gcc acg gga tcg tac t-3' (SEQ ID NO: 82)<br>5'-ggc ttt tac ctc aca cga gca tt-3' (SEQ ID NO: 83)<br>5'[FAM]-cgc gag acc gtg gaa ctg cg-[TAMRA]-3' (SEQ ID NO: 84) | 11/30 (36.7%) | 2 | 33.9 |
| Pp65-27/28/29 | 5'-gtc agc gtt cgt gtt tcc ca-3' (SEQ ID NO: 85)<br>5'-ggg aca caa cac cgt aaa gc-3' (SEQ ID NO: 86)<br>5'-[FAM-5'-ccc gca acc cgc aac cct tca tg-[TAMRA]-3' (SEQ ID NO: 87) | 9/30 (30%) | 10 | 35.7 |
| Pp65-30/31/32 | 5'-gcg gta aga cgg gca aat ac-3' (SEQ ID NO: 88)<br>5'-ggc gtc gag atg ttc gta gag-3' (SEQ ID NO: 89)<br>5'-[FAM]-cac cat cga cac cac acc tc atg a-[TAMRA]-3' (SEQ ID NO: 90) | 9/30 (30%) | 10 | 35.2 |
| US28-1/2/3 | 5'-cag cgt gcc gtg tac gtt act-3' (SEQ ID NO: 91)<br>5'-gtg caa tct ccg tga taa aac aca-3' (SEQ ID NO: 92)<br>5'-[FAM]-act gcc tgt ttc tac gtg gct atg ttt gcc-[TAMRA]-3' (SEQ ID NO: 93) | 10/30 (33.3%) | 5 | 33.1 |
| US28-4/5/6 | 5'-tgg cta tgt ttg cca gtt tgt g-3' (SEQ ID NO: 94)<br>5'-cag gcc gat atc tca tgt aaa caa t-3' (SEQ ID NO: 95)<br>5'-[FAM]-ttt atc acg gag att gca ctc gat cgc t-[TAMRA]-3' (SEQ ID NO: 96) | 9/30 (30 7%) | 10 | 37.3 |
| US28-7/8/9 | 5'-gat gca ata cct cct aga tca caa ctc-3' (SEQ ID NO: 97)<br>5'-gca aac ata gcc acg tag aaa ca-3' (SEQ ID NO: 98)<br>5'-[FAM]-cca gcg tgc cgt gta cgt tac tca ctg-[TAMRA]-3' (SEQ ID NO: 99) | 11/30 (36%) | 2 | 32.0 |
| HXFL4-1/2/3 | 5'-aag cgc tgg ata cac ggt aca-3' (SEQ ID NO: 100)<br>5'-gaa tac aga cac tta gag ctc ggg gt-3' (SEQ ID NO: 101)<br>5'-[FAM]-ctg cca gca cg tat ccc aac agc a-[TAMRA]-3' (SEQ ID NO: 102) | 11/30 (36.7%) | 2 | 32.2 |
| IE-5/6/7 | 5'-caa gaa ctc agc ctt ccc taa gac-3' (SEQ ID NO: 103)<br>5'-tga ggc aag ttc tgc aat gc-3' (SEQ ID NO: 104)<br>5'-[FAM]-cca atg gct gca gtc agg cca tg-[TAMRA]-3' (SEQ ID NO: 105) | 9/30 (30%) | 10 | 38.0 |
| IE-8/9/10 | 5'-cag att aag gtt cga gtg gac atg-3' (SEQ ID NO: 106)<br>5'-agg cgc cag tga att tct ctt-3' (SEQ ID NO: 107) | 11/30 (36.7%) | 2 | 33.9 |

TABLE 2-continued

Quantitative PCR results on peripheral blood samples from patients undergoing allogeneic bone marrow transplantation.

| Genes-Primers | Sequences of Primers & Probes[1] 5'-3' | HCMV Detection Rate | Lowest Threshold of Detection (copy#/qPCR) | Ct Value to Detect 10 copies of HCMV |
|---|---|---|---|---|
| | 5'-[FAM]-tgc ggc ata gaa tca agg agc aca tg-[Tamra]-3' (SEQ ID NO: 108) | | | |

[1]Probes are shown as dual-labeled (5' FAM/3' TAMRA) with both a fluorophore and a quencher dye as used in real-time PCR.

In one embodiment, the first primer and the second primer are sufficient to provide for an amplicon that corresponds to a region of the gB (e.g., UL55) or MIE gene. However, any primer pair that can provide an amplicon corresponding to any region of a CMV nucleic acid also is within the scope of the present invention. In some embodiments, a primer for use in accordance with the present invention comprises a nucleotide sequence as shown in SEQ ID Nos:8-63.

In another embodiment, the first primer and the second primer correspond to a primer pair, wherein the first primer comprises a first primer sequence as shown by SEQ ID NO: 8, wherein the second primer comprises a second primer sequence as shown by SEQ ID NO:9. In other embodiments, the first primer and the second primer correspond to a primer pair, wherein the first primer comprises a first primer sequence as shown by SEQ ID NO:10, wherein the second primer comprises a second primer sequence as shown by SEQ ID NO:11.

In another embodiment, the first primer and the second primer correspond to a primer pair, wherein the first primer comprises a first primer sequence as shown by SEQ ID NO:16, wherein the second primer comprises a second primer sequence as shown by SEQ ID NO:17. In one embodiment, the first primer and the second primer correspond to a primer pair, wherein the first primer comprises a first primer sequence as shown by SEQ ID NO:34, wherein the second primer comprises a second primer sequence as shown by SEQ ID NO:35.

In other embodiments, the invention provides a method of determining CMV nucleic acid in a subject, the method comprising: (a) amplifying a nucleic acid molecule from a biological sample to obtain an amplicon, wherein amplifying comprises contacting the nucleic acid molecule with at least one pair of primers and at least one corresponding probe as shown in Table 2. In one embodiment, the pair of primers have a sequence shown as SEQ ID NOs:67 and 68; and the corresponding probe has a sequence shown as SEQ ID No:69.

In some embodiments, a method of determining CMV nucleic acid in the subject further comprises subjecting the biological sample to snap-freezing. Snap-freezing methods are well known in the art and can be performed using a variety of reagents and techniques including, for example, snap-freezing in liquid nitrogen or alcohol/dry ice (e.g., MeOH/dry ice).

Preferably, a method further comprises concentrating the nucleic acid following the step of snap-freezing. In one embodiment, the step of concentrating comprises precipitating the nucleic acid following the step of snap-freezing. In another embodiment, precipitating comprises contacting the nucleic acid with an alcohol (e.g., EtOH precipitation).

In still further embodiments, a step of determining the presence of an amplicon is performed by any suitable method of detection of the amplicon, for example a detection method that is characterized as having a sensitivity of detection of at least 10-fold that of an agarose gel stained with ethidium bromide.

In other aspects, the present invention provides a method of eliciting in a subject an immune response to a cell, the method comprising:

(a) amplifying a nucleic acid molecule from a biological sample from the subject to obtain an amplicon, wherein amplifying comprises contacting the nucleic acid molecule with at least one pair of primers comprising a first primer and a second primer, wherein the amplicon is about 1000 base pairs (bp) or less in length;

(b) determining presence of the amplicon, wherein presence of the amplicon is indicative of CMV nucleic acid in the subject; and (c) administering to the subject a pharmaceutically acceptable composition comprising at least one CMV antigen, or nucleic acids encoding the at least one CMV antigen, wherein the pharmaceutically acceptable composition, when administered to the subject, elicits an immune response to the cell. The steps (a), (b), and (c) are as described above.

In another aspect, the present invention provides a method of eliciting in a subject an immune response to a cell, the method comprising:

(a) amplifying a nucleic acid molecule from a biological sample from the subject to obtain an amplicon, wherein amplifying comprises contacting the nucleic acid molecule with at least one pair of primers comprising a first primer and a second primer, wherein the amplicon is about 1000 base pairs (bp) or less in length;

(b) determining presence of the amplicon, wherein presence of the amplicon is indicative of CMV nucleic acid in the subject; and (c) administering to the subject a composition comprising an effective amount of antigen presenting cells, T-lymphocytes, or both, wherein the antigen presenting cells and T lymphocytes have been sensitized in vitro with a sensitizing-effective amount of at least one CMV antigen, wherein the effective amount of antigen presenting cells, T lymphocytes, or both is sufficient to elicit the immune response to the cell that expresses the CMV antigen.

In one aspect, the present invention provides a method of reducing or inhibiting growth or spread of a cell that expresses a CMV antigen, the method comprising:

(a) amplifying a nucleic acid molecule from a biological sample from the subject to obtain an amplicon, wherein amplifying comprises contacting the nucleic acid molecule with at least one pair of primers comprising a first primer and a second primer, wherein the amplicon is about 1000 base pairs (bp) or less in length;

(b) determining presence of the amplicon, wherein presence of the amplicon is indicative of CMV nucleic acid in the subject; and (c) administering to a subject a therapeutically or prophylactically effective amount of a pharmaceutically acceptable composition to reduce or inhibit growth or spread of the cell in the subject. The steps (a), (b), and (c) are as described above.

In still further aspects, the present invention provides a method for monitoring the therapeutic efficacy of treating a subject having cells that expresses a CMV antigen, the method comprising:

(a) determining, in a first biological sample from the subject, a first amount of CMV nucleic acid, wherein determining comprises: amplifying a nucleic acid molecule from the biological sample to obtain an amplicon, wherein amplifying comprises contacting the nucleic acid molecule with at least one pair of primers comprising a first primer and a second primer, wherein the amplicon is about 1000 base pairs (bp) or less in length, wherein presence of the amplicon is indicative of CMV nucleic acid in the subject;

(b) treating the subject;

(c) determining, after a suitable period of time, a second amount of CMV nucleic acid in a second sample obtained from the treated subject; and (d) comparing the first amount with the second amount, wherein a difference between the first amount and the second amount is indicative of effectiveness of the treatment.

In some embodiments, the treating in step (b) comprises administering to the subject a therapeutic or prophylactic amount of a pharmaceutical composition as described above.

In other embodiments, the present invention provides assays directed to determining a pharmaceutical agent having activity against a cell that expresses a CMV antigen, the method comprising:

(a) determining, in a first biological sample from the subject, a first amount of CMV nucleic acid, wherein determining comprises: amplifying a nucleic acid molecule from the biological sample to obtain an amplicon, wherein amplifying comprises contacting the nucleic acid molecule with at least one pair of primers comprising a first primer and a second primer, wherein the amplicon is about 1000 base pairs (bp) or less in length, wherein presence of the amplicon is indicative of CMV nucleic acid in the subject;

(b) treating the subject with the pharmaceutical agent;

(c) determining, after a suitable period of time, a second amount of CMV nucleic acid in a second sample obtained from the treated subject; and (d) comparing the first amount with the second amount, wherein the pharmaceutical agent has activity against the cell when the second amount is less than the first amount.

III. Kits

The compositions of the present invention can be supplied in unit dosage or kit form. Kits can comprise various components of the pharmaceutically acceptable composition or vaccines thereof provided in separate containers as well as various other active ingredients or agents including chemotherapeutic agents. For example, the containers can separately comprise at least one CMV antigen or nucleic acids encoding the at least one CMV antigen such that when combined with other components of the kit together constitute a pharmaceutically acceptable composition in unit dosage or multiple dosage form. Preferred kits at least comprise, in separate containers, a source of antigens (e.g., the at least one CMV antigen or nucleic acids encoding them); and one or more adjuvants (e.g., cytokines). The kit can further comprise a physiologically acceptable carrier, diluent, or excipient in a separate container. Optionally, the kit can further comprise a delivery agent such as nanoparticles or transfection reagents. Packaged compositions and kits of this invention also can include instructions for storage, preparation, and administering. One or more nucleic acid primers in accordance with the present invention are optionally included in the kit, preferably provided in one or more separate containers.

The present invention will be illustrated in more detail by way of Examples, but it is to be noted that the invention is not limited to the Examples.

EXAMPLES

Example 1

HCMV Proteins are Expressed in Malignant Gliomas

To determine whether HCMV proteins were expressed in malignant gliomas (MGs), paraffin sections from 45 GBM specimens selected from our brain tumor bank were examined by immunohistochemistry (IHC).

Human GBM, oligodendroglioma, meningioma, ependymoma, and normal brain surgical specimens were obtained in paraffin blocks (with Institutional Review Board [IRB] approval). Tumor specimens were requested based on diagnosis only from the Preston Robert Tisch Brain Tumor Center at Duke Tissue Bank. A total of 45 GBM cases confirmed by a neuropathologist were selected (36 primary GBM and 9 recurrent GBM). The group consisted of 26 males and 19 females, with a median age of 51 years. Specimens were sectioned (6 µm) and were blocked for endogenous peroxidase (3% $H_2O_2$, for 12 min) and incubated with Fc receptor blocker (10 min at 20° C.; Innovex Biosciences, Richmond, Calif., USA) before the addition of a monoclonal antibody (mAb). IHC was performed using three-stage horseradish peroxidase detection systems (BioGenex, San Ramon, Calif., USA; Dako, Carpinteria, Calif., USA; and Innovex Biosciences) with the following mAbs: anti-IE1-72 (1:25; BioGenex), anti-pp65 (1:30; Novocastra, Newcastle upon Tyne, UK), and antismooth muscle actin (1:15; BioGenex). Antibody parameters (e.g., postfixation, retrieval, and incubation time) were established for each mAb using DAB (Innovex Biosciences) as chromogen. Primary glioma cultures established for 14 to 21 days from freshly resected GBM specimens were fixed and permeabilized using cold methanol, followed by postfixation for 10 min with 10% neutral buffered formalin. Blocking of nonspecific binding was conducted using biotin block and avidin block (BioGenex) and FC receptor blockade (Innovex). Incubation with primary antibodies using isotype controls (mouse IgG1, mouse IgG2a; Invitrogen, Carlsbad, Calif., USA), CD45 antibody (BD Biosciences, San Jose, Calif., USA), pp28 antibody (Virusys, Sykesvile, Md., USA), glycoprotein B (gB; Virusys), and HIV p17 (Virogen, Watertown, Mass., USA) was conducted for 2 h or overnight at 4° C. (1 µg/ml antibody concentration) and detection conducted using BioGenex three-stage horseradish detection system.

Figure 1B:
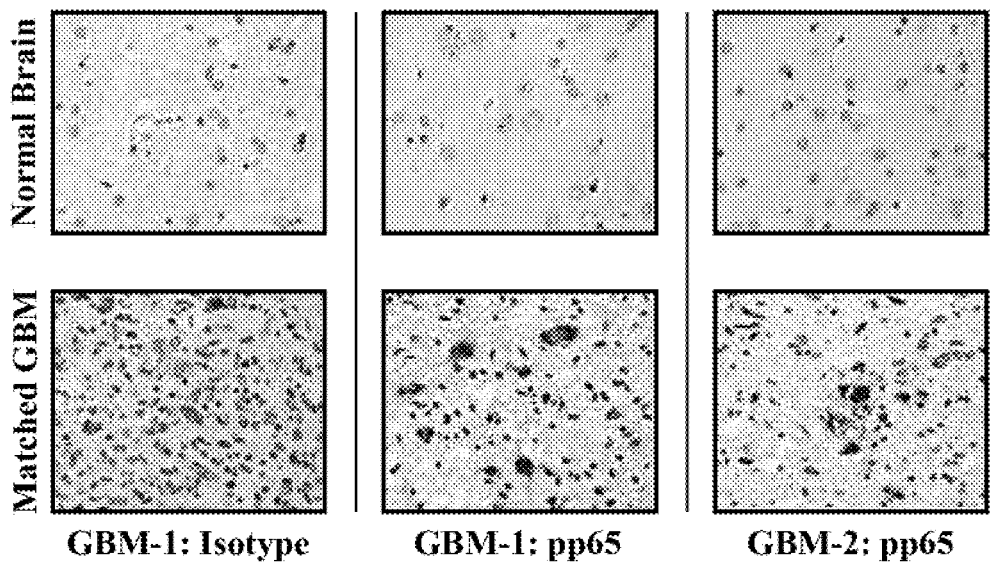

Detection was conducted using a mAb specific for the HCMV-encoded antigen, IE1-72. IE1-72 immunoreactivity was detected in 42 out of 45 (93%) specimens examined by IHC. Strong nuclear and cytoplasmic staining was detected in tumor cells and occasionally endothelial cells as well (FIG. 1). However, infiltrating lymphocytes and surrounding normal brain areas were devoid of immunoreactivity to the IE1-

72 antibody. To further confirm specific detection of HCMV, 33 of the 45 cases were examined for reactivity to a mAb specific for the HCMV matrix protein, pp65. Thirty of the 33 cases (91%) were immunoreactive for pp65 in the tumor cells but not in areas of adjacent normal brain. pp65 reactivity was in general less ubiquitous than IE1-72 detection in tumor cells, but a majority of tumor cells in all specimens examined displayed immunoreactivity against the pp65 antibody (FIG. 1; Table 3).

TABLE 3

Summary of HCMV detection in GBM specimens

| HCMV | GBM Tissue Specimen | Primary GBM Cultures |
|---|---|---|
| IE1 IHC | 42/45 (93%)[a] | 4/4 (100%) |
| pp65 IHC | 30/33 (91%)[a] | 12/12 (100%) |
| HCMV DNA ISH | 16/16 (selected cases) | not tested |
| gB PCR | 21/34 (61.7%)[b] | 13/17 (70.6%) |
| IE1 PCR | 8/34 (24%)[b] | 9/17 (53%) |

Abbreviations:
HCMV, human cytomegalovirus;
GBM, glioblastoma multiforme;
IHC, immunohistochemistry;
ISH, in situ hybridization;
gB, glycoprotein B;
PCR, polymerase chain reaction.
[a]Other tumors tested by IHC were negative for HCMV: oligodendroglioma (n 5 = 5); one case exhibited focal detection of HCMV IE1 in endothelial cells but no reactivity within tumor parenchyma); meningioma (n = 5); ependymoma (n = 5).
[b]PCR products were isolated from 21 gB PCR reactions and 6 IE1 PCR and confirmed by DNA sequencing to be specific for HCMV.

To rule out the possibility of nonspecific detection in tumor cells, IHC was performed on tumor sections with isotype- and concentration-matched control mAbs. Isotype-matched, control antibodies used at identical concentration to the HCMV-specific mAbs showed no immunoreactivity within tumor cells, and an isotype-matched mAb to smooth muscle actin demonstrated reactivity to blood vessels within tumor and normal brain sections (FIG. 1A) but no reactivity with tumor cells. Examination results of meningiomas (n=5), ependymomas (n=5), and oligodendrogliomas (n=5) were negative for detection of IE1 and pp65, except for focal endothelial staining observed in a single case of oligodendroglioma with the IE1 monoclonal antibody (Table 3).

Example 2

PCR Detection of HCMV in Malignant Glioma Specimens

Figure 2:
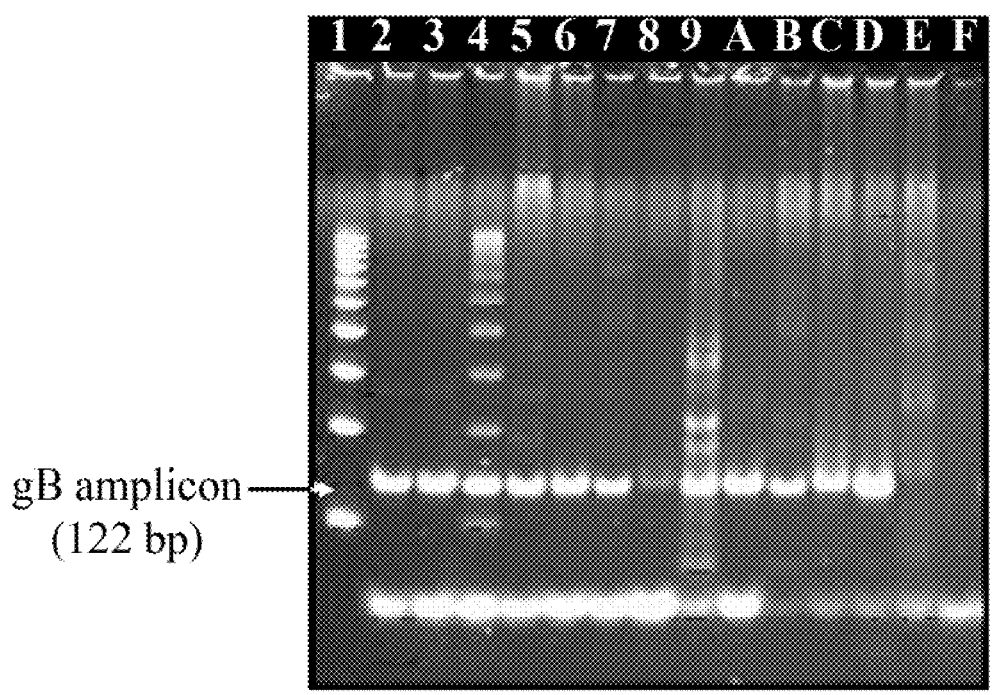
FIG. 2 shows polymerase chain reaction (PCR) detection of HCMV in malignant glioma specimens. Lane 1: 100 bp ladder, Lanes 2-E: MG specimens; Lane 4: MG sample 4+100 bp ladder; Lane F: negative control (no DNA template).

As shown in FIG. 2, PCR amplification of gB in 11/13 high grade MGs (9/11 GBMS, 2/2 AAs) was performed. Forty cycles of PCR were conducted using gB specific primers to amplify a 122 bp product. HCMV gB was sequence verified in 17 of 32 positive samples.

Example 3

CMV Antigens are Present in Pre-Malignant Lesions

The presence of CMV IE1 and pp65 proteins in greater than about 75% of premalignant colorectal polyps and greater than about 80% of adenocarcinomas of the colon but not in adjacent non-neoplastic colon biopsy samples are shown (See, e.g., Harkins et al., Lancet, 360:1557 (2002)). Furthermore, the presence of CMV in about 48% of low grade gliomas, which frequently progress to high grade lesions, is shown (See, e.g., Scheurer et al., Detection of Human Cytomegalovirus in Different Histological Types of Gliomas, Acta Neuropathologica, Epublished Mar. 20, 2008, Springer Berlin/Heidelberg). Thus, the compositions and methods of the present invention also can provide for preventing or treating pre-neoplastic, low-grade, and/or pre-malignant lesions as well as progression to neoplastic disease.

Example 4

Ex Vivo Generation of Autologous DC

Contents of a Leukapheresis Product (LP) bag was placed in a 1 L sterile corning bottle and an equal volume of phosphate buffered saline (PBS) was added to dilute the LP. Using centrifuge tubes, 20 mL of Histopaque™ (Sigma #1077-1) was gently over layered with 30 mL of the diluted LP, then spun at 1300×g for 25 minutes. The interface (1 interface per tube) was removed; PBS was added to 50 mL; and cells pelleted for 5 minutes at 500×g room temperature (RT). The supernatant was decanted and the pellet was resuspended in 50 mL PBS, then pelleted as above. The supernatant was decanted and 2 pellets were combined in 50 mL PBS, then pelleted as above. Again, the supernatant was decanted and 2 pellets were combined in 50 mL PBS, then pelleted as above. Pellets were combined and washed with PBS until all of the cells were combined into 1 tube.

Trypan blue exclusion was performed to determine the number of live and dead cells via with the aid of a hematocytometer. The cells were resuspended in AIM V media (Life Technologies #870112dk) with 2% Human AB Sera (HABS) (Valley Biomedical #HP1022) at $2 \times 10^8$ per mL. Twenty-nine mL of AIM V media containing 2% HABS and 1 mL of PBMC cell suspension were added to a T-150 cell culture flask. All cell culture flasks were placed into a single dedicated humidified incubator at 37° C., 5% $CO_2$ for 2 hours to allow the monocyte precursors to adhere. Following the adherence period, non-adherent cells were removed and the remaining monolayer was washed once with PBS. The adherent cells were replenished with 30 ml of AIM-V per flask supplemented with 800 U/mL recombinant human GM-CSF (Berlex Laboratories, Inc.) and 500 U/mL recombinant human IL-4 (R&D Systems #204-IL/CF), and incubated in humidified incubator at 37° C., 5% $CO_2$ for 7 days.

After the 7-day culture period, adherent DCs were washed with cold PBS. Ten ml of Dissociation Buffer Enzyme-Free (Life Technologies #13150-016) was added and the DCs were incubate at 4° C. for 10 minutes. The remainder of adherent DC were flushed from the flask and combined with previously harvested DC, then pelleted at 500×g for 10 minutes at 4° C. Following one wash with cold PBS, the cells were checked for number and viability.

Example 5

RNA Loading & Maturation of Dendritic Cells

Dendritic cells generated as described above were resuspended at $2.5 \times 10^7$ cells per mL of ViaSpan (Belzer UW-CSS, DuPont Pharmaceuticals, Wilmington, Del.). Two hundred μL of the suspension was then placed in a cuvette (Gene Pulser Cuvette, Bio-Rad #165-2086) along with 10 μg of pp65 RNA and the cells were electroporated (BTX Electro Square Porator #ECM830) at 300 volts for 500μ seconds. Approximately $1 \times 10^8$ of the electroporated cells were transferred to a T225 flask containing 50 mL of AIM V supplemented with 800 U/mL of recombinant human GM-CSF (Berlex Laboratories, Inc.) and 500 U/ml recombinant human IL-4 (R&D Systems #204-IL/CF), then incubated at 37° C., 5% $CO_2$ for 1 hour. At the end of the incubation period, the appropriate amount of media with maturation cytokine was added to a final concentration of the cytokines in the maturation cocktail of 10 ng/ml TNF-α (R&D Systems, #210-TA/CF); 10 ng/ml IL-113 (R&D Systems, #201-LB/CF); and 1000 units/ml IL-6 (R&D Systems, #208-IL/CF). The cells were incubated overnight at 37° C. and 5% $CO_2$.

At the end of the maturation period, the supernatant was removed and placed in chilled 50 ml conical tube on ice. The remaining monolayer was washed with ice cold PBS; combined with supernatant; then pelleted at 500×g for 5 minutes 4° C. The pellet was resuspended in 10 ml of ice cold PBS and kept on ice. Ten to 20 ml of Dissociation Buffer Enzyme-Free (Life Technologies #13150-016) was added and the cells kept at 4° C., and the progress of the cells coming off was monitored every 5 minutes. The flask was washed twice with 10 ml of ice cold PBS, combined with the cells from the dissociation buffer, and pelleted using 500×g. The cells were combined with the other cells, and brought up to 50 ml and counted.

Example 6

Preparation of Dendritic Cells for Vaccination

Mature antigen-loaded dendritic cells in a 50 mL conical centrifuge tube and 25 ml of PBS was slowly add, then the cells were pelleted at 200×g for 5 minutes at 22° C. The cells were resuspended in 10 ml of PBS and, using a 2 ml pipette, a 100 μl sample of the suspension was removed and the cells counted using a hemocytometer and trypan blue as described above. Cells were determined to be ≧70% viable before proceeding. Cells were pelleted at 500×g for 5 min at 22° C. and resuspended at $5 \times 10^4$ cells/mL in 0.9% sodium chloride. The cells were loaded into a 1 cc syringe with 25 G ⅝ gauge needle. Samples were sent for Gram stain and endotoxin testing prior to administration.

Example 7

Figure 3:
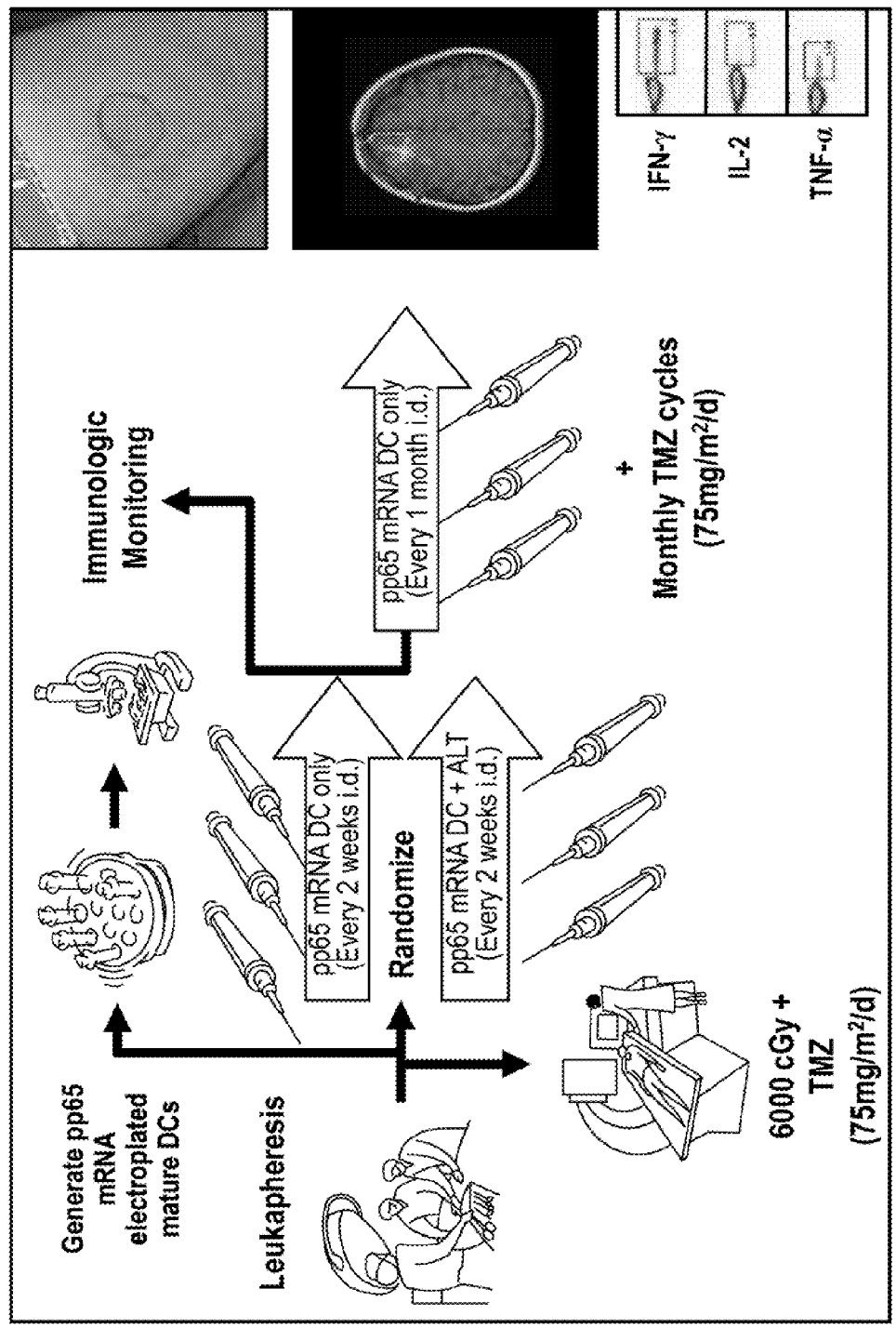
FIG. 3 shows a schematic depiction of a vaccination protocol for subjects with newly-diagnosed GBMs using CMV pp65-LAMP RNA-loaded DCs during recovery from therapeutic TMZ-induced lymphopenia with or without autologous Lymphocyte transfer (ALT) in subjects that are seropositive and seronegative for CMV.

Vaccinating Subjects with Newly-Diagnosed GBMs Using CMV pp65-LAMP RNA-Loaded DCs Twenty-five patients (with ≧3 CMV seropositive patients in each randomized group) with newly diagnosed GBM are enrolled within 6 weeks of resection. Only 1 dose level of DCs ($2 \times 10^7$) and 1 dose level of ALT ($3 \times 10^7$/Kg) is assessed. The decision to dose escalate in subsequent trials is dependent on analysis of the safety and immunologic responses obtained in this trial. Patients are followed until death. The study is halted if any 2 patients in either group experience a drug-related Grade IV or irreversible Grade III toxicity. All patients undergo a leukapheresis after resection for harvest of PBLs for ALT and generation of DCs. FIG. 3 schematically illustrates the vaccination protocol.

Patients receive radiation therapy (RT) and concurrent TMZ at a standard targeted dose of 75 mg/m²/d. Patients with progressive disease during radiation and that are dependent on steroid supplements above physiologic levels at time of vaccination, unable to tolerate TMZ, and whose DCs or PBLs fail to meet release criteria, are replaced. Remaining patients then receive the initial cycle of TMZ at a standard targeted dose of 200 mg/m²/d for 5 days 3±1 weeks after completing RT and are randomized to receive ALT or not simultaneous with DC vaccine #1. DCs are given intradermally and divided equally to both inguinal regions. Vaccine #2 and #3 occurs at 2 week intervals. All patients undergo leukapheresis again for immunologic monitoring with specific assessment of baseline antigen-specific cellular and humoral immune responses and further DC generations 4±2 weeks after vaccine #3. Patients are then vaccinated monthly in conjunction with subsequent TMZ cycles every 5±1 weeks for a total of 6 cycles after RT. TMZ is given on days 1-5 with DCs given on day 21±7 days. DC vaccinations continue after TMZ cycles are finished.

Patients are imaged bimonthly without receiving any other prescribed anti-tumor therapy and continue with vaccinations until progression. Patients undergo an additional leukapheresis for generation of DCs if needed to continue vaccinations. At vaccine #4, patients are randomized to different skin preparations at the inguinal sites and receive $^{111}$In-labeled DCs to compare the effects of different skin preparations on DC migration. When progression occurs, patients receive final intradermal vaccinations bilaterally in the inguinal region and at the angle of the jaw with $^{111}$In-labeled DCs to compare the effects of different vaccination sites on DC migration. As part of standard care for these patients, upon tumor progression, participants may undergo stereotactic biopsy or resection. As this is not a research procedure consent is obtained separately. However, if tissue is obtained, it is used to confirm tumor progression histologically and to assess immunologic cell infiltration and pp65 antigen escape at the tumor site.

Study inclusion criteria include: age >18 years of age; GBM (WHO Grade IV) with definitive resection <6 weeks prior to enrollment, with residual radiographic contrast enhancement on post-resection CT or MRI of <1 cm in maximal diameter in any axial plane; and Karnofsky Performance Status (KPS) of >80% and a Curran Group status of I-IV.

Study exclusion criteria include radiographic or cytologic evidence of leptomeningeal or multicentric disease at any time prior to vaccination; prior conventional anti-tumor therapy other than steroids, RT, or TMZ; pregnant or need to breast feed during the study period (Negative β-HCG test required); requirement for continuous corticosteroids above physiologic levels at time of first vaccination; active infection requiring treatment or an 101.5° unexplained febrile (>101.5° F.) illness; known immunosuppressive disease or human immunodeficiency virus infection; patients with unstable or severe intercurrent medical conditions such as severe heart or lung disease; allergic or unable to tolerate TMZ for reasons other than lymphopenia; or patients with previous inguinal lymph node dissection.

Exemplary procedures that are investigational include: leukapheresis for the generation on DCs and ALT; intradermal immunizations with antigen loaded DCs; ALT; intradermal immunization with $^{111}$In labeled antigen loaded DCs and SPECT scans; and DTH testing with standard recall antigens and antigen loaded and naïve DCs.

Activities associated with the protocol that are considered standard care activities include: external beam radiotherapy; Temozolomide (TMZ); MRI; and biopsy at recurrence.

Patients receive their own lymphocytes intravenously (through a catheter placed in your vein) after pre-medication with Benadryl 25-50 mg and 650 mg of Tylenol to prevent infusion reactions. Transfusion is received over 45 to 90 minutes depending upon weight and the number of cells received. The probability of risk of infection is relatively low, given the small injection volume (1 mL divided between >2 intradermal locations) and the fact that the DCs are strictly tested for sterility prior to each injection. The risk of infection due to potential contamination of the DCs in the laboratory is minimized by biosafety quality assurance and testing. All cell cultures are handled under sterile conditions in a core tissue culture facility dedicated to the processing of human cells.

Prior to injection into patients, DCs pass sterility tests in thighlycolate broth, tryptic soy blood agar, and inhibitory Sabouraud agar. Following injections, patients are monitored throughout the course of the study for any signs and symptoms of infection. If an active infection is suspected, patients are cultured and treated with appropriate antibiotics.

Patients' DCs are radiolabeled with $^{111}$In for correlative studies. The radiation exposure to the patient and health care personnel is minimal at the proposed doses, and is roughly equivalent to living in a high altitude city such as Denver for 13 days, or taking 4 airplane flights from New Your to Los Angeles. Therefore, no specific radiation precautions are taken. SPECT images are obtained for analysis.

During the MRI, patients are given a contrast agent. The agent is given routinely to obtain enhanced MRI scans of the brain. The agent is administered through the vein and requires the placement of an IV catheter. The catheter placement is similar to drawing blood except that the catheter remains in the vein during the time the agent is actively delivered.

Example 8

Time to Tumor Progression (TTP) is Increased for Patients with Newly-Diagnosed GBM Treated with CMV pp65 RNA Loaded DCs DCs were generated from a leukapheresis in vitro by 7-day culture with GM-CSF and IL-4. For in vitro generation of DCs, PBMCs were obtained by leukapheresis and transported to a cell processing facility. For patients without sufficient venous access for leukapheresis a temporary intravenous catheter was inserted.

At the end of the 7 day incubation for generating DCs a sample of the media was taken for mycoplasma testing, and the cells were then harvested and electroporated with pp65-LAMP mRNA (2 micrograms RNA per million DCs). The DCs were placed in a flask with AIM V media with GM-CSF+IL-4+TNF-α+IL-6+IL-1β at 37° C., 5% $CO_2$ for 18-20 hours for maturation. The cells are washed twice with PBS and frozen at $5 \times 10^6$ cells/mL in 90% autologous human AB serum (Valley Biomedical, Winchester, Va. 22602), 10% DMSO and 5% glucose in a controlled-rate freezer at a rate of 1° C./minute. The DCs were then stored until needed at −135° C. After freezing, an aliquot of cells was thawed and sent for aerobic and anaerobic bacterial cultures ($1 \times 10^6$ DCs) and fungal cultures ($1 \times 10^6$ DCs).

For each vaccination, DCs were rapidly thawed at 37° C., washed three times with PBS, assessed for viability, and counted. To proceed, a cell viability of ≧70% was obtained. The cell concentration was adjusted to $4 \times 10^7$ cells/mL and DCs were resuspended in preservative free saline and placed into a sterile tuberculin syringe with a 27 gauge needle.

For all DC preparations, a sample of cells was sent for Gram stain and endotoxin testing prior to administration. DC vaccination was not given until endotoxin testing passed (<5.0 E.U./Kg) and the Gram stain was negative. An aliquot of cells also was sent for aerobic and anaerobic bacterial cultures ($1 \times 10^6$ DCs) and fungal cultures ($1 \times 10^6$ DCs).

A Phase I/II clinical trial using autologous pp65 RNA loaded DCs was initiated. This trial has enrolled 21 patients with newly diagnosed GBM who underwent gross total resection (>95%) followed by standard external beam radiation (60 Gy) and concurrent TMZ (75 mg/m²/d) for six weeks followed by monthly 5 day TMZ (150-200 mg/m²/d) for six cycles. Five patients progressed during radiation and were not treated on protocol. Two patients were treated off-protocol on a compassionate-use basis. Leukapheresis harvested post surgical resection and prior to initiation of TMZ was used to generate DCs and pp65 RNA electroporated autologous DCs ($2 \times 10^7$ DCs i.d.) were administered every two weeks for first three doses after first TMZ cycle and monthly thereafter on day 21 of each cycle. Patients were monitored by MRI (every two months) for tumor progression and blood collected monthly for immunologic monitoring. Controls are age, prognostic factor matched with identical eligibility criteria to patients enrolled on ATTAC trial derived from MD Anderson database.

Figure 4:
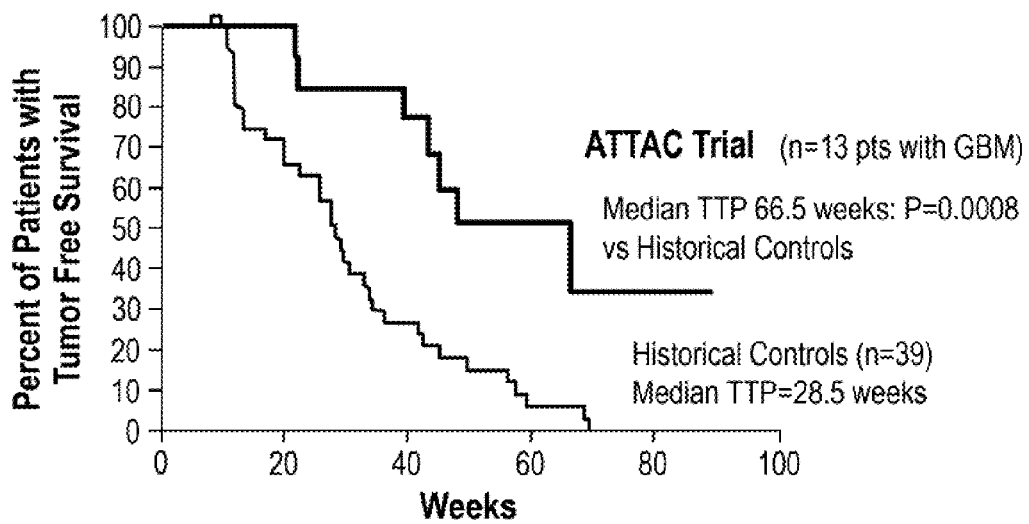
FIG. 4 is a graph showing time to progression for patients with newly-diagnosed GBM treated with CMV pp65 RNA loaded DCs. Thirteen patients with GBM were treated with DC vaccines targeting CMV pp65. Time to progression is favorable compared to historical controls (P=0.0008).

The results are shown in FIG. 4. At follow-up of 21 months, 13 of 16 patients remained alive (range 7.6 months to 22 months post surgery) with a median TTP of 12.5 months and median overall survival has not been reached but is greater than 20.1 months, which is highly favorable compared to historical controls (see, e.g., Stupp et al., N. Engl. J. Med. 352:987 (2005); Phase III TMZ/XRT+adjuvant TMZ median TTP is 7.1 months and median survival 14.6 months).

Example 9

Overall Survival is Increased for GMB Patients Treated with CMV pp65 RNA-Loaded DC Vaccine Following completion of RT with concurrent daily TMZ (75 mg/m²/d), patients were randomized to those that received DC vaccinations only and those that received ALT along with the first DC vaccination. Randomization was stratified by CMV serology status and assignments were made from a pool of consecutive sealed envelopes which had been prepared by the study statistician, using a random number generator. DC vaccinations began along with the first 5 day cycle (days 1-5) of TMZ (200 mg/m²). On day 21±2 of the TMZ cycle, both patient groups received an intradermal immunization every 2 weeks for a total of three immunizations with $2 \times 10^7$ pp65-LAMP mRNA loaded mature DCs. Each immunization was divided equally to both inguinal regions. A total volume of 200 μL per side was delivered intradermally (SOP-JHS-HDC-CL-012 "Intradermal Administration of Dendritic Cells Procedure"). Details of the procedure were recorded on the appropriate form (FORM-JHS-HDC-CL-012). Injection was performed using a 1.5 inch 25 gauge needle. Patients were monitored in the clinic for thirty minutes to one hour post-immunization for the development of any adverse effects. The immunization procedures were supervised by a nurse or physician that had completed an Advanced Cardiac Life Support (ACLS) course. A cardiac resuscitation cart was available in the immediate vicinity when performing these immunizations in the event of severe allergic reactions. The initial three vaccines were given each 2±1 week apart.

After the third vaccine, patients underwent a 4-hour leukapheresis for immunologic monitoring and DC generation. Subsequently, patients were immunized on day 21±2 of every cycle of TMZ which was delivered every 5±1 weeks. Thus, in addition to the concurrent TMZ (75 mg/m²/d) given with radiation, a total of 6 addition cycles of TMZ (200 mg/m²/days 1-5) was given.

If the TMZ cycles were completed without progression, DC vaccinations continued every 5±1 weeks until clinical or radiographic progression without any additional prescribed anti-tumor therapy. During that time period, patients were monitored clinically with routine physical and neurologic examinations and MMSE testing at every visit and with a contrasted-enhanced CT or MRI every 8±4 weeks. Peripheral blood was obtained at each visit as well immunologic monitoring.

A phase II randomized, prospective clinical trial was undertaken to assess the immunogenicity and efficacy of targeting the immunodominant CMV integument protein, pp65, in patients with newly-diagnosed GBM using pp65-RNA transfected dendritic cells (DCs). After resection and radiation with concurrent TMZ (75 mg/m$^2$/d), patients received subsequent monthly cycles of TMZ (200 mg/m$^2$) simultaneous with intradermal vaccinations and were randomized to receive an ALT (3×10$^7$/Kg) prior to vaccination. Subjects received vaccinations until there was evidence of tumor progression.

Figure 5:
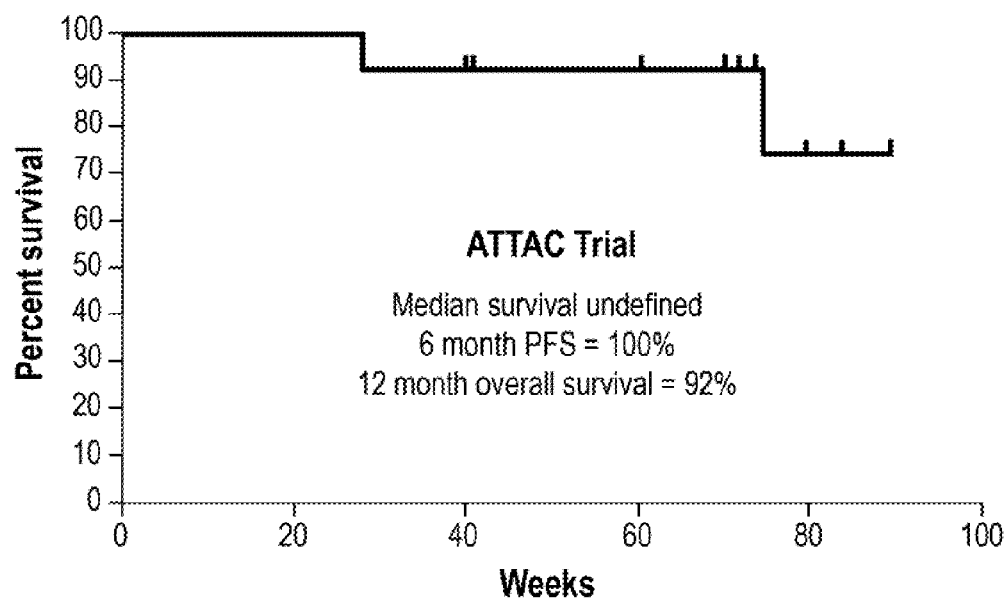
FIG. 5 is a graph showing overall survival of patients with GBM treated with CMV pp65 RNA loaded DC vaccines.
Figure 6:
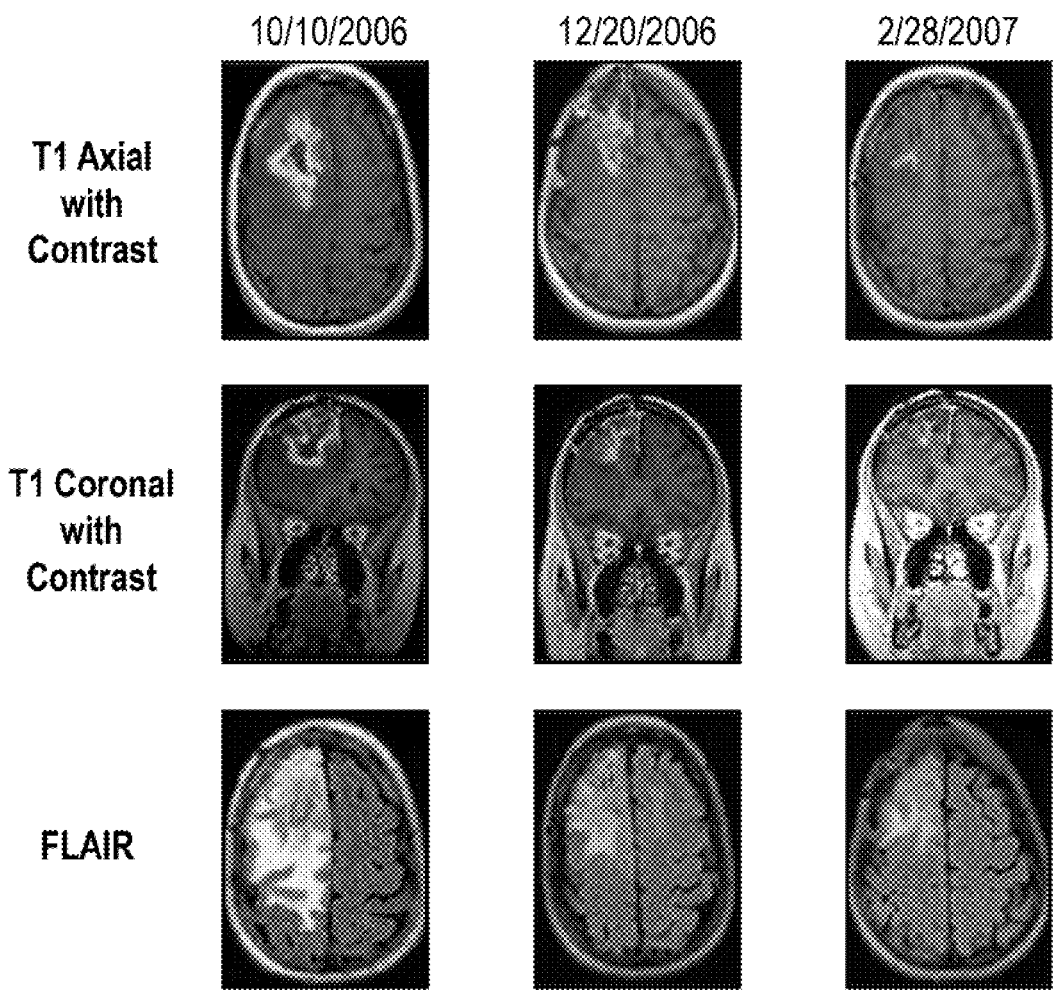
FIG. 6 is a magnetic resonance image (MRI) showing near complete radiographic response during pp65 RNA loaded DC vaccination for a 33 year-old female subject with GBM.

The results are shown in FIG. 5. Twenty-one patients were consented. Five progressed during radiotherapy. There were no vaccine-related, reportable serious adverse events (SAEs). TMZ therapy, however, induced Grade 3 lymphopenia (500 cells/mL) in 70% of patients after the first TMZ cycle. After TMZ, immunosuppressive regulatory T cell (T$_{Reg}$) (CD4$^+$ CD25$^{++}$CD45RO$^+$CD127$^-$FOXP3$^+$) levels increased from 5.2% (3.3-7.5) to 11.8% (6.9-13.8) (P=0.0004; paired t-test). One nearly complete response was observed. Median PFS was 12.5 months (CI$_{95}$: 10.0, ∞). Overall survival of patients with GBM treated with CMV pp65 RNA loaded DC vaccines is favorable. 6 PFS (100%; 13 of 13 pts), 12 month survival (92.3%; 12 of 13 pts), and 15 month survival (90%; 9 of 10 pts) compare favorably to patients with similar diagnosis (see, e.g., Temodar® (63.7 weeks) (Stupp et al., N Engl J Med., 352:987 (2005); and Gliadel™ (59.6 weeks) (Westphal et al., Neuro Oncol., 5:79-88 (2003)). Overall median survival is greater than 19.7 months. As shown in FIG. 6, a 33 year-old female with GBM had nearly complete radiographic response to CMV pp65 RNA-loaded DC vaccine combined with autologous lymphocyte transfer. MRIs showed decrease in enhancing lesion, correction of midline shift, and resolution of neurologic symptoms. This patient remained alive and well at 21 months post primary surgical resection of GBM.

Figure 7:
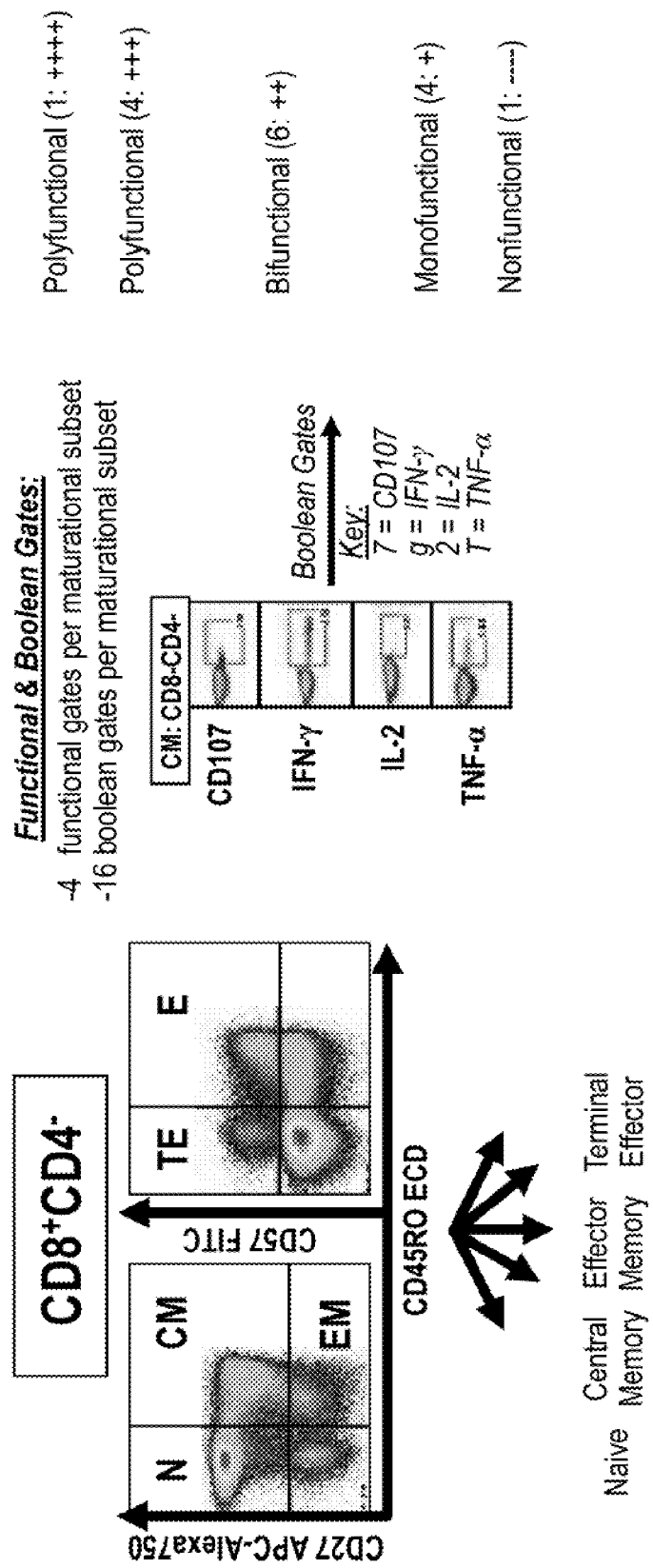
FIG. 7 shows analysis of polyfunctional T cell responses to CMV pp65. Peripheral blood mononuclear cells (PBMCs) from a CMV seropositive donor were stimulated in vitro with CMV pp65 peptide mix and analyzed using a validated 11-color polychromatic flow cytometric analysis in the Immunologic Monitoring Core laboratory of the HIV Vaccine Trials Network. Functional and Boolean gating software was used to determine the proportion of polyfunctional T cells (secreting multiple cytokines and displaying granzyme activation marker CD107a). Polyfunctional immune responses have been shown to distinguish progressors versus non-progressors with HIV infection and have correlated better with immune protection in viral infection than absolute numbers or percentages of cells secreting a particular cytokine.
Figure 8:
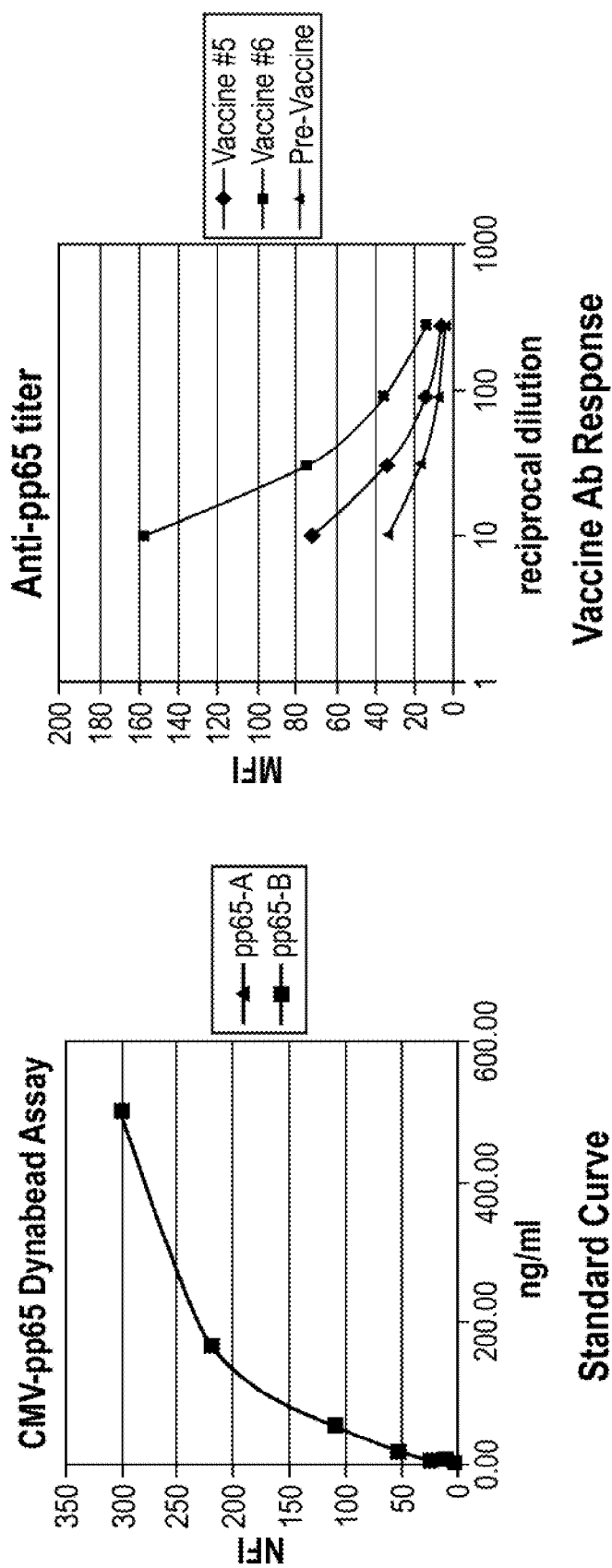
FIG. 8 is a graph showing increase in pp65 antibody response in a patient with newly-diagnosed GBM receiving vaccination with autologous dendritic cells pulsed with pp65 mRNA. The panel on the left shows standard curve binding of a pp65-specific monoclonal antibody to beads coated with recombinant pp65 protein. The right panel shows specific binding of antibodies present in dilutions of a patient's serum to beads coated with recombinant pp65. Pre-vaccine serum contains low titer of pp65-specific antibody and increasing titer (shown as mean fold increase (MFI) after detection with anti-human IgG fluorescent antibodies) at vaccine #5 and further increase by vaccine #9. Furthermore, these responses were induced during cycles of temozolomide, demonstrating the capacity to induce potent humoral responses during concurrent chemotherapy administration.
Figure 9:
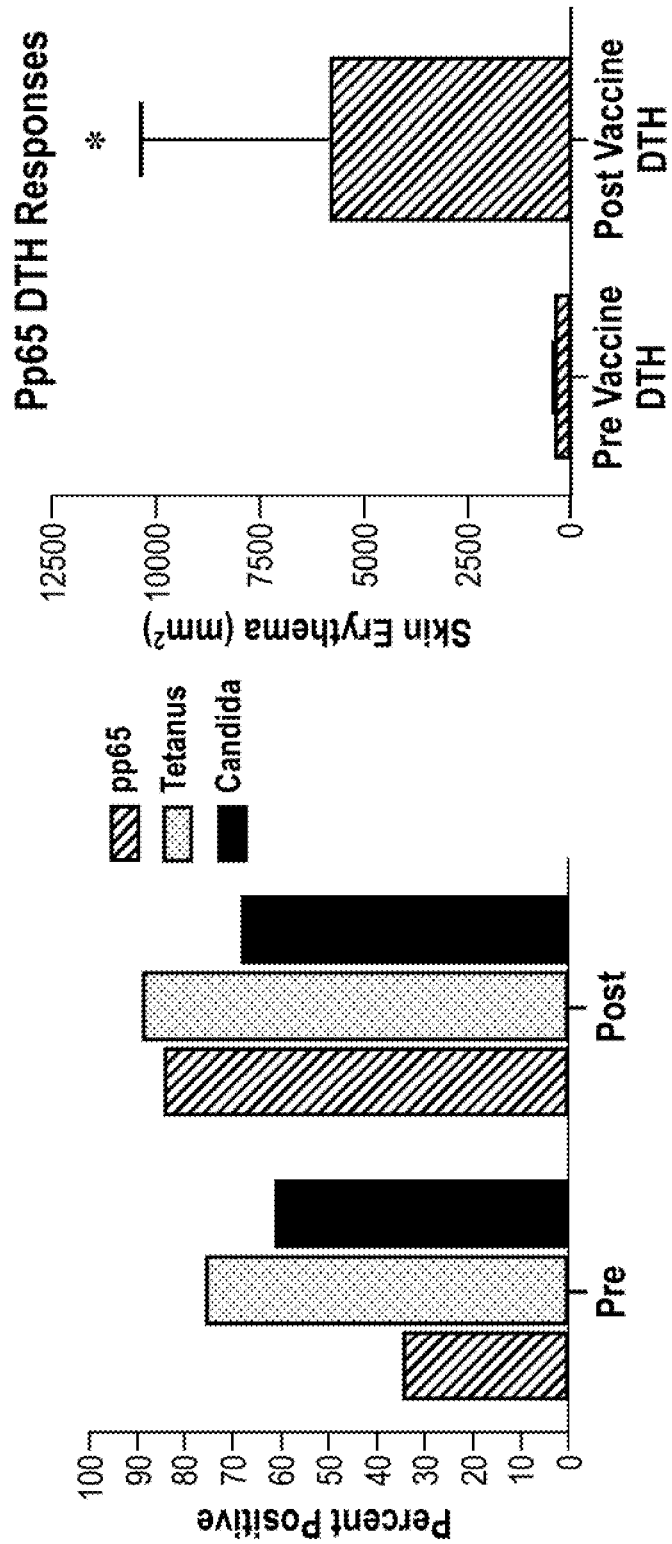
FIG. 9 is a bar graph showing increase in delayed-type hypersensitivity (DTH) responses in patients with newly-diagnosed GBM receiving vaccination with autologous dendritic cells pulsed with pp65 mRNA. The proportion of patients demonstrating a positive DTH response ($\geq 10$ mm$^2$) prior to and after vaccination to pp65 and control antigens (tetanus and *Candida*) is shown on the left; and area of skin erythema prior to and after vaccination is shown on the right. Furthermore, these responses were induced during cycles of temozolomide, demonstrating the capacity to induce cellular DTH responses during concurrent chemotherapy administration.

Preliminary results of CMV-specific polyfunctional cellular and humoral immune responses show that patients with GBM have CMV-specific immunologic deficiencies (FIGS. 7-9).

Example 10

Antigen-Specific CD8+ and CD4+ T Cells can be Separated from Bulk Culture Responding to CMV pp65 Antigen-Pulsed DCs To identify and isolate polyclonal populations of antigen-specific CD4+ and CD8+ T cells, green fluorescent protein (GFP) RNA electroporation was conducted on T cells stimulated with DCs transfected with mRNA encoding the full-length pp65 antigen of CMV. Dendritic cell generation, antigen loading with peptide and RNA, and maturation of dendritic cells:

All cellular materials used in these experiments were obtained from normal volunteers and patients with malignant glioma after informed consent had been given, under the approval of the Duke University Institutional Review Board. Peripheral blood mononuclear cells (PBMCs) were obtained by leukapheresis and incubated for 1 hr in AIM-V medium (Invitrogen Life Technologies, Grand Island, N.Y.) at 37° C. to allow adherence to plastic and then cultured for 6 days in AIM-V medium supplemented with granulocyte-macrophage colony-stimulating factor (800 units/ml) and IL-4 (500 units/ml). Immature dendritic cells were harvested on day 6, washed, and resuspended in Opti-MEM (Invitrogen Life Technologies) at 2.5×10$^7$/ml. The supernatant from DC culture was saved as conditioned medium for later use. Cells were electroporated in 2-mm cuvettes: 200 μl of DCs (5×10$^6$ cells) at 300 V for 500 μsec, using a square waveform generator (ECM 830 Electro Square Porator; BTX, a division of Genetronics, San Diego, Calif.). DCs were electroporated with 2.5 μg of RNA per 10$^6$ cells. Cells were transferred to 60-mm tissue culture Petri dishes containing a 1:1 combination of conditioned dendritic cell growth medium and fresh medium. Cells were matured overnight with IL-1β (5 ng/ml), tumor necrosis factor-α (5 ng/ml), IL-6 (150 ng/ml), and prostaglandin E$_2$ (1 μg/ml). IL-4, tumor necrosis factor-α, IL-1β, and IL-6 were obtained from R&D Systems (Minneapolis, Minn.); granulocyte-macrophage colony-stimulating factor was from the pharmacy at Duke University Medical Center (Durham, N.C.) and prostaglandin E$_2$ was from Pharmacia (Erlangen, Germany). For peptide stimulation, mature dendritic cells were washed and resuspended in 1:1 conditioned medium and fresh medium with a 10 μg/ml concentration of the HLA-A2-restricted immunogenic human cytomegalovirus pp65 peptide NLVPMVATV (pp65$_{495-503}$) (SEQ ID NO:109) (AnaSpec, San Jose, Calif.).

Pulsing of Dendritic Cells with pp65 Peptide or mRNA and Activation of T Cells:

DCs were generated from HLA-A2$^+$ normal volunteers and patients with malignant glioma and pulsed with pp65 peptide (10 μg/ml) in AIM-V medium-2% human AB serum for 3 hr at 37° C. For loading with mRNA encoding pp65, DCs were washed and resuspended in Opti-MEM for electroporation. Two micrograms of mRNA encoding full-length HCMV pp65 per 1×10$^6$ DCs was electroporated with the BTX ECM 830. DCs were washed once with 45 ml of AIM-V medium and autologous responder lymphocytes were added at a 1:10 ratio (DC:T cells). Volumes were adjusted to 2×10$^6$ cells/ml and cells were incubated at 37° C. in a humidified atmosphere containing 5% CO2. After 3 days, an equal amount of AIM-V medium with 2% pooled human AB serum plus IL-2 (10 U/ml) was added and cells were transferred to 24-well plates at a volume of 1 ml/well. Thereafter, every 2-3 days, cells were evaluated for growth and adjusted to 1×10$^6$ cells/ml. After 8 to 11 days of coculture with pp65-pulsed DCs, the T cells were harvested and electroporated with mRNA encoding GFP. Alternatively, T cells were stimulated by polyclonal stimulation using immobilized anti-CD3 monoclonal antibodies (Ortho Biotech, Raritan, N.J.) (2 μg/ml in phosphate-buffered saline [PBS] overnight in a T-150 flask). Cells were plated in AIM-V medium with 2% human AB serum (10$^6$ cells/ml) in CD3-coated plates and cultured for 3 to 5 days before harvesting.

Source of T Lymphocytes:

Nonadherent (NA) cells were generated from PBMCs from patients with malignant gliomas and normal volunteers under Duke University Institutional Review Board approval after informed patient consent was given. Mononuclear cells from peripheral blood were isolated by Ficoll-Hypaque gradient separation (LSM; MP Biomedicals, Solon, Ohio). Electroporation of DC-pulsed pp65 peptide-stimulated T cells with GFP:

The mRNA encoding GFP was prepared from the PGEM4Z/GFP/A64 vector (kindly provided by E. Gilboa, Duke University Medical Center) as previously described (Zhao et al., Blood, 102:4137 (2003)). DCs pulsed with pp65 peptide were used to stimulate autologous T cells as described above. The cells were kept in medium with 10 U/ml of IL-2 and incubated for 7 days at 37° C. For electroporation, 0.2 ml of the cell suspension (5×10$^6$) was mixed with 10 μg of in vitro-transcribed GFP mRNA. The mixtures were electroporated in 0.4-cm cuvettes (EquiBio; PEQLAB Biotechnologie, Erlangen, Germany) at 300 V and 150 Mf, using an electroporation device. After electroporation, the cells were cultured in fresh AIM-V medium supplemented with 2% human AB serum and incubated overnight. Twenty-four hours after electroporation, the cells were harvested and stained for CD8 and HLA-A2 tetramer positivity and analyzed by flow cytometry.

Expansion of Sorted T Cells:

Using the same stimulation and electroporation methods as described above, GFP-positive and negative T cells were sorted on a FACSVantage SE flow cytometer (BD Biosciences, San Jose, Calif.) 24 hr post transfection. The cells were placed in AIM-V medium supplemented with 100 U/ml of IL-2 to allow for expansion. Live cells were counted on days 0, 7, 10, 14, and 17, using light microscopy and trypan blue dye exclusion.

Figure 10:
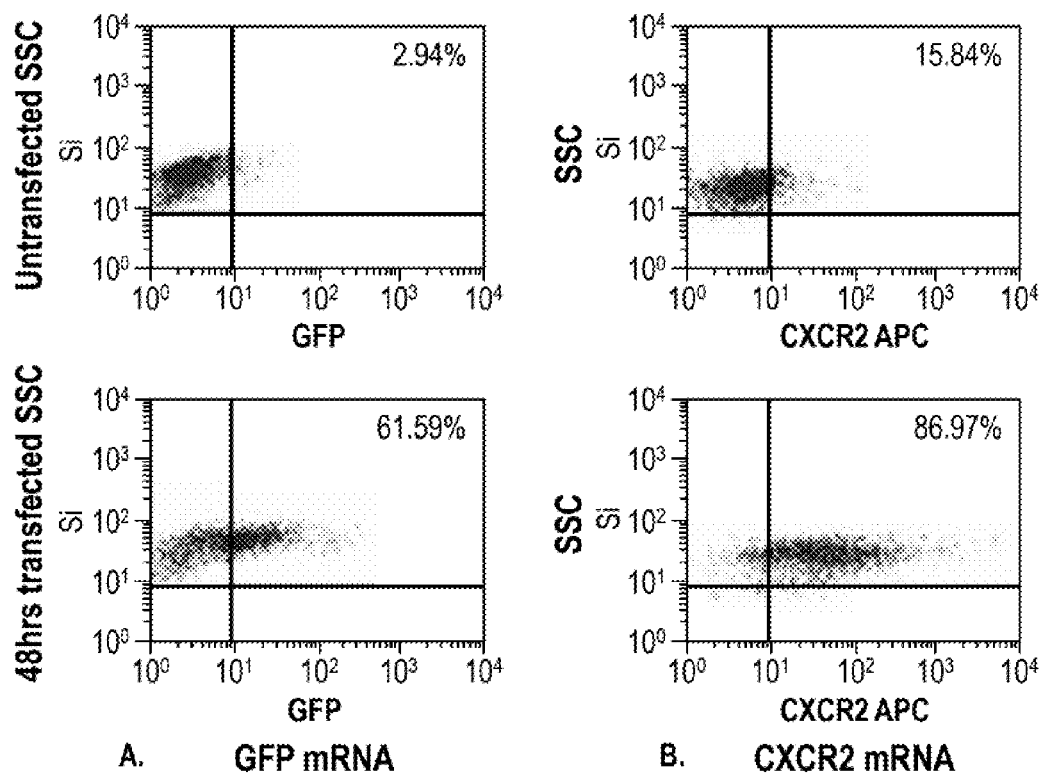
FIG. 10 is a fluorescence-activated cell sorting (FACS) profile. Nonadherent cells from PBMCs were stimulated in vitro, using anti-CD3-coated plates, for 72 hr and harvested, washed, and electroporated with RNA encoding green fluorescent protein (GFP) or CXC chemokine receptor 2 (CXCR2) (2 μg of RNA per 10$^6$ cells) as described in Examples 10 & 11 below. Cells were cultured in medium (AIM-V medium, 2% AB serum, hIL-2 [100 U/ml]) for 48 hr, washed, and analyzed for GFP expression and CXCR2 by administration of allophycocyanin (APC)-conjugated CXCR2-specific monoclonal antibody and flow cytometry. Top: Untransfected T cell expression of GFP (top left) and CXCR2 (top right). Bottom: GFP expression after electroporation with GFP RNA (bottom left) and CXCR2 expression after electroporation with CXCR2 RNA (bottom right). This experiment was repeated twice with similar results.

GFP Expression in Anti-CD3-Activated T Cells:

Stimulation of T cells with immobilized anti-CD3 antibody 48-96 hr before electroporation resulted in high levels of GFP expression in 60-70% of T cells as analyzed by flow cytometry (FIG. 10A).

Figure 11:
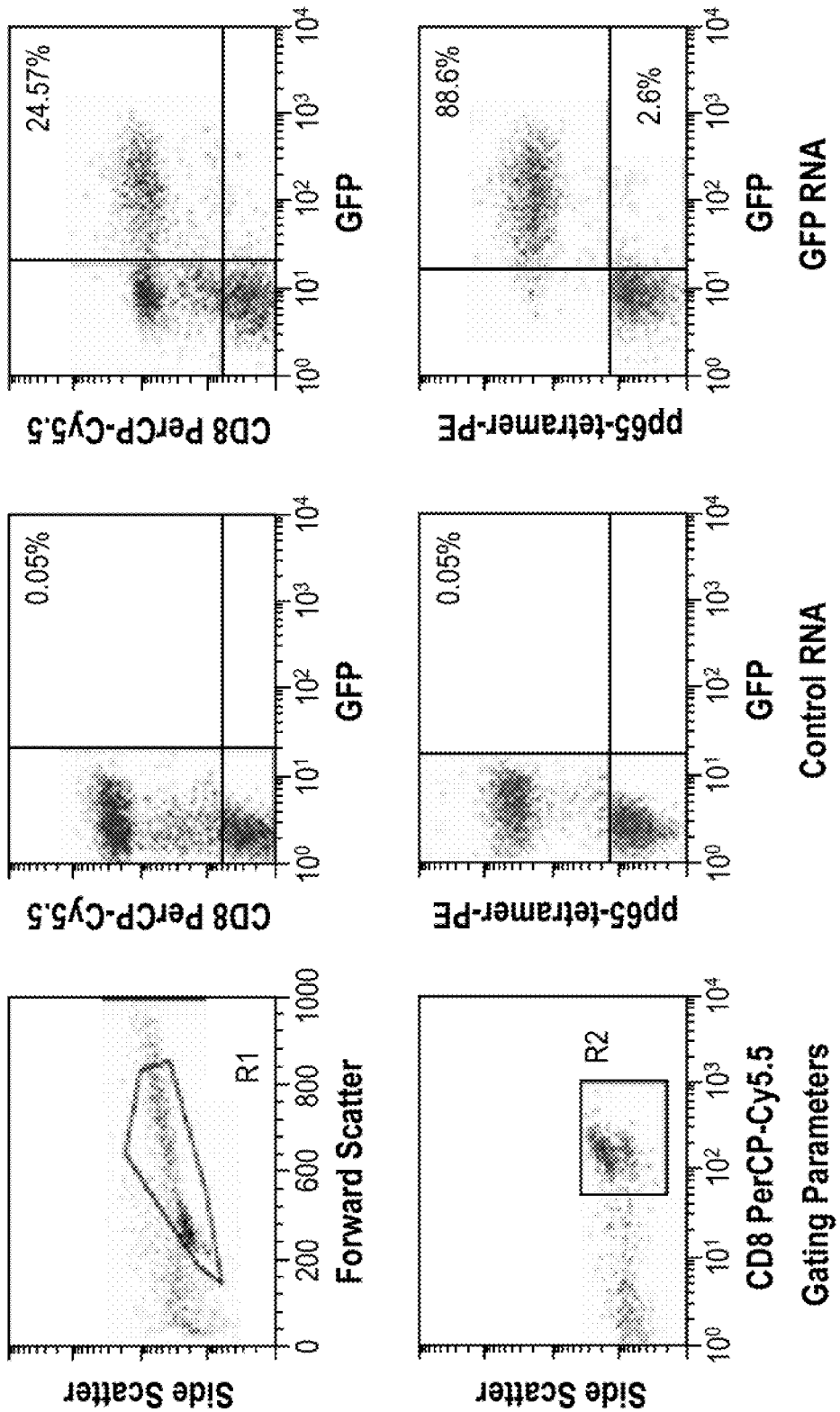
FIG. 11 is a FACS profile. PBMCs from an HLA-A2-positive donor were stimulated for 7 days with autologous DCs pulsed with an HLA-A2-restricted pp65 peptide (N9V), harvested, and electroporated with GFP RNA. Forty-eight hours later GFP expression was examined in N9V-tetramer-positive versus N9V tetramer-negative CD8+ T cells. Left: Gating on blastlike lymphocytes (R1; top) and CD8+ T cells (R2; bottom). Middle: No GFP expression in cells transfected with a control RNA (CXCR2). Right: GFP expression in 24.57% of CD8+ T cells (top right), which consists almost entirely of pp65-specific T cells as shown by tetramer staining (gated on lymphocytes (R1) and CD8+ cells (R2)) (bottom right).

Selection of CMV Antigen-Specific CD8+ T Cells, Using RNA Electroporation of GFP:

The requirement for T cell activation for efficient RNA transfection could allow for the identification of antigen-specific T cells within bulk stimulated PBMC cultures. To determine the efficiency of RNA electroporation in antigen-specific T cells, PBMCs were stimulated for 7 days with autologous DCs pulsed with an HLA-A2-restricted pp65 peptide. Day 7 stimulated cultures were electroporated with GFP RNA and expression of GFP was examined in antigen-specific and nonspecific T cells, using an HLA-A2 pp65 tetramer. Forward and side scatter gating revealed activated lymphocyte cells of blastlike morphology (FIG. 11, top left). GFP expression was shown in approximately 25% of all CD8+ T cells (FIG. 11, top right), and tetramer analysis revealed that expression was restricted almost exclusively to pp65-specific T cells (FIG. 11, bottom right). Of T cells expressing GFP protein, 97% were identified as pp65 specific by tetramer staining. Furthermore, more than 98% of all tetramer-positive CD8+ T cells expressed GFP protein, indicating that RNA transfection not only was restricted to antigen stimulated T cells (demonstrating exquisite specificity; 97.40%), but that this process also efficiently identified all of the relevant responder T cells (demonstrating high sensitivity for identifying antigen-specific T cells; 89.77% sensitivity for identifying all relevant cells). These results were confirmed in three repeat experiments, with a mean specificity for transfection of antigen-specific T cells of 93.10±5.87% and sensitivity of detecting all tetramer-positive T cells by GFP expression of 86.45±8.45%. GFP expression in DC-stimulated T cells cultured in IL-2 (10 U/ml) was found to persist for 5-7 days (FIG. 12A), indicating the capacity to transiently express proteins in rapidly expanding T cells.

Figure 12A:
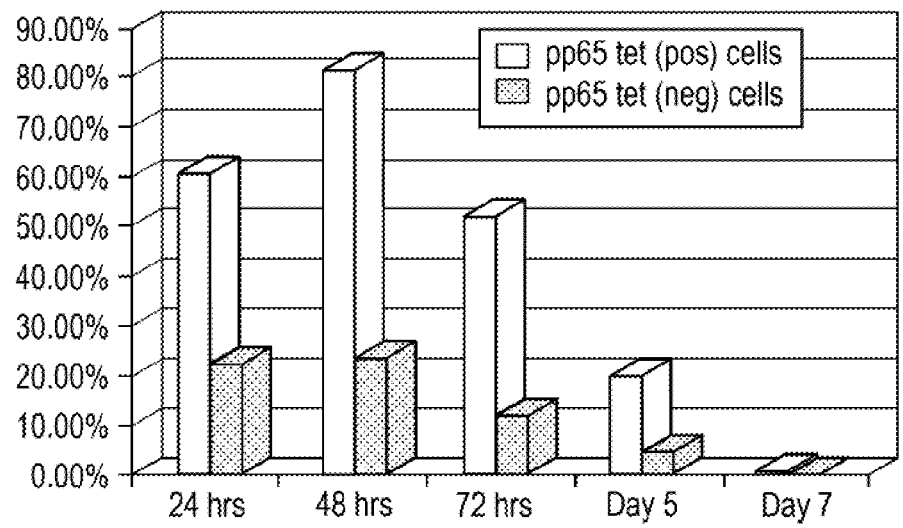
FIG. 12 is a graph showing percentage of GFP-expressing cells and FACS profiles. (A) Kinetics of GFP expression in RNA-transfected T cells stimulated with DCs. PBMCs were stimulated for 11 days in vitro with autologous DCs pulsed with pp65 mRNA as described in Examples 10 & 11 below. Cells were harvested and transfected with GFP RNA (2 μg/106 cells). Expression of GFP in tetramer-positive (HLA-A2B) and tetramer-negative cells was evaluated beginning 24 hr after electroporation and monitored until day 7 postelectroporation. (B) Expansion of sorted GFP RNA-transfected T cells. PBMCs were stimulated for 11 days in vitro with autologous DCs pulsed with pp65 mRNA as described in Materials and Methods. Cells were harvested and transfected with GFP RNA (2 μg/10$^6$ cells). Forty-eight hours later, cells were sorted by flow cytometry on the basis of GFP expression (GFP+ and GFP–) and placed back into culture with high-dose IL-2. Expansion of the cells was evaluated by trypan blue staining and counting of an aliquot of cells every 3-4 days. This experiment was repeated with PBMCs from another donor with similar results. (C) Tetramer analysis of HLA-A2- and HLA-B7-restricted pp65-specific T cells. A panel of tetramers was used to identify patients with more than one type of haplotype-restricted T cell reactivity against pp65 detectable by tetramer. Left: Frequency of HLA-A2- and HLA-B7 pp65-specific T cells in the GFP– fraction. Right: Frequency of tetramer-positive cells in the GFP fraction. (D) Isolation of CMV antigen-specific CD4 T cells by RNA electroporation. PBMCs stimulated with pp65 RNA pulsed DCs were generated as previously described and electroporated with GFP RNA on day 11 after DC stimulation. Cells were sorted into GFP+ and GFP– fractions and 48 hr later were analyzed by intracellular cytokine flow cytometry for IFN-B production after exposure to no antigen, SEB (1 Bg/ml), or CMV pp65 peptide mix (Beckman Coulter). Left: Expression of IFN-B in GFP– CD4+ T cells. Right: IFN-B in GFP+ CD4+ T cells.
Figure 12B:
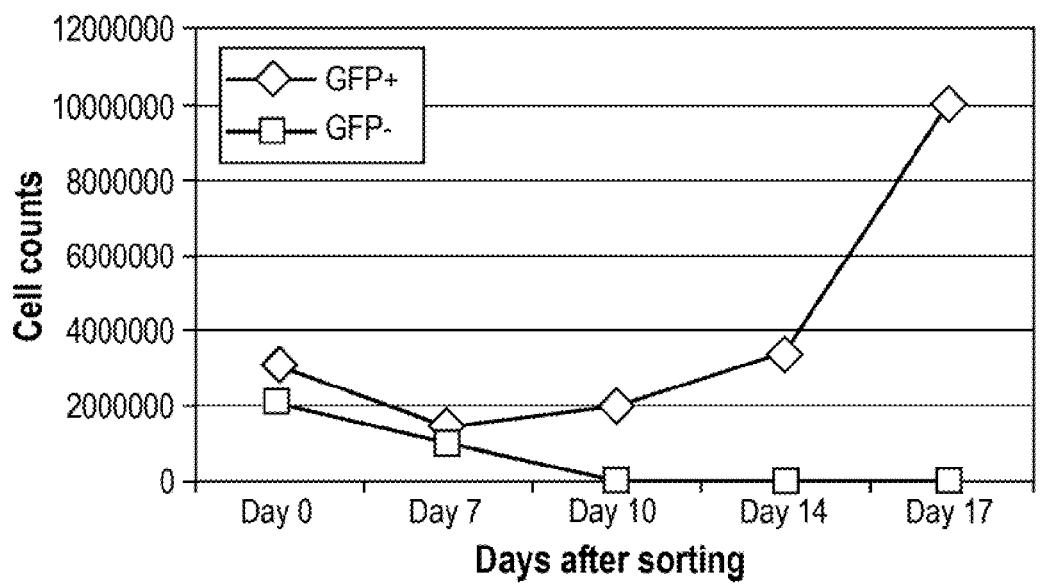

Enrichment and Expansion of CMV Antigen-Specific CD8+ and CD4+ T Cells, Using RNA Electroporation of GFP:

To identify and isolate polyclonal populations of CMV antigen-specific CD4+ and CD8+ T cells, GFP RNA electroporation was conducted on T cells stimulated with DCs transfected with mRNA encoding the full-length pp65 antigen. Eleven days after in vitro stimulation with pp65 RNA pulsed DCs, PBMCs from HLA-A2-positive patients (n=3) were electroporated with GFP RNA and the kinetics of RNA expression were evaluated by flow cytometry (FIG. 12A). Gene expression was found to peak at 48 hr and to decline to baseline by day 7 posttransfection. Therefore, in repeat experiments T cells were electroporated on day 11 after DC stimulation and 48 hr later GFP-positive (GFP+) and GFP-negative (GFP−) T cells were separated by flow cytometric cell sorting. Sorted cells were analyzed by tetramer analysis and cytokine flow cytometry for enrichment of CMV antigen-specific T cells. Equal numbers of GFP+ and GFP− cells were placed back into culture containing IL-2 (100 U/ml) and expansion was evaluated on days 7, 10, 14, and 17 postsorting. Interestingly, only GFP+ T cells were capable of further expansion when cultured with IL-2, indicating that RNA electroporation can efficiently separate T cells capable of further expansion in vitro from anergic or inactivated T cells poststimulation with RNA-pulsed DCs (FIG. 3B). To determine whether GFP expression was simply separating proliferating T cells from anergic cells, GFP+ and GFP− sorted cells were also stimulated with a polyclonal expansion platform consisting of allogeneic feeder cells (PBMCs from an unmatched normal donor), anti-CD3, and high-dose IL-2 (100 U/ml) in a rapid expansion protocol (REP) suitable for generating clinical scale T cell expansions within 14 days (×1000-fold expansion). Using the REP protocol, both GFP− and GFP+ T cells were expanded efficiently, demonstrating that the capacity for RNA transfection does not segregate functional from nonfunctional T cells, but rather identifies T cells that have received sufficient activation during the coculture with antigen pulsed dendritic cells to enter mitotic cell cycling.

Figure 12C:
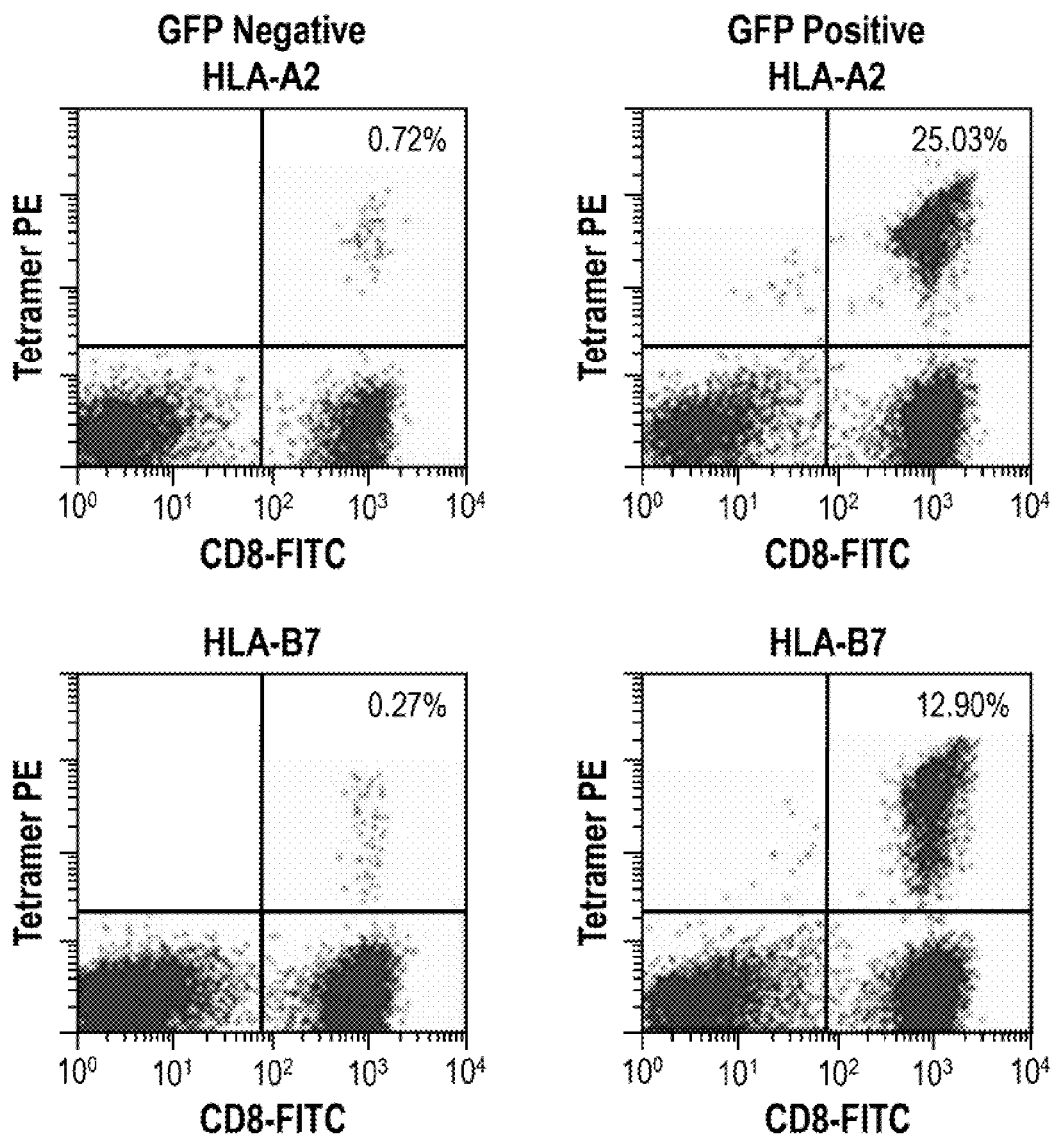
Figure 12D:
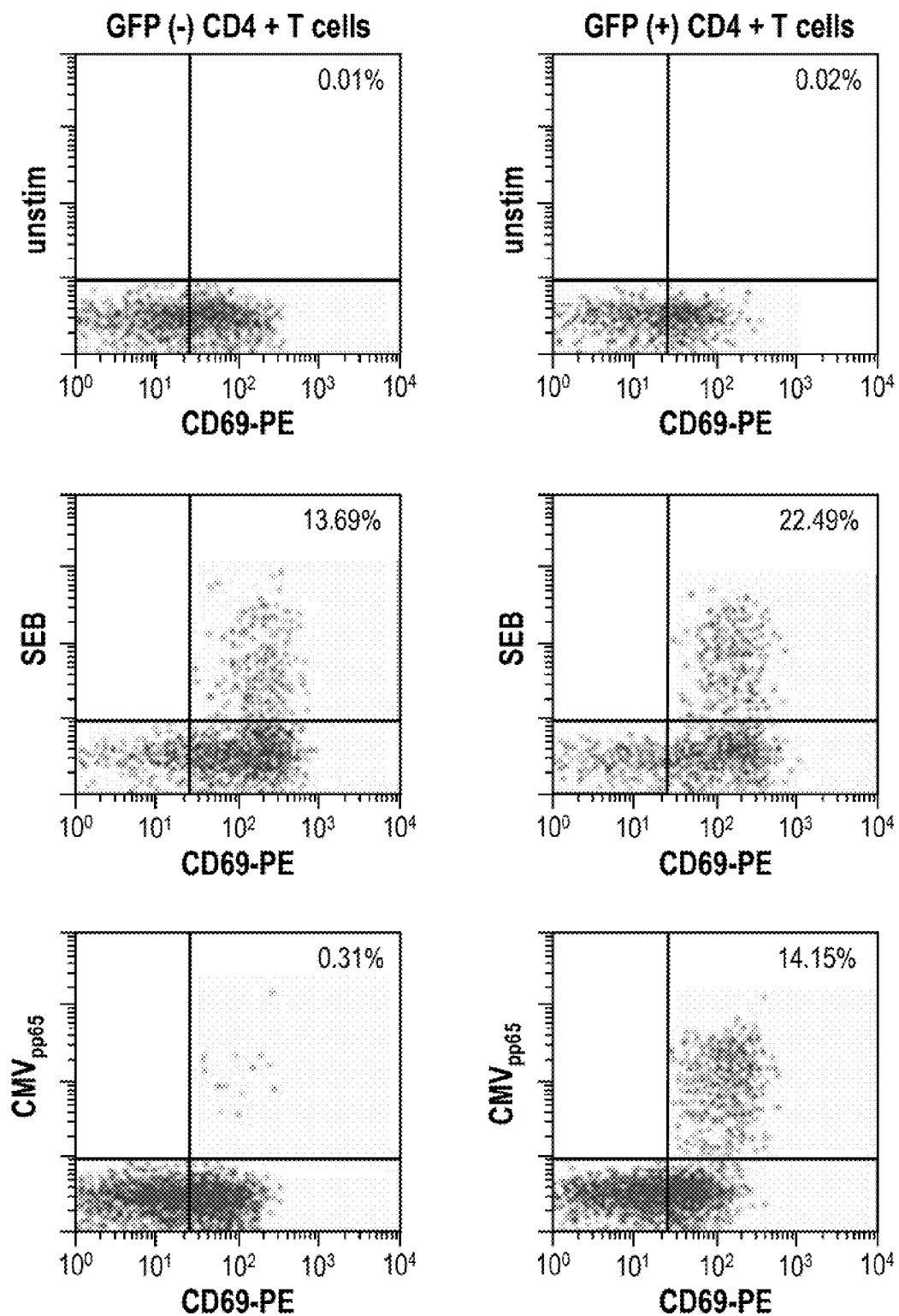

One of the three patient samples examined demonstrated expansion of both HLA-A2- and HLA-B7-restricted pp65-specific CD8+ T cells after stimulation with RNA-pulsed DCs. After RNA electroporation and sorting, the GFP+ fraction contained 95% of the HLA-A2-restricted T cells and 98% of the HLA-B7-restricted T cells, representing a 20- to 50-fold enrichment of antigen-specific T cells within the GFP+ fraction, and demonstrating efficient identification and separation of almost all of the antigen-specific CD8+ T cells (FIG. 12C). Similar results were obtained with two other patients who demonstrated only HLA-A2-restricted pp65 T cell reactivity. To determine the capacity to enrich for CMV antigen-specific CD4+ T cells, cytokine flow cytometry was performed with unstimulated, Staphylococcus enterotoxin B (SEB)-stimulated, or CMV pp65 peptide mix-stimulated T cell fractions. The positive control (SEB-stimulated T cells) indicated that 13.69% of the CD4+ T cells secreted IFN-γ in the GFP-negative fraction and 22.49% of the GFP+ CD4+ T cells secreted IFN-γ, confirming that both fractions contained functional effector CD4+ T cells capable of responding to superantigen. However, IFN-γ secretion in response to the CMV peptide mix by CD4+ T cells was restricted to the GFP+ fraction, with 14.15% of CD4+ T cells secreting cytokine compared with 0.31% of CD4+ T cells in the GFP− fraction (FIG. 12D).

The results showed a 45-fold enrichment of antigen-specific CD4+ T cells within the GFP+ fraction after separation of T cells stimulated with pp65-pulsed DCs and demonstrated an effective method of identifying antigen-specific CD8+ and CD4+ T cells within bulk PBMC cultures for enrichment. Furthermore, the capacity to identify and enrich polyclonal populations of antigen-specific CD8+ and CD4+ T cells provides a method for generating populations of T cells with broad antigen recognition and effector function for use in adoptive immunotherapy.

Example 11

Antigen-Specific T Cells can be Modified to Migrate Toward a Receptor-Specific Chemokine In Vitro and In Vivo Dendritic cell generation, antigen loading with peptide and RNA, maturation of dendritic cells, pulsing of dendritic cells with pp65 peptide or mRNA, source of T lymphocytes, and activation of T cells were performed as described in Example 7 above except that CXCR2 mRNA was used for electroporation of DC-pulsed pp65 peptide-stimulated T cells. CXCR2 mRNA was prepared from the pcDNA3.1+ vector (Missouri S&T cDNA Resource Center, Missouri University of Science and Technology, Rolla, Mo.) and expressed in the Psp73-sph/A64 vector (also kindly provided by E. Gilboa) (Nair et al., Blood, 102:964 (2003)).

For cell migration assays, activated lymphocytes ($5 \times 10^5$ cells) were placed into the upper chamber of six-well filter chamber plates (Beckman Coulter, Fullerton, Calif.) in triplicate. Medium containing no cytokine or various concentrations of IL-8, GRO-α, or UL146 was placed into the lower chamber and cells were incubated for 45 min to 1 hr at 37° C. Medium in the lower chamber was collected, and cells were centrifuged and resuspended in 50 ml of medium and counted by trypan dye exclusion. For assays of in vivo migration into the peritoneal cavity, unmodified or CXCR2 RNA-transfected T lymphocytes were differentially labeled with carboxyfluorescein succinimidyl ester (CFSE; Invitrogen, Carlsbad, Calif.) at 1 μM (untransfected) and 10 μM (CXCR2 RNA transfected) for 5 min in PBS, washed, and injected intravenously into recipient NOD/SCID mice (Taconic, Hudson, N.Y.) at $10^7$ cells per mouse. One microgram of chemokine (IL-8, UL146, or GRO-α) in 1 ml of PBS was injected intraperitoneally every 8 hr for 24 hr after injection of T cells. Mice were sacrificed, lymphocytes were harvested by peritoneal lavage with 3 ml of PBS, and cells were concentrated by centrifugation. Cells were stained with phycoerythrin (PE)-conjugated anti-human CD45 (BD Biosciences) and accumulation of untransfected (CFSE$^{low}$) and CXCR2 RNA transfected (CFSE$^{high}$) cells was evaluated by flow cytometry. The relative accumulation of T cell populations was determined by using accumulation in PBS-treated animals as a baseline for comparison of response to chemokine injection. For in vivo migration assays into the CNS, 1 μg of UL146 in 5 μl of PBS was injected into the right parietal lobe of mice under general anesthesia, using a stereotactic frame, and 5 μl of PBS was injected into the left parietal lobe. CFSE (5 μM)-labeled untransfected or CXCR2 RNA-transfected T cells were injected into recipient mice at $10^7$ cells per mouse. Six hours later, mice were sacrificed and brains were harvested and dissected into right and left parietal lobes. Single-cell digests were prepared by collagenase digestion (1 mg/ml in RPMI) (Sigma-Aldrich, St. Louis, Mo.) of minced tissue for 30 min at 37° C. Single-cell suspensions of left and right parietal lobes were assessed for accumulation of infused lymphocytes by flow cytometric analysis of CFSE-labeled cells; 100,000 events were collected and total numbers of infiltrating T cells were determined by flow cytometric counting of CFSE-positive cells.

Figure 13:
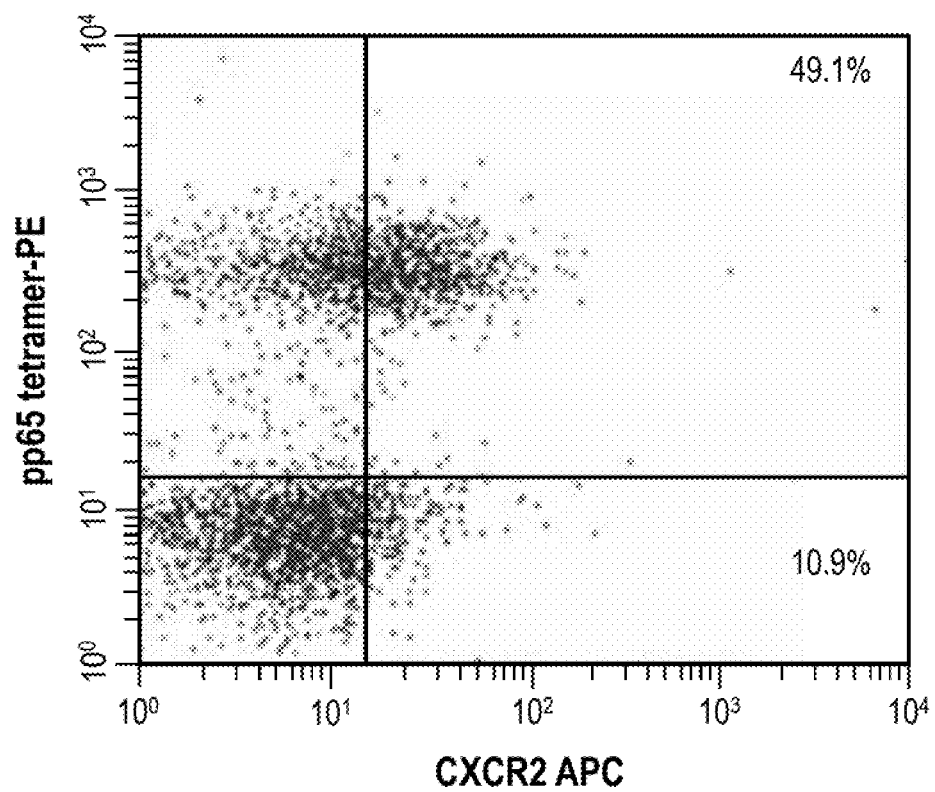
FIG. 13 is a FACS profile. Selective expression of CXCR2 in pp65-specific T cells after RNA electroporation. PBMCs were stimulated for 11 days in vitro with autologous DCs pulsed with pp65 mRNA as described in Examples 10 & 11. Cells were harvested and transfected with CXCR2 RNA (2 μg/10$^6$ cells). Forty-eight hours later, cells were harvested and analyzed for CXCR2 expression in tetramer-positive (HLA-A2-restricted donor) and tetramer-negative CD8+ cells. Baseline expression in activated CD8+ T cells of CXCR2 was approximately 10% (data not shown). Results demonstrated that RNA electroporation resulted in increased CXCR2 expression in CMV-specific T cells only, with expression in 49.1% of tetramer-positive cells, whereas no increase in expression over baseline was observed in tetramer-negative cells after DC stimulation.

Expression of CXCR2 mRNA in Antigen-Specific T Cells:

The capacity to modulate the migratory function of T cells by expression of the chemokine receptor CXCR2, after CXCR2 RNA electroporation into T cells stimulated with pp65-pulsed DCs was examined. CXCR2 expression was monitored in tetramer-positive versus tetramer-negative CD8+ T cells, using CXCR2-specific antibodies and flow cytometry. 10-15% of stimulated CD8+ T cells expressed CXCR2 on their surface (FIG. 10B) at baseline and after CXCR2 RNA transfection approximately 50% of CMV antigen-specific T cells expressed CXCR2 on their surface (FIG. 13). Tetramer-negative T cells, in contrast, did not exhibit CXCR2 expression above background (10.9%), indicating selective expression of the chemokine receptor in antigen-specific T cells after RNA electroporation.

Figure 14A:
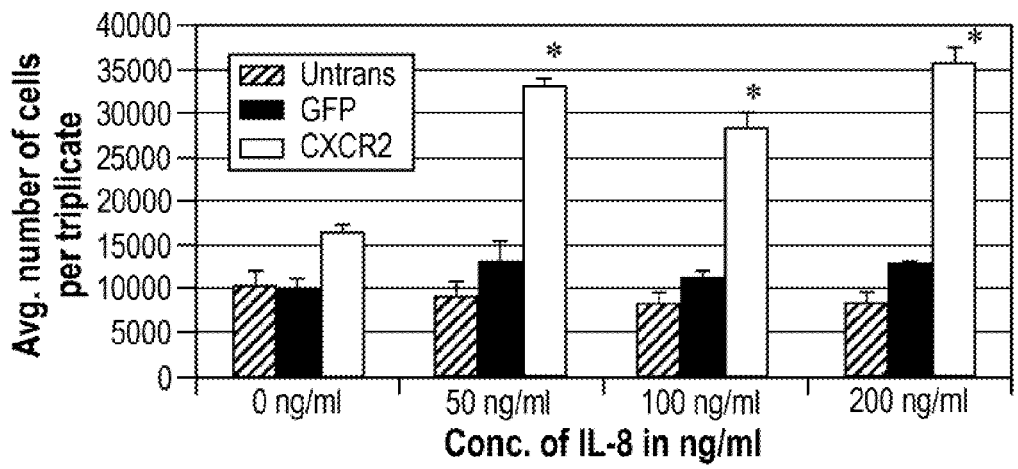
FIG. 14 is a graph. (A) In vitro chemotaxis of CXCR2 and GFP RNA-transfected T cells toward IL-8. PBMCs were activated in vitro using immobilized anti-CD3 antibody-mediated stimulation for 4 days as described in Examples 10 & 11. Cells were harvested and transfected with CXCR2 or GFP RNA (2 μg/10$^6$ cells). Forty eight hours later, cells were harvested, counted, and placed in triplicate into filter chamber culture plates as described in Examples 10 & 11. The migration of untransfected, GFP RNA transfected, and CXCR2 RNA-transfected T cells in response to increasing concentrations of IL-8 was assessed after 45 min of culture in the presence of the indicated concentration of IL-8 in the lower chamber. Results demonstrated enhanced chemotactic response of CXCR2 RNA transfected T cells compared with untransfected and GFP RNA-transfected cells (*$p<0.05$; t test). This experiment has been repeated several times with the same results. (B) In vitro chemotaxis of CXCR2 and GFP RNA-transfected T cells toward GRO-α. Cells were assayed as described above against increasing concentrations of GRO-α in the lower chamber of the filter chamber plates. CXCR2-transfected T cells exhibited significantly increased chemotactic activity in response to GRO-α, whereas GFP RNA-transfected and untransfected T cells showed no significant change in migration in response to GRO-α (*p<0.05; t test). (C) In vitro chemotaxis of CXCR2 and GFP RNA transfected T cells toward UL146. Cells were assayed as described above against increasing concentrations of the CMV-secreted chemokine UL146 in the lower chamber of the filter chamber plates. CXCR2-transfected T cells exhibited markedly increased chemotactic activity in response to UL146, whereas GFP RNA-transfected and untransfected T cells showed no change in migration in response to UL146 (**p<0.01; t test).
Figure 14B:
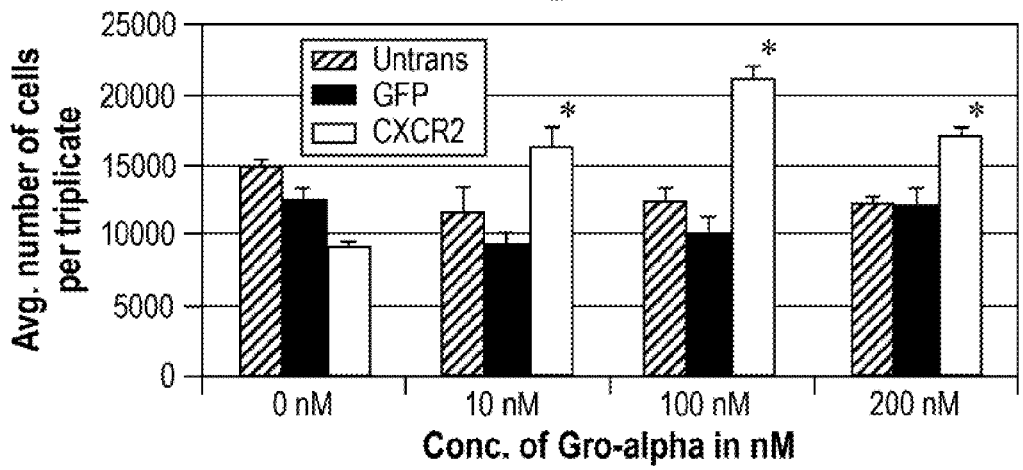
Figure 14C:
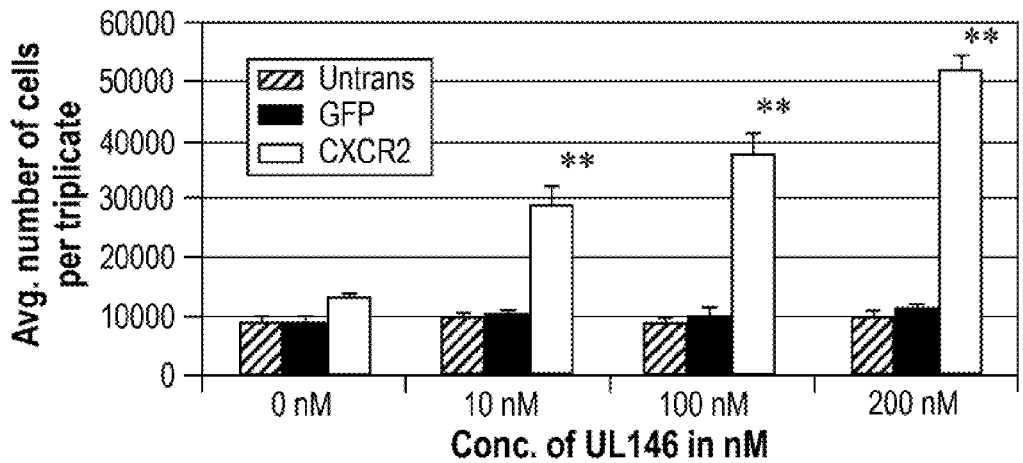

Enhanced Chemotactic Function of CXCR2 RNA-Modified T Cells In Vitro:

The chemotactic function of unmodified, GFP RNA-transfected, and CXCR2 RNA-transfected T cells in Transwell migration assays in response to the CXCR2-specific ligands IL-8, GRO-α, and UL146 was also examined (FIG. 14A-C). CXCR2 RNA-transfected T cells exhibited a dose-responsive enhanced chemotactic response to all three ligands compared with unmodified or GFP RNA-transfected T cells. The chemotactic response toward IL-8, secreted at high levels within a number of tumors, and UL146, a chemokine produced by human cytomegalovirus, and the only ligand exclusive to CXCR2, were increased more than 300-500% in CXCR2-modified T cells.

Figure 15:
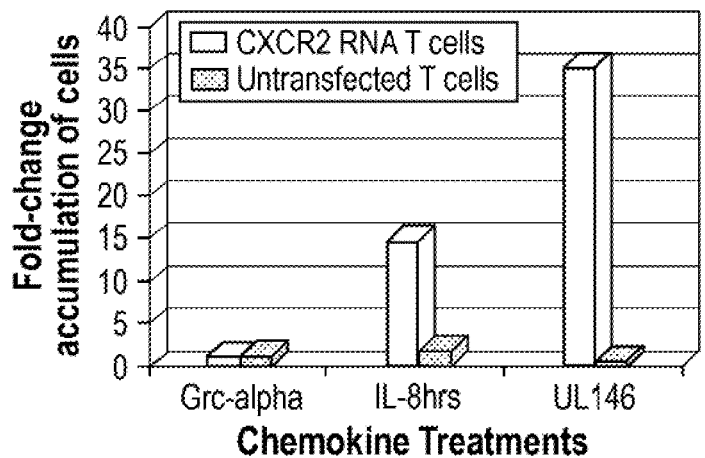
FIG. 15 is a graph and FACS profile. (A) Migration of CXCR2 RNA-transfected T cells into the peritoneal cavity. PBMCs were stimulated for 11 days in vitro with autologous DCs pulsed with pp65 mRNA as described in Examples 10 & 11 below. Cells were harvested and transfected with CXCR2 RNA (2 Bg/106 cells). Forty-eight hours later, untransfected and CXCR2 RNA-transfected cells were harvested and differentially labeled with CFSE (1 µM for untransfected cells and 10 BM for CXCR2 RNA-transfected cells) for 5 min in PBS, washed, mixed, and injected intravenously into SCID mice ($2 \times 10^7$ cells per mouse, n=3 per group). Mice were injected intraperitoneally with PBS only or with chemokines (GRO-α, IL-8, or UL146) at 1 µg/ml in PBS every 8 hr for 24 hr after injection of T cells. Lymphocytes were harvested after sacrifice by peritoneal lavage and centrifuged, and the relative accumulation of untransfected and CXCR2 RNA-transfected cells was evaluated by flow cytometric analysis. Accumulation of $CFSE^{high}$ cells (CXC2 RNA transfected T cells) and $CFSE^{low}$ cells (untransfected T cells) in PBS-treated animals was used as a baseline for comparison with the accumulation of cells in cytokine-treated animals. Data are displayed as fold change compared with PBS-treated animals. (B) Migration of CXCR2 RNA-transfected T cells into the CNS. PBMCs were stimulated for 11 days in vitro with autologous DCs pulsed with pp65 mRNA as described in Examples 10 & 11. Cells were harvested and transfected with CXCR2 RNA (2 µg/$10^6$ cells). Forty-eight hours later, untransfected and CXCR2 RNA-transfected cells were harvested and labeled with CFSE (5 µM) for 5 min in PBS, washed, and injected intravenously into SCID mice ($1 \times 10^7$ cells per mouse, n=3 per group). Anesthetized mice were subsequently injected via the right parietal lobe with the CMV chemokine UL146 (1 µg in 5 µl of PBS) and via the left parietal lobe with PBS only. The accumulation of CFSE-labeled cells in the right and left parietal lobes was assessed 6 hr later by flow cytometry after dissection of the cerebral hemispheres and single-cell digest preparation from the parietal lobes. A representative flow cytometric dot plot of a mouse injected with CXCR2 RNA-transfected T cells shows greater accumulation of lymphocytes within the right parietal lobe injected with the CXCR2 ligand UL146. (C) In vivo migration of CXCR2-transfected T cells. The accumulation of T cells within the right (UL146-injected) and left (PBS-injected) parietal lobes was assessed by flow cytometry and human T cells per 100,000 events were plotted. Results demonstrated significant accumulation of CXCR2 RNA-transfected T cells within the CNS in response to UL146, whereas untransfected T cells did not exhibit any preferential accumulation (*p<0.05; t test).
Figure 15:
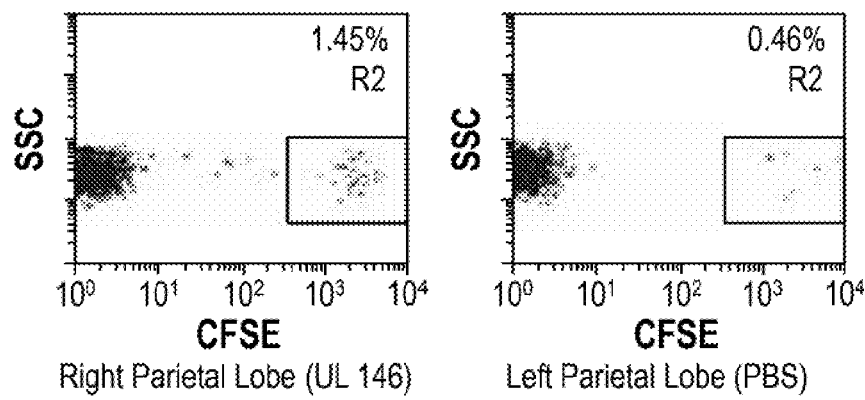
Figure 15:
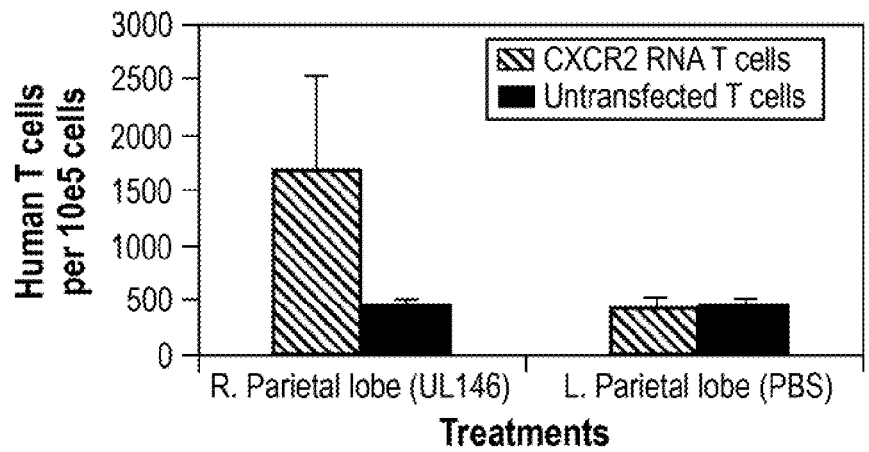

Enhanced Migration of CXCR2 RNA-Modified T Cells In Vivo:

To determine whether transfection of CXCR2 RNA into activated T cells could facilitate T cell migration in vivo, the migration of RNA-modified T cells into the peritoneal cavity and CNS of SCID mice that had been injected with CXCR2-specific chemokines was evaluated. Mice were injected intraperitoneally with chemokines (1 μg/ml) every 8 hr for 24 hr post infusion of differentially CFSE-labeled untransfected or CXCR2 RNA-transfected T cells. Mice were sacrificed and cells were harvested by peritoneal lavage, and the accumulation of CXCR2-transfected and untransfected T cells was analyzed by flow cytometry by gating on human CD45+ cells and evaluating the relative accumulation of CFSE$^{low}$ cells (untransfected) to CFSE$^{high}$ cells (CXCR2 RNA transfected). The relative accumulation of T cells in chemokine-injected mice was compared with that of PBS-injected mice and is shown in FIG. 15A. Results showed the accumulation of CXCR2 RNA transfected cells in response to UL146 and IL-8. The greatest chemotactic response was to UL146, which paralleled findings of in vitro studies. No significant accumulation was observed in response to GRO-α in this in vivo assay.

Whether CXCR2 RNA modification could lead to accumulation of T cells within the CNS in response to UL146 also was examined. Immunodeficient mice were administered a single injection of PBS in the left frontal parietal lobe, or of UL146 (1 μg) in the right frontal parietal lobe, under guidance of a stereotactic frame. CFSE-labeled untransfected or CXCR2 RNA-transfected T cells were injected intravenously and 6 hr post injection, left and right cerebral hemispheres were harvested, single cell digests were prepared, and detection of CFSE-labeled T cells was evaluated by flow cytometry. As shown in FIG. 15B, CXCR2 RNA-modified T cells exhibited enhanced infiltration of the UL146-injected hemispheres compared with PBS-injected hemispheres, whereas untransfected T cells exhibited no significant difference in infiltration of either hemisphere. Preferential accumulation of CXCR2 RNA-modified T cells at later time points was not observed, likely secondary to the transient gradient of chemokine established by the intracranial injection.

These results showed that CXCR2 RNA-modified T cells exhibit enhanced chemotactic function in vitro and in vivo and that RNA-based modification of T cells can be used to selectively identify and modify antigen-specific T cells.

Thus, a gene transfer technology employing the electroporation of messenger RNA encoding genes that could be used to identify and separate transfected from untransfected T cell populations, as well as modify their migratory function, was utilized. Using GFP as an example of a marker gene, CMV antigen-specific T cells were readily identified and separated from cultures stimulated with pp65-pulsed DCs, and that RNA transfection can be used to simultaneously isolate both antigen-specific CD4+ and CD8+ T cells. Nucleic acid-mediated transfection of antigen-specific T cells has particular advantages in being able to simultaneously enrich the purity and modify the function of antigen-specific T cells by a single strategy, such as the electroporation of chemokine receptor or other surface receptors of interest and isolation of cells on the basis of the expression of the transfected receptor. The expression of genes encoding proteins that can modulate the function of T cells, such as CXCR2, can be targeted preferentially to those T cells with a specificity of interest, using an antigen specific stimulation platform followed by RNA electroporation, for example. Genes that enhance the migration of T cells to sites of inflammation, viral infection, or tumor progression, such as chemokine receptors, represent a class of proteins whose expression might significantly enhance the efficacy of adoptively transferred lymphocytes. CXCR2 is normally expressed only in a small fraction of T lymphocytes and mediates chemotaxis toward IL-8, GRO-α, and UL146, the latter a CMV antigen-specific chemokine. IL-8 has been shown to be increased in sites of inflammation as well as dramatically elevated within gliomas and other tumors. GRO-α is increased in expression in a number of malignancies including melanoma, gastrointestinal cancers, and malignant gliomas. Its expression in gliomas correlates with tumor grade, rendering T cells with chemotactic function toward GRO-α, a useful effector in tracking down invasive high-grade lesions. UL146 is a chemokine synthesized by CMV with specificity for CXCR2. The localization of CMV antigen-specific T cells expressing CXCR2 to sites of viral infection through UL146-mediated chemoattraction can enhance the efficacy of immunotherapy.

Additionally, these studies at least demonstrate that T cells can be localized, for example to sites of therapeutic interest, using RNAs encoding chemokine receptors or other chemotactic receptors. This is of particular use in the targeting of brain tumors, as the CNS displays limited normal trafficking of circulating immune cells. Among other things, this approach also can direct antigen-specific effector T cells to sites of tumor growth, viral infection, or vaccine sites for preferential expansion.

Example 12

Qualitative CMV Detection

To develop a qualitative CMV detection method, 29 different PCR primers (Table 1) spanning 10 different CMV genes were evaluated for detecting CMV DNA in an expanded cohort of blood samples from patients with newly-diagnosed GBM (223 serial blood samples from 45 patients with newly-diagnosed GBM).

Peripheral blood from normal volunteers (median age 42 for healthy volunteers (n=11) and age 46 for surgical control patients (n=6)), patients with newly-diagnosed GBM (median age 52.5 (n=45)), and patients undergoing allogeneic bone marrow transplantation (median age (n=5)) was collected in accordance with the Duke University Institutional Review Board. Whole blood was aliquoted into cryotubes and snap frozen in liquid nitrogen and stored at −130° C. until DNA extraction. Plasma and serum was collected by centrifugation of heparinized or non-heparinized blood respectfully at 2000 g for 20 min and snap frozen in cryotubes in liquid nitrogen and stored at −130° C. until DNA extraction. Tumors were collected during surgery after informed consent from patients with newly-diagnosed GBM, minced and snap frozen in liquid nitrogen. Specimens were stored at minus 130° C. until DNA extraction. DNA was extracted from 10 mg of minced tissue using TissueDirect™ Multiplex PCR System (GenScript Corporation, Piscataway, N.J.).

DNA was extracted from GBM tumor specimens and human blood or plasma or serum with TissueDirect™ Multiplex PCR System (GenScript Corporation, Piscataway, N.J.). For positive control samples, whole blood, serum, or plasma from seronegative volunteers was spiked with known concentrations of CMV Quantitated Viral DNA AD169 Strain (Advanced Biotechnologies (Cat#08-925-000), Columbia, Md.). Lysis solution from the TissueDirect™ Multiplex kit was made by mixing solution TD-A with solution TD-B at 1:9 ratio. For DNA extraction, various ratios of Lysis solution to sample volume were evaluated and 50 µL of Lysis solution TD-A/B was added to 10 µL of blood (serum or plasma or tumor tissue) per sample, mixed well by pipetting up and down or tapping/rotating the tube, and spun briefly. The samples were incubated at 95° C. for 15-30 minutes being sure to keep caps tight to prevent loss due to evaporation until sample was uniformly lysed by Lysis solution. 50 µL of solution TD-C was added to each sample, mixed well and spun at high speed on microcentrifuge for one minute and supernatants collected. 11 µL of 5M NaAC or 3M $NH_4AC$ (1:10 volume of lysed sample volume) and 220 µL of 100% Alcohol (EtOH, 2 volumes of sample volume) were added to the supernatant for precipitating DNA. The DNA pellets then centrifuged at full speed (14,000 rpm) in a microcentrifuge for at least 10 minutes and washed twice with 70% EtOH and reconstituted with 10 µL of Nuclease-Free water or TE buffer. All DNA extractions were performed in a separate laboratory from the molecular biology lab in which PCR reactions were carried out. 2-5 µL of each sample (equivalent to the DNA extracted from 2-5 µL of whole blood, plasma, or serum) was added to PCR reactions for CMV detection.

Qualitative PCR detection was run using TissueDirect™ Multiplex PCR System (GenScript Corporation, Piscataway, N.J.) according to manufacturer's instructions and visualization by gel electrophoresis. Twenty-nine different primers spanning 10 CMV genes were selected from published literature or designed on Vector NTI Advance 9 software (Invitrogen, Carlsbad, Calif.) and synthesized by Integrated DNA Technologies (IDT, Coralville, Iowa). DNA extracted from 2-5 µL of sample (whole blood, serum, or plasma) or tumor tissue was carefully added to each 50 µL of PCR reaction. A sample from a CMV seronegative donor and DNase-Free water was used in parallel as a PCR negative control. PCR was run on iCycler (Bio-Rad, Hercules, Calif.) at 94° C. for 15 min., 40 cycles of 94° C. for 40 sec., annealing temperature for 1 min. and 72° C. for 1 min, and ended with extension at 72° C. for 10 min. PCR products were visualized by electropheresis on Criterion Precast 10% of polyacrymide gel (Bio-Rad (Cat#345-0053), Hercules, Calif.) in 1×TBE (Bio-Rad, Hercules, Calif.) and stained with SYBR Gold Nucleic Acid Gel Stain (Invitrogen (Cat#S11494), Carlsbad, Calif.). For confirmation of CMV DNA detection, some amplified DNA bands were isolated from gels with QIAEXII (Qiagen, Valencia, Calif.) following manufacturer's protocol and sequenced at Duke University Comprehensive Cancer Center DNA Sequencing Facility. Sequence identity was analyzed using BLAST of NCBI database and alignment analysis of specimens conducted using Vector NTI Advance 10 (Invitrogen, Carlsbad, Calif.).

As shown in Table 1, the detection rate of CMV viremia in peripheral blood samples of patients with GBM ranged from 12% to 73.5% depending on the primers utilized in the PCR assay. Primers within the gB gene (e.g., B-i1i2) were found to be the most sensitive for detection of CMV in the peripheral blood of patients with GBM. No viral DNA was detected in control lanes (water only) and the peripheral blood of normal volunteers were negative for detection of viral DNA upon several repeat assays (0 out of 17 samples including 11 CMV seropositive volunteers; $p=8.4\times10^{-10}$; Fisher's exact test). The detection rate of CMV in the expanded cohort of 223 blood samples (164 positive out of 223 samples) did not differ significantly from initial findings of 16 of 20 positive blood samples (p=0.603; Fisher's exact test) (data not shown).

In order to evaluate the effect of amplicon size on CMV detection rate, the overall detection rate of CMV in the blood of patients with GBM for all primers was compared based on amplicon size alone by Spearman and Pearson correlation coefficient analysis. Primers designed to give amplicons of 200 bp or less were also found to have a lower threshold of detection of CMV and more reliable amplification (Table 1). For example, primers gB E1E2 (amplicon size 268), gBi1i2 (amplicon size 144), and gBi3i4 (amplicon size 122) all span the same region of DNA within the gB gene and differ only by the distance between the primer sets. The observation that smaller amplicons gave a higher rate of detection was made with primers in other CMV genes as well. An inverse correlation between amplicon size and detection rate was shown for the 29 primers investigated independently of the gene evaluated. The Pearson Correlation Coefficient (r=−0.37622) and Spearman Correlation Coefficients (r=−0.41523 were both significant (p=0.0443 and 0.0251 respectively). These results indicate the profound effects of primer selection and amplicon size in the detection rate of CMV DNA in peripheral blood of patients with GBM.

To investigate the impact of PCR amplification directly from samples without DNA purification, BloodReady™ Kit (GenScript Corporation, Piscataway, N.J.) was compared to TissueDirect™ Kit (GenScript Corporation, Piscataway, N.J.) for the direct amplification of DNA from whole blood and tumor tissue. PCR amplification can be performed directly from cell lysates after DNA extraction or after purification of DNA from other organic molecules present within in cellular lysates.

Human tissues was kept on ice immediately after surgery and minced into 10 mg size within less than half hour, then snap frozen in liquid nitrogen and stored at −137° C. until to use. Patient or normal blood was aliquoted 10 µl per tube and snap frozen in liquid nitrogen and stored at −137° C. until to use.

Genomic DNA Preparation: Used TissueDirect™ DNA Preparation and Multiplex PCR Kit (Cat#L00195; GenScript, Piscataway, N.J.): 1. Thawed Buffers TD-A, TD-B and TD-C at room temperature and placed on ice after thawing; 2. Mixed 5 µl of TD-A and 45 µl of TD-B (1:9 ratio) for each sample and spun to yield 50 µA of lyses solution (TD-AIB) per sample; 3. Added 50 µl of lysis solution TD-AB to each sample 10 mg of tissue or 10 µl of blood (serum or plasma) and mixed well by pipetting up and down or tapping/rotating the tube; 4. Incubated the samples at 65° C. for at least 10 minutes until complete lyses of sample occurred; 5. Removed tubes from incubation, added 50 µl of TD-C to each tube, and mixed well; 6. Spun samples at ~14,000 rpm for at least 1 minute; 7. Stored the supernatant (genomic DNA extract) at 4° C. or proceeded with PCR amplification; 8. Used 1.5 µl of the genomic DNA extract in the 20 µl of PCR per sample.

PCR Amplification:

A. Qualitative measurement: PCR amplification was performed with TissueDirect™ DNA Preparation and Multiplex PCR Kit (Cat#L00195; GenScript, Piscataway, N.J.) or Hot-Master™ Taq PCR system (Brinkmann, Westbury, N.Y.):

Pre-Mix Solution is shown in Table 4.

TABLE 4

| PreMix | |
|---|---|
| GenScript Multiplex PCR System | 1X |
| PCR H$_2$O | 8.2 µl |
| Sense Primer (lug/ul) | 0.15 µl |
| Antisense Primer (1 ug/ul) | 0.15 µl |
| GenScript 2X PCR premix | 10 µl |
| Pre-Mix Volume | 18.5 µl |
| Genomic DNA to be added | 1.5 µl |
| Total Volume | 20 µl |
| Annealing Temp. | 60° C. |

Added 1.5 µl of genomic DNA solution to 18.5 µl of pre-mix shown in Table 4 to give 20 µl of PCR solution per tube. Placed PCR tubes into Bio-Rad iCycler (Bio-Rad, Milpitas, Calif.) and cycled as follows: 1 cycle of 94° C. for 5 minutes (Denaturation); and 40 cycles of: 94° C. for 40 seconds (Denaturation)/60° C. for 40 seconds (Annealing)/72° C. for 40 seconds (Extension)/1 cycle of 72° C. for 10 minutes (Extension).

B. Quantitative Measurement: Real-Time PCR amplification with iQ SYBR Green SuperMix (2× Mix for Real-Time, Bio-Rad Cat. #170-8880) or iQ SuperMix (2× SuperMix for Real-Time, Bio-Rad Cat. #170-8860):

Pre-Mix Solution is shown in Table 5.

TABLE 5

| PreMix | |
|---|---|
| GenScript PCR | 1X |
| PCR H$_2$O | 16.7 µl |
| iQ SYBR Green SuperMix or | 20 µl |
| iQ SuperMix with Gene Specific Probe | |
| Sense Primer (lug/u1) | 0.15 µl |
| Antisense Primer (lug/u1) | 0.15 µl |
| Pre-Mix Volume | 37 µl |
| Genoinic DNA to be added | 5 µl |
| Total Volume | 40 µl |
| Annealing Temp. | 60° C. |
| PCR product bp | |

Added 3 µl of genomic DNA to 37 µl of pre-mix shown in Table 5 to yield 40 µl of PCR solution. Placed the PCR solution into Byroad iCycler and cycled as follows: 1 cycle of 95° C. for 3 minutes (Denaturation); and 40 cycles of: 94° C. for 30 seconds (Denaturation)/60° C. for 30 seconds (Annealing)/72° C. for 30 seconds (Extension)/1 cycle of 72° C. for 10 minutes (Extension).

Following amplification, Real-Time PCR products were analyzed with standard curve and the data normalized with housekeeping genes.

PCR Product Detection: Criterion™ Precast 10% Gel (26 Well, 15 µl/well) in TBE (Cat. #345-0053; BioRad, Hercules, Calif.) was used essentially as follows: Added 1×TBE buffer to electrophoresis chamber up to the fill line. Mixed 2.5 µl of DNA Loading Buffer with 10 µl of PCR product per sample to yield 12.5 µl aliquots. Added 1.5 µl of EZ DNA Molecular Weight Standard (100 bp MW, BioRad Cat#170-8352, 0.05 µg/µl, 500 µl) into first well of gel. Added 12.5 µl aliquots of PCR products to wells 2-26. The gel was run at 120 voltages for 2 hrs at room temperature (RT). Electrophoresis was terminated and transfer each gel into 25 ml of Staining buffer (SYBR Gold Nucleic Acid Gel Stain, Invitrogen/Molecular Probe Cat#511494) in 1×TBE. Gels were stained for 15 minutes at RT. Photographed gel picture using different exposure times to record and analyze the PCR products. Each right size of PCR product was then cut out from the gel and the DNA was extracted using QIAEX II (Qiagen, Valencia, Calif.). The extracted DNA was then sequenced.

Figure 16A:
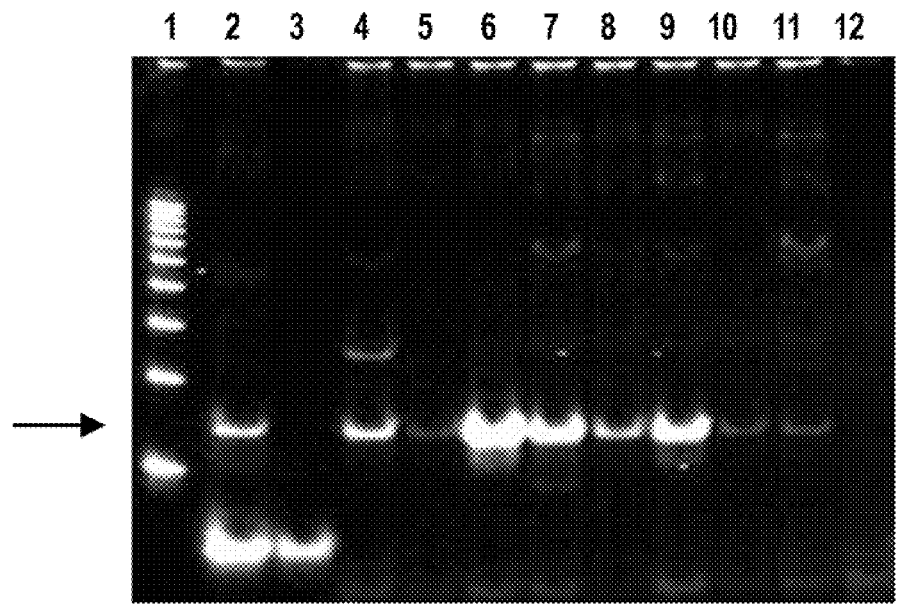
FIG. 16 is an electrophoretic gel showing amplification of CMV gB (UL55) DNA from peripheral blood and tumors of patients with GBM. A: Lane 1: 100 bp DNA ladder; Lanes 2-12: Peripheral blood samples from 11 patients with newly-diagnosed GBM taken at time of primary resection of tumor shows strong detection of viral DNA in 6 out of 11 patients and a weak band of appropriate size in 3 out of 11 patients. B: Lane 1: 100 bp DNA ladder; Lanes 2-F: GBM tumor samples from 14 patients with high grade astrocytomas (11 GBM, 3 AA) shows clear band of appropriate size in 11 out of 14 patients. Lane 4 has 100 bp DNA ladder mixed with sample for alignment with amplified bands.
Figure 16B:
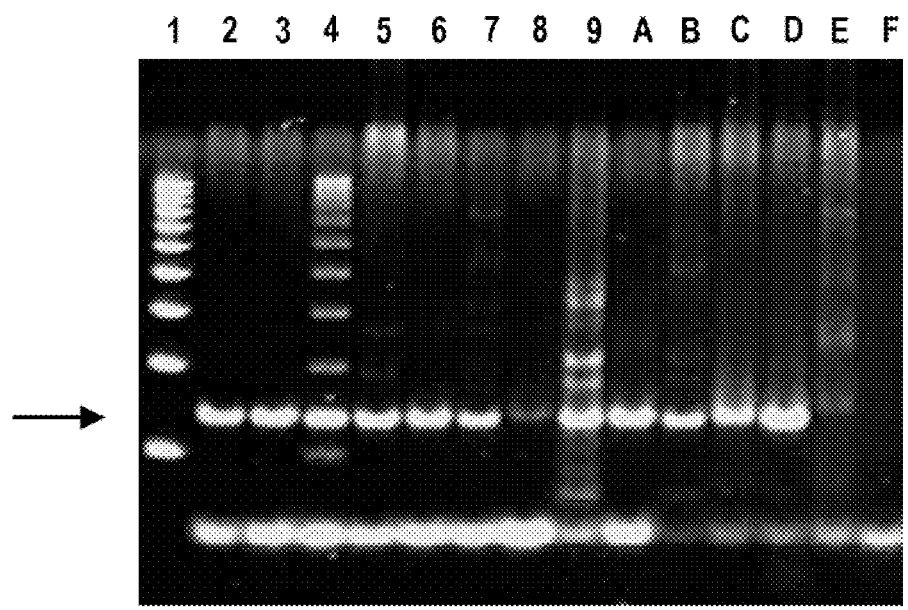
Figure 17:
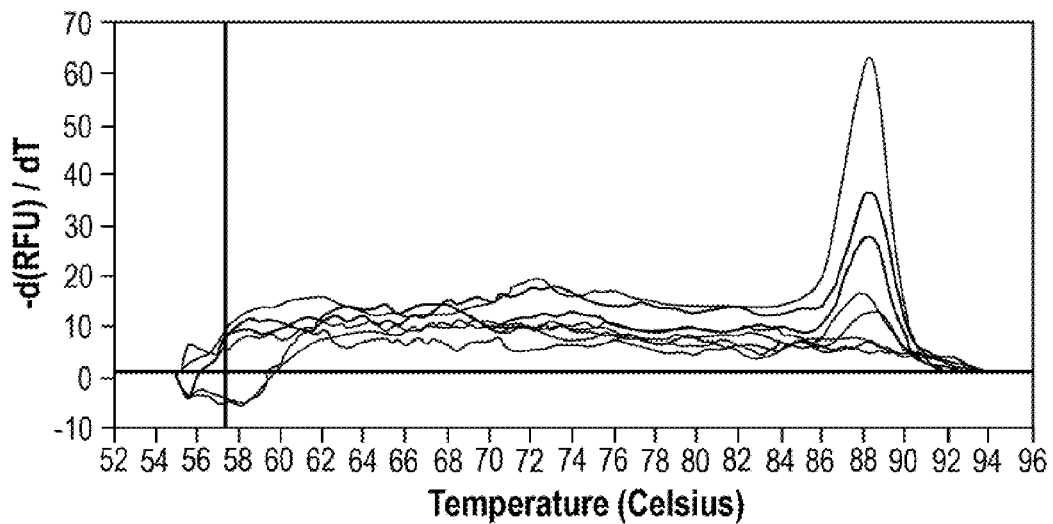
FIG. 17 is a melting curve graph of HCMV gp64 Real-Time PCR from GBM patient sera.
Figure 18:
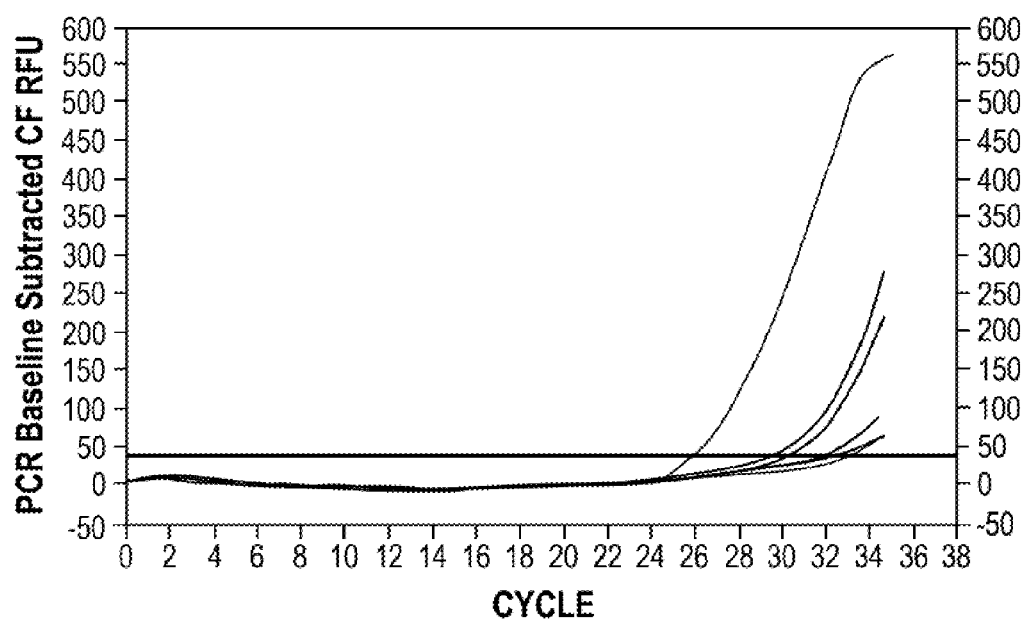
FIG. 18 is a PCR amplification cycle graph of HCMV gp64 Real-Time PCR from GBM patient sera.

As shown in FIG. 16, TissueDirect™ Kit was reliable for providing clean and distinct amplifiable bands from both whole blood and tumor samples. Also PCR results using the TissueDirect™ Kit on small sample volumes (10-20 µL) were compared to two commercial DNA Purification Kits: DNeasy® (Qiagen, Valencia, Calif.) and Gentra® PureGene® (Qiagen, Valencia, Calif.) which require larger sample volume (0.2 ml to 1.0 ml of whole blood, serum, or plasma) for DNA extraction. No difference in the lower limits of viral DNA detection was found when using the TissueDirect™ Kit compared to purifying DNA from larger sample volumes (not shown), indicating that the simpler and faster direct DNA extraction method is equally effective and may be preferable, particularly when sample volume is limiting. The melt curve graph of HCMV gp64 Real-Time PCR from GBM patient sera is shown in FIG. 17 and the PCR amplification cycle graph of HCMV gp64 Real-Time PCR from GBM patient sera is shown in FIG. 18.

Moreover, the ratio of sample to tissue Lysis buffer was compared using a sample:buffer ratio of 1:5, 1:10, and 1:20 and evaluated by PCR detection of CMV DNA using the gB primer set (B-i1i2; Table 1) on 34 known positive samples. As shown in Table 6, a sample to buffer ratio of one to five gave detection with a strong, clear band of appropriate size (122 bp), while other ratios either gave reduced intensity of band signal or resulted in detection of non-specific bands.

TABLE 6

Comparison of extraction buffers and buffer:sample ratio in detection of CMV DNA.

| Buffer Ratio (Sample/ Buffer) | TissueDirect | | TD-A/B | | | | BloodReady | BR-A | |
|---|---|---|---|---|---|---|---|---|---|
| | 2:1 | 1:1 | 1:2 | 1:5 | 1:10 | 1:20 | 1:5 | 1:10 | 1:20 |
| Blood | 12/34 | 17/34 | 34/34 | 34/34 | 34/34 | 34/34 | 7/34 | 16/34 | 34/34 |
| Plasma | 17/34 | 21/34 | 34/34 | 34/34 | 34/34 | 34/34 | 12/34 | 20/34 | 34/34 |
| Serum | 20/34 | 24/34 | 34/34 | 34/34 | 34/34 | 34/34 | 14/34 | 23/34 | 34/34 |

In all cases, the predominant band corresponded to the gB gene product. Moreover, SYBR Gold Nucleic Acid Gel Stain (Invitrogen, Carlsbad, Calif.) gave an enhanced visualization of viral DNA bands compared to ethidium bromide staining (not shown). A ratio of 1:5 was chosen for all subsequent analysis.

There was no loss of viral DNA during genomic DNA extraction from samples within the single step protocol described herein, and specifically this is very important to detect low level of viral DNA in the samples thereby saving precious patient samples. The GenScript TissueDirect™ Multiplex PCR System was employed for all blood, serum and tissues to make sure that the viral DNA is completely released into the lyses buffer (TD-A/B). Thus, we were able to obtain no viral DNA loss and limit inhibitors to PCR. Moreover, PCR primers were designed to make smaller amplicons (less than 200 bp) with high gene specificity and no cross-binding to human genome for more efficient and sensitive PCR amplification within the high human genome content and no purification to remove inhibitors to PCR. The PCR condition amplified gene specific products at very low level of target DNA. The detection sensitivity was increased at least 10 fold compared to conventional agarose gel stained with Ethidium Bromide after polyacrylamide gel electrophoresis. SYBR Gold staining and digital photograph were all optimized together, thereby avoiding transferring separated PCR products from agarose gels to membrane for gene specific probe hybridization to detect viral DNA or NEST PCR.

Example 13

Quantitative CMV Detection

To provide a quantitative PCR assay for measuring CMV DNA levels specifically in patient samples, 15 gene-specific primer and probe combinations (Table 2) were evaluated for quantifying CMV DNA copy number in whole blood spiked with CMV whole genomic DNA as a positive control standard using real-time PCR.

Real-Time PCR detection was run in TaqMan® Universal PCR Master Mix (Applied Biosystems, Foster City, Calif.) by following manufacturer's instruction. Fifteen different gene-specific primer & probe sets spanning 5 CMV genes were chosen from published literature or designed with Primer 3.0 software (Applied Biosystems, Foster City, Calif.) in the lab and synthesized by Integrated DNA Technologies (IDT, Coralville, Iowa). DNA from 2-5 µl of sample (whole blood, serum, or plasma) was added to each 50 µL PCR reaction. PCR was run on 7900HT (Applied Biosystems, Foster City, Calif.) by following manufacturer's standard protocol at specified annealing temperature. The copy number was analyzed with SDS 2.3 software (Applied Biosystems, Foster City, Calif.) based on standard curve from CMV Quantitated Viral DNA.

As shown in Table 2, the gB primer/probe set gB21/22/23 displayed the lowest threshold for detection of CMV standards using limiting dilutions of genomic CMV DNA, the highest frequency of CMV DNA detection in peripheral blood specimens from patients with GBM, and the earliest logarithmic amplification cycle (Ct value) of the probe and primer sets evaluated.

There were significantly different Ct values amongst the fifteen primer/probe combinations evaluated, with Ct values ranging from 31.5 to 38.1. This indicates over a 100-fold difference in the sensitivity of various primer/probes in detection of identical concentrations of CMV DNA standards in the blood. The differences in sensitivity between primer/probe sets resulted in false negatives using less sensitive probe combinations at limiting levels of CMV standards and also false negatives in blood samples from patients with GBM (Table 2).

Example 14

Detection of Viral Reactivation in Patients Undergoing Allogeneic Bone Marrow Transplant To further examine the qualitative and/or quantitative PCR methods described in Examples 12 and 13, the detection of CMV viremia in patients being monitored serially for viral reactivation after undergoing allogeneic bone marrow transplantation (aBMT) was evaluated.

Thirty serum samples obtained serially from 5 patients after aBMT were evaluated using the qualitative and quantitative PCR assays of the invention and also in the Duke Clinical Microbiology Laboratory using the CMV UL54 analyte-specific reagent (ASR) test (Roche Diagnostics, Indianapolis, Ind.). The testing laboratory was blinded to the results of the ASR test, and patient samples were evaluated as to whether they were positive or negative by the qualitative laboratory PCR assay after gel electrophoresis analysis and viral load in copy number per ml of blood was determined using the quantitative laboratory PCR assay.

Detection of CMV DNA by ASR test conducted by the Clinical Microbiology Laboratory at Duke University Medical Center and the qualitative and quantitative PCR tests are shown in Table 7.

TABLE 7

Comparison of laboratory PCR tests to diagnostic PCR assay

| # | Patient | Date collected | Roche UL54 ASR | Lab Quantitative PCR gB | Lab Qualitative PCR gB |
|---|---|---|---|---|---|
| 1 | AB | 20-Jun | 1121 | 424 | Pos |
| 2 | AB | 27-Jun | 2998 | 254 | Pos |
| 3 | AB | 4-Jul | 3150 | 237 | Pos |
| 4 | AW | 10-Jan | 0 | 187 | Pos |
| 5 | AW | 7-Feb | 0 | 45 | Pos |
| 6 | BH | 30-May | 0 | 0 | Neg |
| 7 | BH | 6-Jun | 0 | 0 | Neg |
| 8 | BH | 13-Jun | 0 | 0 | Neg |
| 9 | BH | 20-Jun | 0 | 375 | Pos |
| 10 | BH | 27-Jun | 0 | 0 | Neg |
| 11 | BH | 4-Jul | 0 | 0 | Neg |
| 12 | BH | 11-Jul | 0 | 0 | Neg |
| 13 | BH | 18-Jul | 0 | 1781 | Pos |
| 14 | BH | 25-Jul | 0 | 196 | Pos |
| 15 | BH | 1-Aug | 1561 | 262 | Pos |
| 16 | FD | 27-Jun | 0 | 0 | Neg |
| 17 | FD | 11-Jul | 0 | 0 | Neg |
| 18 | FD | 18-Jul | 0 | 0 | Neg |
| 19 | FD | 25-Jul | 6335 | 649 | Pos |
| 20 | FD | 1-Aug | 5705 | 1640 | Pos |
| 21 | JAG | 10-May | 0 | 0 | Neg |
| 22 | JAG | 18-Jul | 0 | 0 | Pos |
| 23 | JAG | 25-Jul | 0 | 0 | Neg |
| 24 | JAG | 1-Aug | 0 | 305 | Neg |
| 25 | OptiQuant | 5,000 | nt | 206 | Pos |
| 26 | OptiQuant | 500,000 | nt | 7739 | Pos |
| 27 | TB | 27-Jun | 0 | 0 | Pos |
| 28 | TB | 6-Jul | 0 | 0 | Pos |
| 29 | TB | 25-Jul | 0 | 0 | Neg |
| 30 | TB | 1-Aug | 0 | 0 | Neg |

Positive results were confirmed by isolation of DNA bands after gel electrophoresis and DNA sequencing, indicating no false positives by our PCR test. After analysis, results from the clinical diagnostic evaluation of these patients by the ASR test were unblinded. The PCR test was positive in all cases of CMV viremia deemed positive by the Roche CMV UL54 ASR qPCR test conducted by the Clinical Microbiology Laboratory indicating no false negatives by the PCR test of the invention. However, the PCR tests of the present invention detected viral DNA in several patient samples prior to detection of viral reactivation by the clinical diagnostic tests (Table 7). In some cases, viremia was detected six weeks prior to the first positive result by the clinical diagnostic assay. These results were confirmed as true positives by DNA sequencing of amplified bands and identified as CMV using NCBI DNA database.

These results indicate that the laboratory PCR method of the invention is accurate for detection of CMV DNA and capable of detecting viral reactivation in patients undergoing aBMT that is below the threshold of detection of the Roche UL54 ASP assay. These results highlight the utility of this assay as an easier, faster, and more sensitive detection assay detection of CMV DNA and warrant further study to validate the use of this assay for prophylactic monitoring of patients at risk for CMV disease as well as investigating the association of CMV with diseases such as malignancy and atherosclerosis where detection has been controversial.

Example 15

Sequencing of gB (UL55) DNA from GBM Tumor Specimens Identifies Viral Genotype The identity of viral strains associated with GBM tumors was investigated by PCR amplification and DNA sequencing of a strain variable region of the gB (UL55) gene. CMV gB DNA from twenty-two surgically resected GBM specimens was amplified using the gBi1i2 primer set, DNA analyzed by gel electrophoresis, and amplified bands excised and subjected to DNA sequencing. DNA sequences were searched using the NCBI DNA database for sequence identity and all DNA matched to CMV gB. The strain identity and gB family was determined by the examination of the NCBI database for DNA sequence identity. The strain(s) with highest degree of homology are listed in Table 8.

TABLE 8

Identity & Strains of HCMV gBi1i2 PCR Sequences for 22 GBM Patients

| Patient | Identity % Compared to 1T (88 bp) | Identity % Compared to 17T (85 bp) | Identity % Compared to 20T (99 bp) | Identity % Compared to 21T (99 bp) | Strains | gB Subtypes |
|---|---|---|---|---|---|---|
| 1T | 100 | 99 | 91 | 90 | Merlin N1 | gB1 (97%) |
| 2T | 91 | 92 | 86 | 87 | Merlin N1 | gB1 (86%) |
| 3T | 92 | 94 | 90 | 91 | Towne | gB1 (90%) |
| 4T | 94 | 96 | 94 | 89 | AD169 N12 | gB2 (92%) |
| 5T | 95 | 99 | 94 | 92 | Merlin Towne N1 | gB1 (94%) |

TABLE 8-continued

Identity & Strains of HCMV gBi1i2 PCR Sequences for 22 GBM Patients

| Patient | Identity % Compared to 1T (88 bp) | Identity % Compared to 17T (85 bp) | Identity % Compared to 20T (99 bp) | Identity % Compared to 21T (99 bp) | Strains | gB Subtypes |
|---|---|---|---|---|---|---|
| 6T | 93 | 95 | 91 | 88 | AD169 N12 | gB2 (93%) |
| 7T | 95 | 96 | 90 | 93 | Merlin Towne N1 | gB1 (92%) |
| 8T | 94 | 95 | 88 | 90 | Merlin N1 | gB1 (97%) |
| 9T | 93 | 95 | 91 | 86 | AD169 N12 | gB2 (96%) |
| 10T | 96 | 98 | 90 | 93 | Towne | gB1 (96%) |
| 11T | 96 | 100 | 92 | 89 | Merlin Towne N1 | gB1 (93%) |
| 12T | 98 | 96 | 89 | 91 | Merlin N1 | gB1 (95%) |
| 13T | 88 | 90 | 83 | 84 | Merlin N1 | gB1 (92%) |
| 14T | 100 | 99 | 90 | 89 | Merlin N1 | gB1 (96%) |
| 15T | 96 | 100 | 92 | 93 | Merlin N1 | gB1 (97%) |
| 16T | 94 | 96 | 97 | 92 | AD169 N12 | gB2 (95%) |
| 17T | 99 | 100 | 95 | 94 | Towne | gB1 (97%) |
| 18T | 92 | 94 | 91 | 89 | AD169 N12 | gB2 (91%) |
| 19T | 94 | 98 | 94 | 93 | Towne | gB1 (95%) |
| 20T | 91 | 95 | 100 | 89 | AD169 N12 | gB2 (94%) |
| 21T | 90 | 94 | 89 | 100 | Towne | gB1 (93%) |
| 22T | 88 | 90 | 86 | 94 | Merlin N1 | gB1 (93%) |

Figure 19:
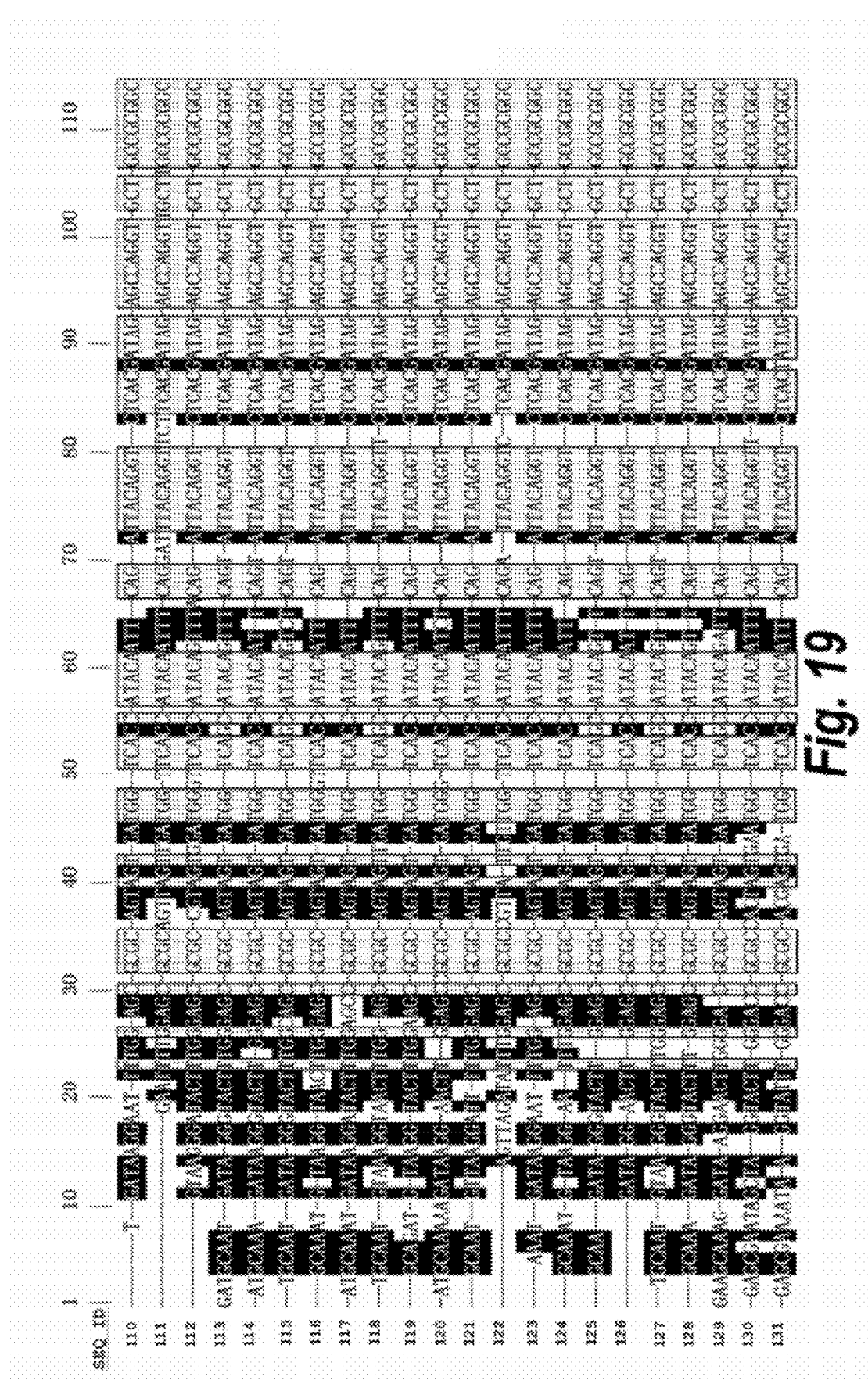
FIG. 19 shows sequence homology. The amplified gB (UL55) DNA from 22 freshly resected GBM specimens was evaluated by DNA sequencing performed in the Duke DNA Sequencing Core Facility. Sequence alignment was performed using Vector NTI Advance 10 (Invitrogen, Carlsbad, Calif.). Homology to identified CMV strains was evaluated by BLAST of NCBI DNA database. Areas of sequence variance between samples are shown in black with nucleotide differences highlighted in white. Dotted indicates conserved identity throughout all 22 specimens. White and black indicates areas of sequence variation.

Sequence alignment of viral DNA from the GBM specimens revealed unique viral isolates from the GBM specimens with DNA sequence variation up to 17% between clinical isolates (FIG. 19; and Table 8). Comparison of amplified viral DNA gB sequence to gB gene sequences within the NCBI database was also conducted and the highest degree of homology to gB genotypes are listed in Table 8. In cases where identical degree of homology to more than one gB genotype was revealed, the viral strain identity was used to determine the gB genotype. Several isolates had the same degree of homology with more than one strain of CMV and were listed accordingly. Strains from GBM specimens were found to be homologous with Merlin (gB isotype 1), N1 (gB isotype 1), Towne (gB isotype 1), AD169 (gB isotype 2), and N12 (gB isotype 2) strains of CMV, indicating that distinct viral isolates were detected in tumor specimens, and also that GBM tumors are permissive for infection by the gB1 and gB2 family genotypes of CMV virus. The distribution of gB genotypes observed was gB1 16/22 (72.7%); gB2 6/22 (27.3%).

These results at least demonstrate that GBM specimens are more frequently infected by CMV strains of the gB1 genotype. Several patient tumor samples were re-analyzed months apart beginning with DNA extraction from cryopreserved whole blood or tumor specimens, PCR amplification, and DNA sequencing of gB amplicons, and identical viral sequences were obtained demonstrating the fidelity of viral identification in these samples.

The consistent detection of an association between CMV and various disease states has been controversial, with conflicting findings by various laboratories reporting on the presence of viral DNA and proteins within pathologic lesions. The above examples describe PCR-based assays and the strain identity of 22 clinical strains of CMV detecting in surgically resected GBM specimens. The development of the CMV PCR tests for reliable detection of CMV in accordance with the present invention also can, among other things, facilitate studies into the role CMV plays in glioma development and progression. GBM tumors were found to be infected by strains matching the gB1 and gB2 genotypes with a predominance of gB1 type viruses. The gB1 genotype is the most prevalent viral family found in clinical CMV infections in the U.S. but the lack of any detection with the highest degree of homology matching clinical strains of the gB3 or gB4 genotypes suggests that there may be a restricted tropism for CMV infection of malignant gliomas.

Detection of viral DNA within tumor specimens is not a trivial issue even in tumors where the association has been well established such as in the case of human papilloma virus associated cervical cancers, and detection can often be at or below the limits of sensitivity by standard PCR assays. As shown above, several parameters were determined that enhanced the detection of low levels of viral DNA in the blood and tumors of patient with newly-diagnosed GBM.

Primers spanning the same region of DNA within the gB gene and differing only by the distance between the primer sets demonstrated an amplicon size dependent frequency of detection of viral DNA. gBi1i2 and gB-i3i4, which have the smallest amplicon sizes within this region also gave the highest detection rates, indicating that false negative results can be due to inefficient amplification of larger DNA fragments and not the absence of viral DNA within samples when viral DNA may be limiting. Analysis of 29 independently derived CMV primer sets spanning 11 different genes demonstrated an inverse correlation between amplicon size and detection rate of CMV DNA. These results suggest that false negative PCR detection by others of limiting amounts of viral DNA can be due to ineffective extraction and amplification conditions and cannot necessarily be deemed to be conclusive. Moreover, extraction and implication conditions can account for false negative results in viral DNA detection.

The majority of the amplified products were confirmed by DNA sequencing and in all cases CMV specific DNA was amplified. And, in order to release viral DNA more efficiently from samples, blood was snap frozen in liquid nitrogen, then incubated at higher temperature (95° C.) than the suggested temperature of 65° C. by the TissueDirect™ kit after addition of lysis buffer. Also incorporated was an EtOH precipitation step after DNA extraction in order to concentrate DNA and eliminate PCR inhibitors that are often present in the crude sample extracts. For qualitative PCR, a combination of polyacrylamide gel and SYBR Gold staining provided increased PCR detection sensitivity of at least 10 fold compared to conventional agarose gel stained with ethidium bromide. This increased sensitivity allowed detection without use of more intensive protocols, such as nested PCR or gene specific probe hybridization of blotted DNA. This assay has the added advantage of being able to utilize small volumes of specimen (10-20 µL) allowing repeated analysis of samples and preservation of patient samples that may be limiting. Furthermore, the evaluation in patients undergoing bone marrow transplantation demonstrated that the assay is capable of earlier detection of viral reactivation in immunosuppressed patients than currently available diagnostic PCR tests.

It has been reported that CMV has an association and possible pathogenic role in a number of disease processes including cancer, atherosclerosis, and inflammatory bowel disease. The detection of CMV in association with these diseases, however, has varied considerably amongst investigator's laboratories. The relatively simple and enhanced amplification detection method that can utilize small volumes of blood and tissue specimens can allow for more reliable determination of the association of CMV with such disease processes.

What is claimed is:

1. A method for eliciting in a subject an immune response to a cancer cell that expresses a CMV antigen, the method comprising:
   selecting a subject in need of treatment related to the presence of the cancer cell; detecting the expression of the CMV antigen by the cancer cell in the subject, and administering to the subject a pharmaceutically acceptable composition comprising at least one CMV antigen, wherein the pharmaceutically acceptable composition, when administered to the subject, elicits an immune response to the cancer cell.

2. The method of claim 1, wherein the at least one CMV antigen correspond to a polypeptide, or immunogenic fragment thereof, selected from the group consisting of: capsid polypeptides, tegument polypeptides, and envelop polypeptides.

3. The method of claim 1, wherein the at least one CMV antigen correspond to a polypeptide, or an immunogenic fragment thereof, selected from the group consisting of: phosphoprotein unique lon g83 (ppUL83; a/k/a pp65), glycoprotein UL55 (gpUL55; a/k/a gB), UL123 immediate early I (IE1) protein, UL122 IE2 protein, UL111A (a/k/a mtrII), US28, ppUL32, ppUL65, ppUL80a, ppUL82, ppUL98a, ppUL99, pgUL4, (a/k/a gp48), gpUL16, gpUL18, (a/k/a MHC), gpUL75 (a/k/a gH), gpUL100, gpUL110 (a/k/a gM), gpUL115 (a/k/a gL), pUL46, pUL48, pUL56, pUL86 (a/k/a MCP), glycoprotein unique short 10 (gpUS10), gpUS11, glycoprotein complex II (gcII), gp65, and pg93.

4. The method of claim 1, wherein the pharmaceutically acceptable composition further comprises at least one adjuvant, or a nucleic acid encoding the adjuvant.

5. The method of claim 4, wherein the adjuvant is a cytokine selected from the group consisting of: GM-CSF, G-CSF, IL-2, IL-4, IL-7, IL-12, IL-5, IL-21, TNF-α, and M-CSF.

6. The method of claim 1, wherein the at least one CMV antigen comprises an amino acid sequence corresponding to SEQ ID NO:109.

7. The method of claim 1, wherein the composition further comprises a glycoprotein UL55 (gpUL55; a/k/a gB) or an immunogenic fragment thereof.

8. The method of claim 1, wherein the composition further comprises a UL123 immediate early 1 (IE1) protein or an immunogenic fragment thereof.

* * * * *